(12) United States Patent
Green et al.

(10) Patent No.: US 8,876,861 B2
(45) Date of Patent: Nov. 4, 2014

(54) CLOSURE DEVICE, DEPLOYMENT APPARATUS, AND METHOD OF DEPLOYING A CLOSURE DEVICE

(75) Inventors: Stephen M. Green, Syracuse, NY (US); Brian Fairman, Auburn, NY (US); Herbert F. Brodt, Lafayette, NY (US); David K. Boger, Vestavia Hills, AL (US)

(73) Assignee: Transluminal Technologies, Inc., Syracuse, NY (US)

( * ) Notice: Subject to any disclaimer, the term of this patent is extended or adjusted under 35 U.S.C. 154(b) by 84 days.

(21) Appl. No.: 12/917,979

(22) Filed: Nov. 2, 2010

(65) Prior Publication Data
US 2011/0046665 A1    Feb. 24, 2011

Related U.S. Application Data

(63) Continuation-in-part of application No. 12/204,977, filed on Sep. 5, 2008, now Pat. No. 8,137,380.

(60) Provisional application No. 60/971,618, filed on Sep. 12, 2007.

(51) Int. Cl.
*A61B 19/00* (2006.01)
*A61B 17/00* (2006.01)

(52) U.S. Cl.
CPC ... *A61B 17/0057* (2013.01); *A61B 2017/00654* (2013.01); *A61B 2017/00367* (2013.01); *A61B 2017/00659* (2013.01); *A61B 2017/00637* (2013.01); *A61B 2017/00641* (2013.01); *A61B 2017/00623* (2013.01); *A61B 2017/00004* (2013.01)
USPC ............................ 606/213; 606/139; 606/215

(58) Field of Classification Search
None
See application file for complete search history.

(56) References Cited

U.S. PATENT DOCUMENTS 4,744,364 A    5/1988    Kensey
(Continued)

FOREIGN PATENT DOCUMENTS

JP          54-113288         8/1979
WO    WO2006110614 A2    10/2006
(Continued)

OTHER PUBLICATIONS

PCT International Search Report dated May 16, 2012, International Application No. PCT/US2011/058936.

*Primary Examiner* — Melanie Tyson
*Assistant Examiner* — Todd J Scherbel
(74) *Attorney, Agent, or Firm* — George R. McGuire; Frederick J. M. Price; Bond Schoeneck & King, PLLC

(57) ABSTRACT

The present invention relates a closure device implant for sealing an opening formed through biological tissue including a plug, a rigid wire including a plastically deformable portion configurable between an unrestrained position and a restrained position relative to the plug, wherein a distal end of the wire is substantially spherically shaped, and a footplate attached to the wire, wherein the footplate comprises an elongated plate portion including a wire channel. The present invention also relates to a closure device deployment device including an elongated housing, a sheath assembly connected to the housing, and at least two sliding members slidably connected to the housing.

25 Claims, 99 Drawing Sheets

(56) References Cited

U.S. PATENT DOCUMENTS

| | | | |
|---|---|---|---|
| 4,890,612 A | 1/1990 | Kensey et al. |
| 5,222,974 A | 6/1993 | Kensey et al. |
| 5,282,827 A | 2/1994 | Kensey et al. |
| 5,312,435 A | 5/1994 | Nash et al. |
| 5,342,393 A | 8/1994 | Stack |
| 5,350,399 A * | 9/1994 | Erlebacher et al. ............ 606/213 |
| RE34,866 E | 2/1995 | Kensey et al. |
| 5,391,182 A | 2/1995 | Chin |
| 5,411,520 A | 5/1995 | Nash et al. |
| 5,441,517 A | 8/1995 | Kensey et al. |
| 5,531,759 A | 7/1996 | Kensey |
| 5,545,178 A | 8/1996 | Kensey et al. |
| 5,593,422 A | 1/1997 | Muijs Van de Moer et al. |
| 5,641,501 A | 6/1997 | Cooper et al. |
| 5,645,566 A | 7/1997 | Brenneman et al. |
| 5,649,959 A | 7/1997 | Hannah et al. |
| 5,662,681 A | 9/1997 | Nash et al. |
| 5,676,689 A | 10/1997 | Kensey et al. |
| 5,690,674 A | 11/1997 | Diaz |
| 5,700,277 A | 12/1997 | Nash et al. |
| 5,707,393 A | 1/1998 | Kensey et al. |
| 5,725,553 A | 3/1998 | Moenning |
| 5,782,861 A | 7/1998 | Cragg et al. |
| 5,861,004 A | 1/1999 | Kensey et al. |
| 5,916,236 A | 6/1999 | Muijs Van De Moer et al. |
| 5,935,147 A | 8/1999 | Kensey et al. |
| 5,941,898 A | 8/1999 | Moenning et al. |
| 5,984,950 A | 11/1999 | Cragg et al. |
| 6,007,563 A | 12/1999 | Nash et al. |
| 6,017,359 A | 1/2000 | Gershony et al. |
| 6,045,569 A | 4/2000 | Kensey et al. |
| 6,056,768 A * | 5/2000 | Cates et al. .................... 606/213 |
| 6,059,816 A | 5/2000 | Moenning |
| 6,071,300 A | 6/2000 | Brenneman et al. |
| 6,080,183 A | 6/2000 | Tsugita et al. |
| 6,090,130 A | 7/2000 | Nash et al. |
| 6,113,624 A | 9/2000 | Bezwada et al. |
| 6,162,192 A | 12/2000 | Cragg et al. |
| 6,179,863 B1 | 1/2001 | Kensey et al. |
| 6,190,400 B1 | 2/2001 | Van De Moer et al. |
| 6,197,042 B1 | 3/2001 | Ginn et al. |
| 6,277,140 B2 | 8/2001 | Ginn et al. |
| 6,287,332 B1 | 9/2001 | Bolz et al. |
| 6,315,753 B1 | 11/2001 | Cragg et al. |
| 6,368,341 B1 | 4/2002 | Abrahamson |
| 6,371,974 B1 | 4/2002 | Brenneman et al. |
| 6,391,048 B1 | 5/2002 | Ginn et al. |
| 6,425,911 B1 | 7/2002 | Akerfeldt et al. |
| 6,461,364 B1 | 10/2002 | Ginn et al. |
| 6,508,828 B1 | 1/2003 | Akerfeldt et al. |
| 6,527,734 B2 | 3/2003 | Cragg et al. |
| 6,540,735 B1 | 4/2003 | Ashby et al. |
| 6,544,236 B1 | 4/2003 | Cragg et al. |
| 6,610,026 B2 | 8/2003 | Cragg et al. |
| 6,623,509 B2 * | 9/2003 | Ginn .............................. 606/213 |
| 6,632,238 B2 | 10/2003 | Ginn et al. |
| 6,656,207 B2 | 12/2003 | Epstein et al. |
| 6,663,655 B2 | 12/2003 | Ginn et al. |
| 6,712,837 B2 | 3/2004 | Akerfeldt et al. |
| 6,749,621 B2 | 6/2004 | Pantages et al. |
| 6,764,500 B1 | 7/2004 | Muijs Van De Moer et al. |
| 6,780,197 B2 | 8/2004 | Roe et al. |
| 6,786,915 B2 | 9/2004 | Akerfeldt et al. |
| 6,818,008 B1 * | 11/2004 | Cates et al. .................... 606/213 |
| 6,846,319 B2 | 1/2005 | Ginn et al. |
| 6,860,895 B1 * | 3/2005 | Akerfeldt et al. ............. 606/215 |
| 6,863,680 B2 | 3/2005 | Ashby |
| 6,890,343 B2 | 5/2005 | Ginn et al. |
| 6,896,692 B2 | 5/2005 | Ginn et al. |
| 6,942,674 B2 | 9/2005 | Belef et al. |
| 6,964,658 B2 | 11/2005 | Ashby et al. |
| 6,969,397 B2 | 11/2005 | Ginn |
| 7,001,398 B2 | 2/2006 | Carley et al. |
| 7,001,411 B1 | 2/2006 | Dean |
| 7,008,440 B2 | 3/2006 | Sing et al. |
| 7,029,489 B1 | 4/2006 | Ashby et al. |
| 7,037,322 B1 | 5/2006 | Sing et al. |
| 7,048,710 B1 | 5/2006 | Cragg et al. |
| 7,083,635 B2 | 8/2006 | Ginn |
| 7,201,725 B1 | 4/2007 | Cragg et al. |
| 7,250,057 B2 | 7/2007 | Forsberg |
| 7,267,679 B2 | 9/2007 | McGuckin, Jr. et al. |
| 7,326,230 B2 | 2/2008 | Ravikumar |
| D566,272 S | 4/2008 | Walburg et al. |
| 7,361,183 B2 | 4/2008 | Ginn |
| 7,850,710 B2 * | 12/2010 | Huss ............................. 606/213 |
| 2001/0003158 A1 | 6/2001 | Kensey et al. |
| 2002/0004060 A1 | 1/2002 | Heublein et al. |
| 2002/0198562 A1 | 12/2002 | Akerfeldt et al. |
| 2003/0023267 A1 | 1/2003 | Ginn |
| 2003/0144695 A1 | 7/2003 | McGuckin et al. |
| 2004/0019330 A1 | 1/2004 | Ashby |
| 2004/0093025 A1 | 5/2004 | Egnelov |
| 2004/0153122 A1 | 8/2004 | Palermo |
| 2004/0153123 A1 | 8/2004 | Palermo et al. |
| 2004/0215231 A1 | 10/2004 | Fortune et al. |
| 2004/0215232 A1 | 10/2004 | Belhe et al. |
| 2004/0267308 A1 * | 12/2004 | Bagaoisan et al. ............. 606/213 |
| 2005/0085773 A1 | 4/2005 | Forsberg |
| 2005/0085853 A1 | 4/2005 | Forsberg et al. |
| 2005/0085855 A1 | 4/2005 | Forsberg |
| 2005/0090859 A1 | 4/2005 | Ravikumar |
| 2005/0096696 A1 | 5/2005 | Forsberg |
| 2005/0096697 A1 | 5/2005 | Forsberg et al. |
| 2005/0107820 A1 | 5/2005 | Forsberg et al. |
| 2005/0107827 A1 | 5/2005 | Paprocki |
| 2005/0125030 A1 | 6/2005 | Forsberg et al. |
| 2005/0177189 A1 | 8/2005 | Ginn et al. |
| 2005/0192627 A1 | 9/2005 | Whisenant et al. |
| 2005/0192661 A1 | 9/2005 | Griffen et al. |
| 2005/0222614 A1 | 10/2005 | Ginn et al. |
| 2005/0234396 A1 | 10/2005 | Forsberg et al. |
| 2005/0267528 A1 | 12/2005 | Ginn et al. |
| 2005/0273135 A1 | 12/2005 | Chanduszko et al. |
| 2005/0273136 A1 | 12/2005 | Belef et al. |
| 2006/0018954 A1 | 1/2006 | Kuttler |
| 2006/0020315 A1 | 1/2006 | Geistert et al. |
| 2006/0052824 A1 | 3/2006 | Ransick et al. |
| 2006/0052825 A1 | 3/2006 | Ransick |
| 2006/0052863 A1 | 3/2006 | Harder et al. |
| 2006/0052864 A1 | 3/2006 | Harder et al. |
| 2006/0058844 A1 | 3/2006 | White et al. |
| 2006/0064160 A1 | 3/2006 | Gerold et al. |
| 2006/0106418 A1 | 5/2006 | Seibold et al. |
| 2006/0135991 A1 | 6/2006 | Kawaura et al. |
| 2006/0142797 A1 | 6/2006 | Egnelov |
| 2006/0155327 A1 | 7/2006 | Briganti et al. |
| 2006/0195123 A1 | 8/2006 | Ginn et al. |
| 2006/0195124 A1 | 8/2006 | Ginn et al. |
| 2006/0206146 A1 | 9/2006 | Tenerz |
| 2006/0229670 A1 | 10/2006 | Bates |
| 2006/0229672 A1 | 10/2006 | Forsberg |
| 2006/0229673 A1 | 10/2006 | Forsberg |
| 2006/0229674 A1 | 10/2006 | Forsberg |
| 2006/0253037 A1 | 11/2006 | Ginn et al. |
| 2006/0265007 A1 | 11/2006 | White et al. |
| 2006/0287710 A1 | 12/2006 | Lendlein et al. |
| 2007/0010853 A1 | 1/2007 | Ginn et al. |
| 2007/0032823 A1 | 2/2007 | Tegg |
| 2007/0032824 A1 | 2/2007 | Terwey |
| 2007/0050009 A1 | 3/2007 | Flanagan |
| 2007/0055305 A1 | 3/2007 | Schnyder et al. |
| 2007/0073345 A1 | 3/2007 | Pipenhagen et al. |
| 2007/0135842 A1 | 6/2007 | Van de Moer et al. |
| 2007/0156084 A1 | 7/2007 | Belhe et al. |
| 2007/0250080 A1 | 10/2007 | Jones et al. |
| 2007/0255314 A1 | 11/2007 | Forsberg |
| 2007/0270904 A1 | 11/2007 | Ginn |
| 2007/0270940 A1 | 11/2007 | Doty |
| 2007/0276433 A1 * | 11/2007 | Huss ............................. 606/213 |
| 2007/0282352 A1 | 12/2007 | Carley et al. |
| 2007/0282432 A1 | 12/2007 | Stinson et al. |
| 2008/0033535 A1 | 2/2008 | Mueller et al. |
| 2008/0033538 A1 | 2/2008 | Borck et al. |

(56) References Cited

U.S. PATENT DOCUMENTS

2008/0058923 A1 3/2008 Bertsch et al.
2008/0065151 A1 3/2008 Ginn
2008/0071311 A1 3/2008 White et al.
2009/0069844 A1 3/2009 Green
2010/0179589 A1 7/2010 Roorda et al.
2010/0198159 A1 8/2010 Voss

FOREIGN PATENT DOCUMENTS

| WO | WO2006124245 | A2 | 11/2006 |
| WO | WO2006124251 | A2 | 11/2006 |
| WO | WO2007081448 | A2 | 7/2007 |
| WO | WO2007139755 | A2 | 12/2007 |

* cited by examiner

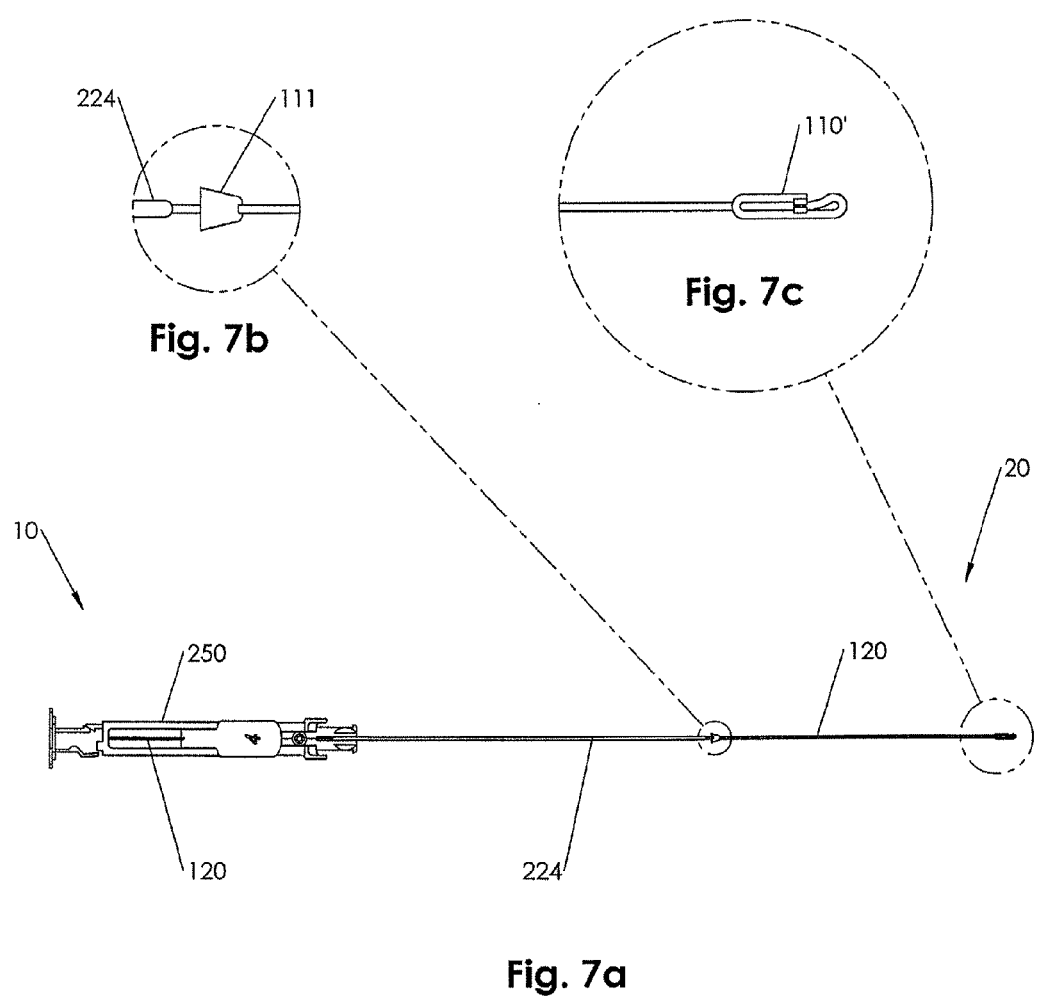

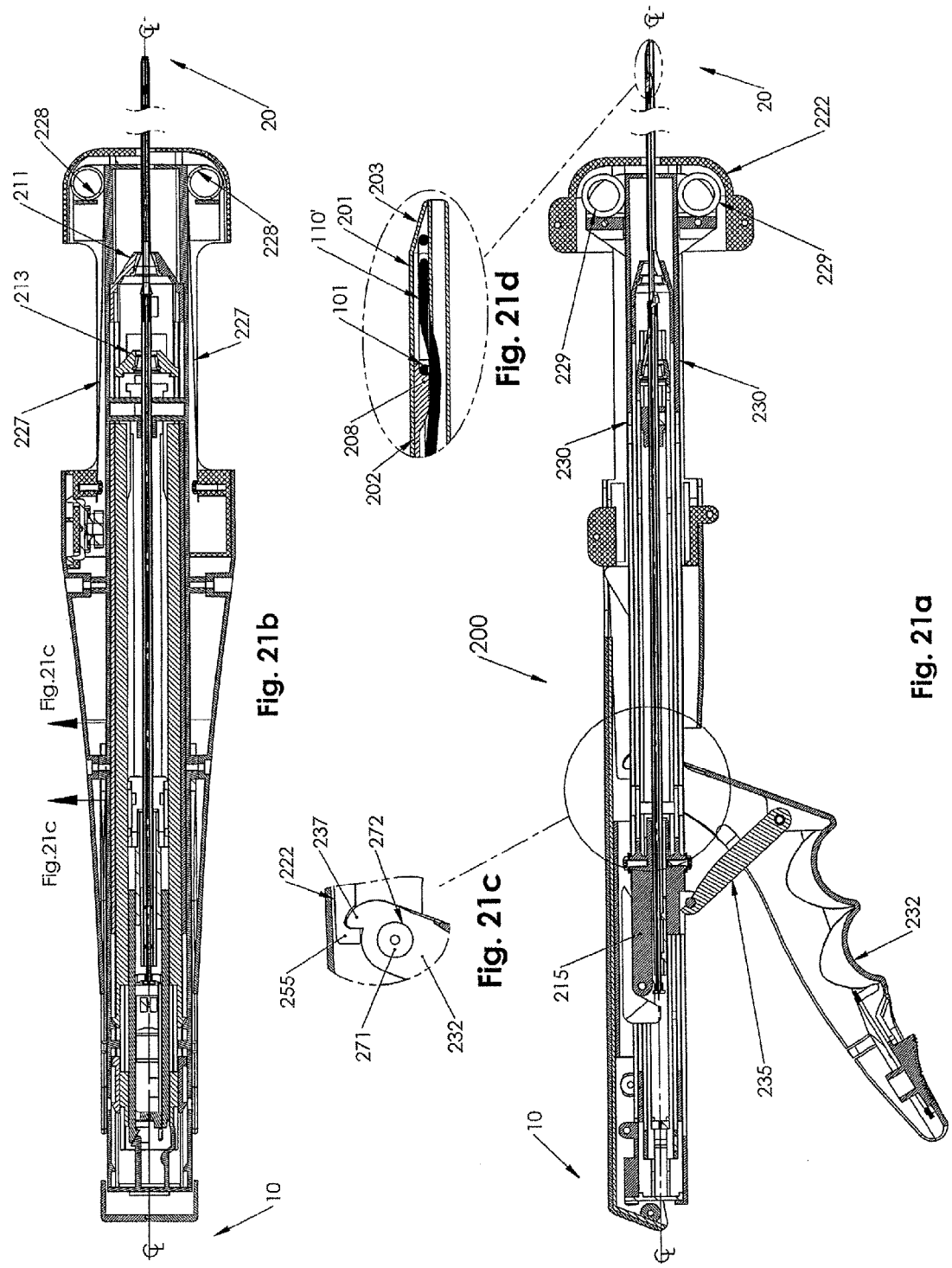

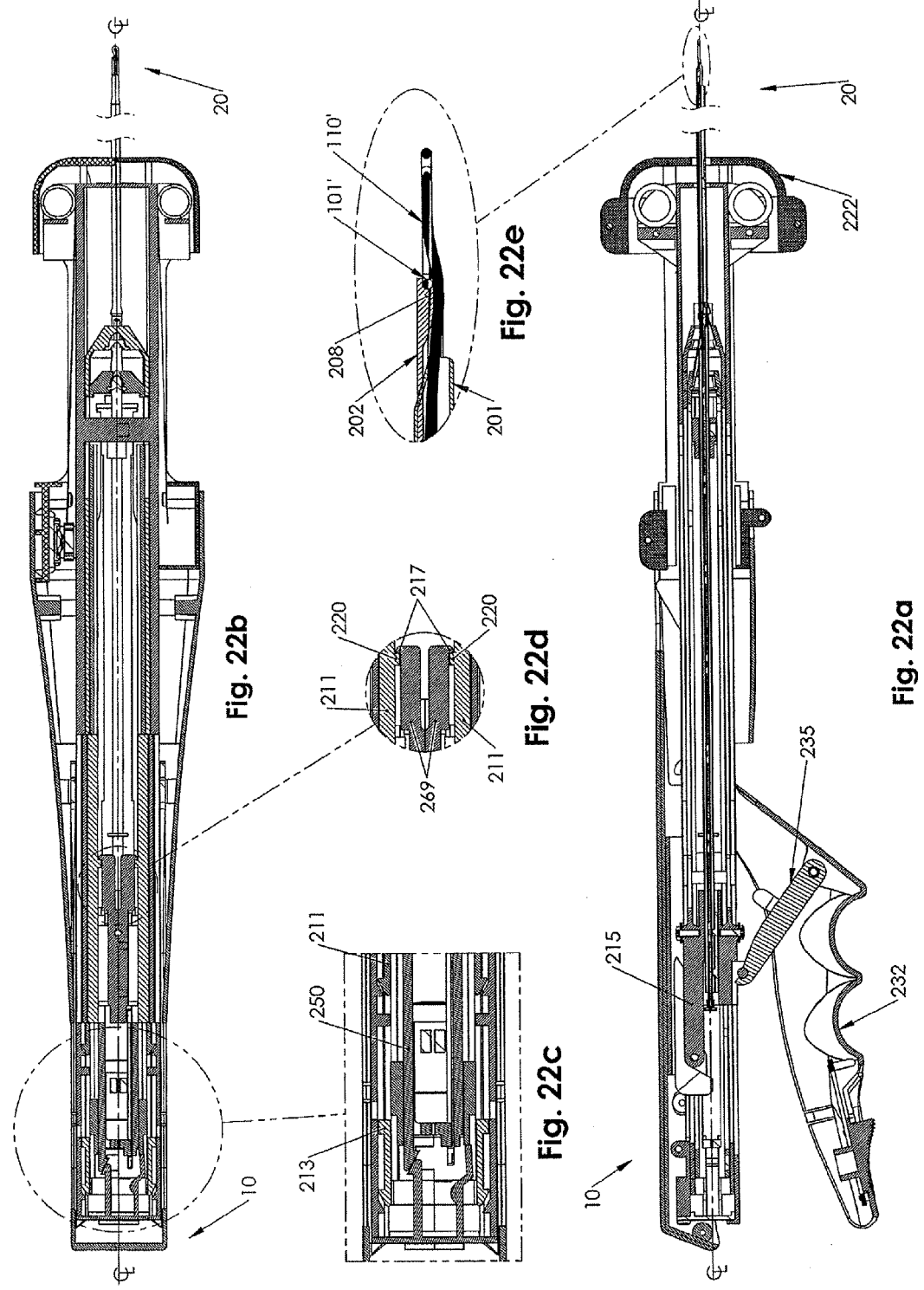

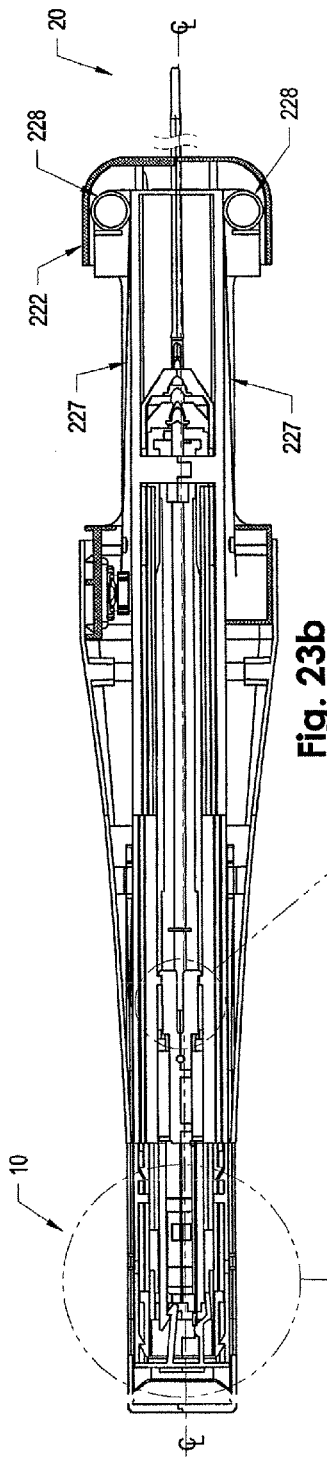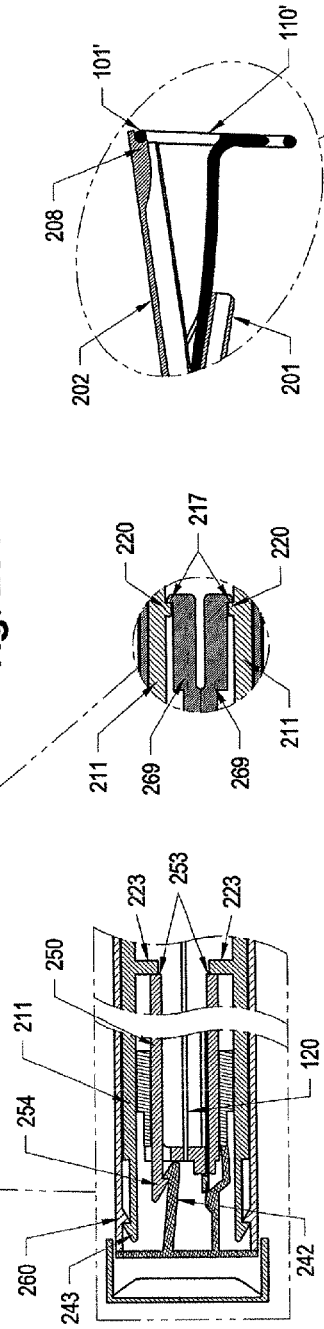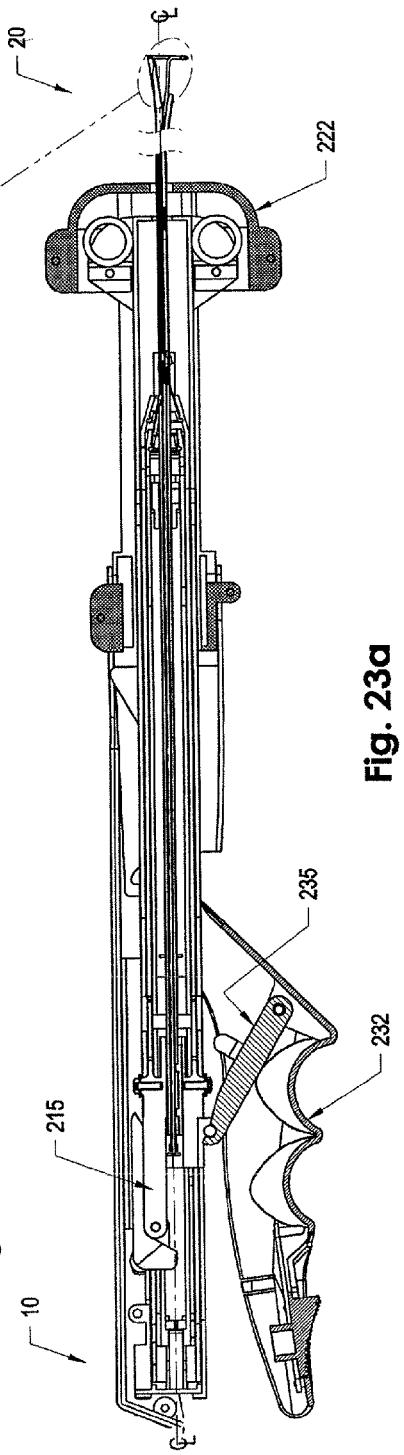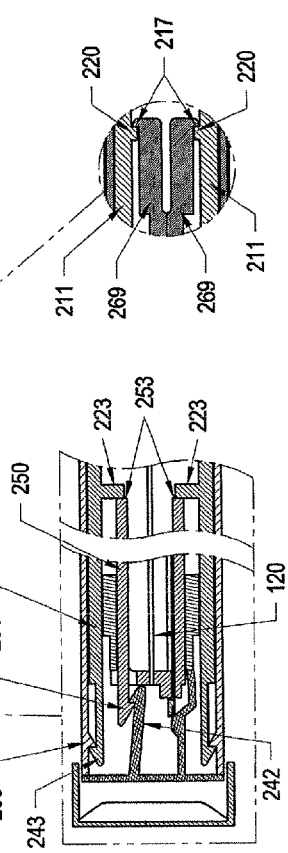
Fig. 23a
Fig. 23b
Fig. 23c
Fig. 23d
Fig. 23e

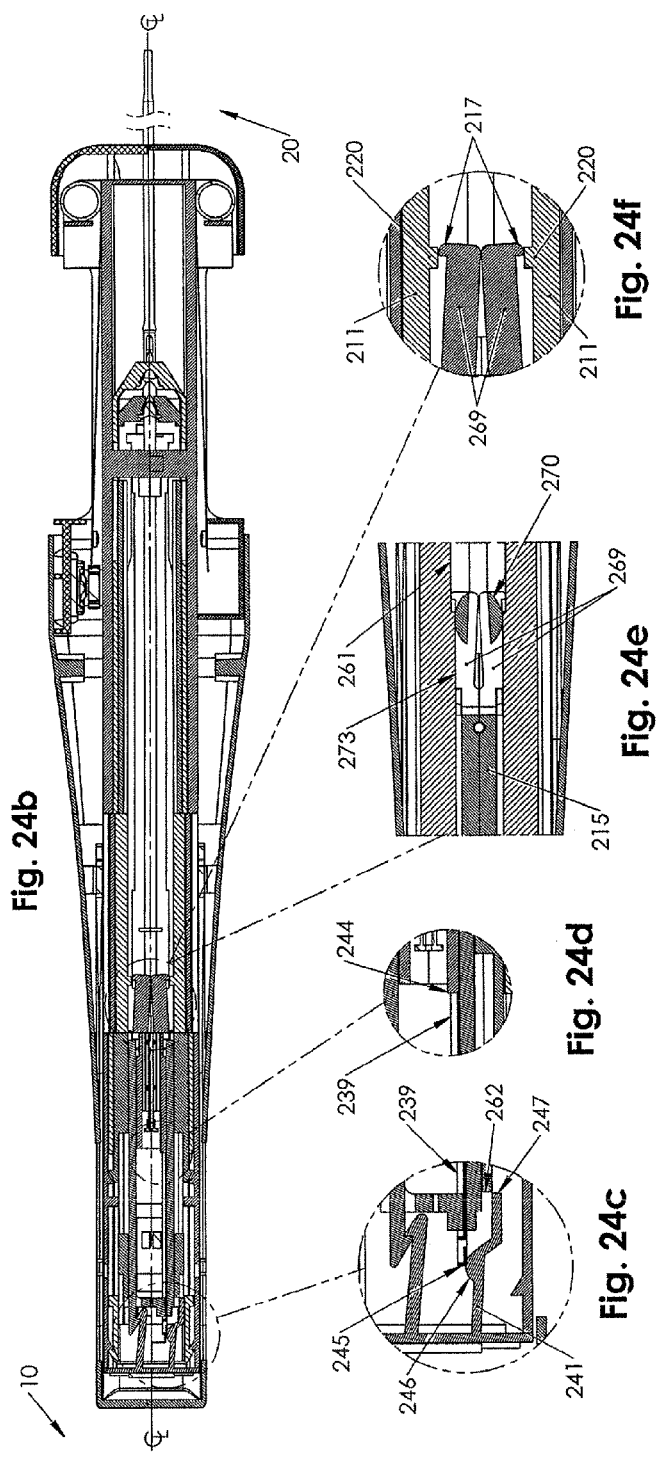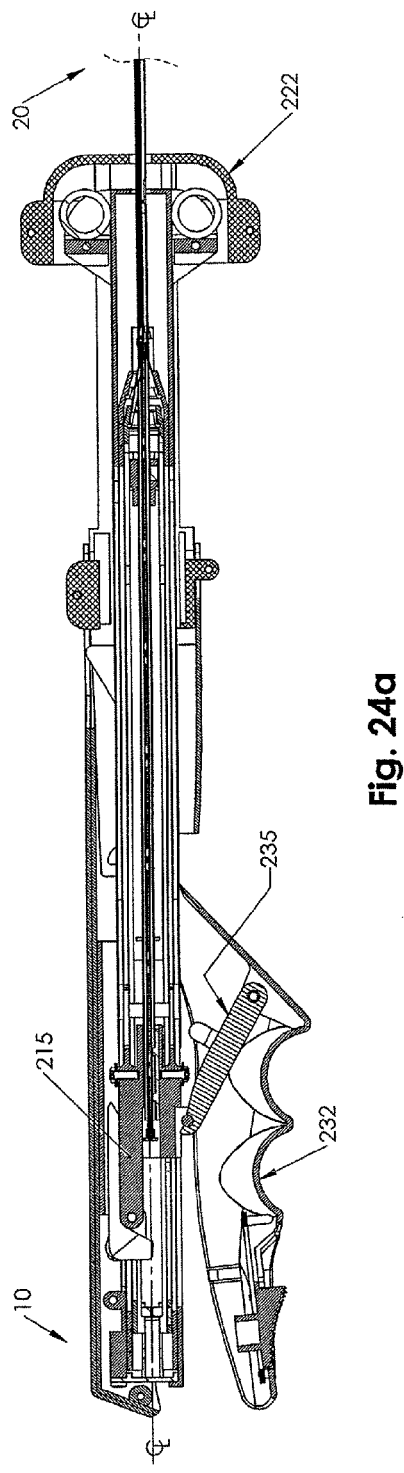

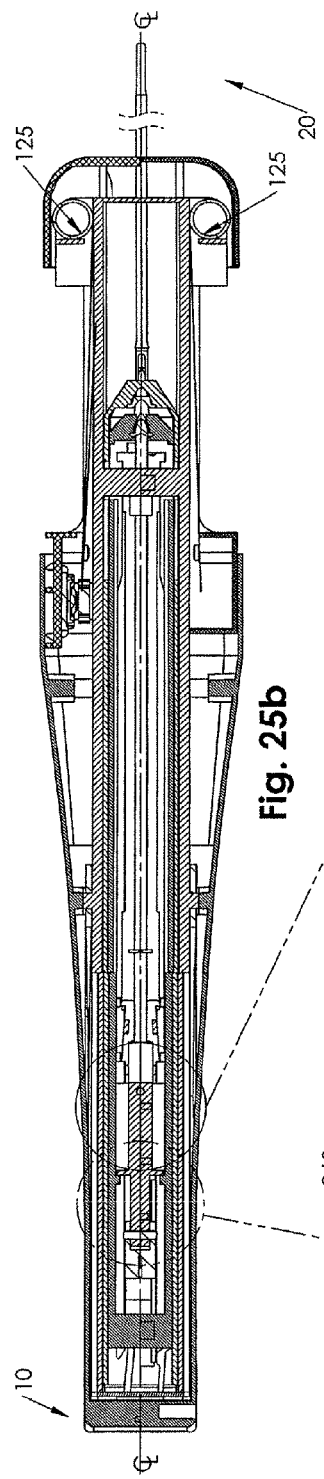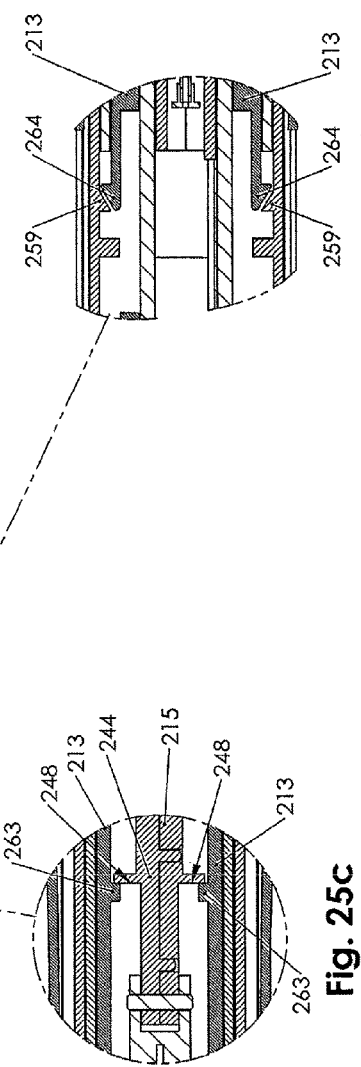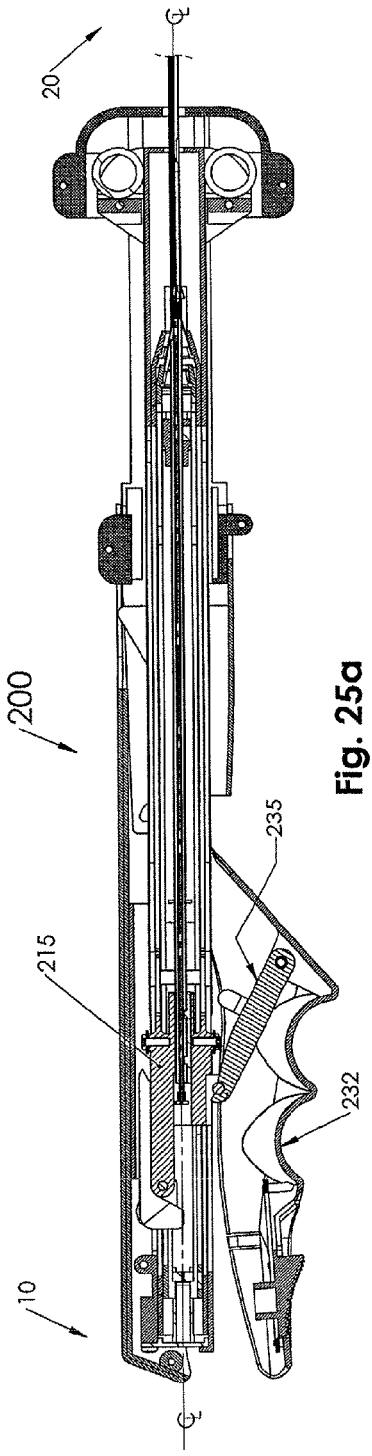

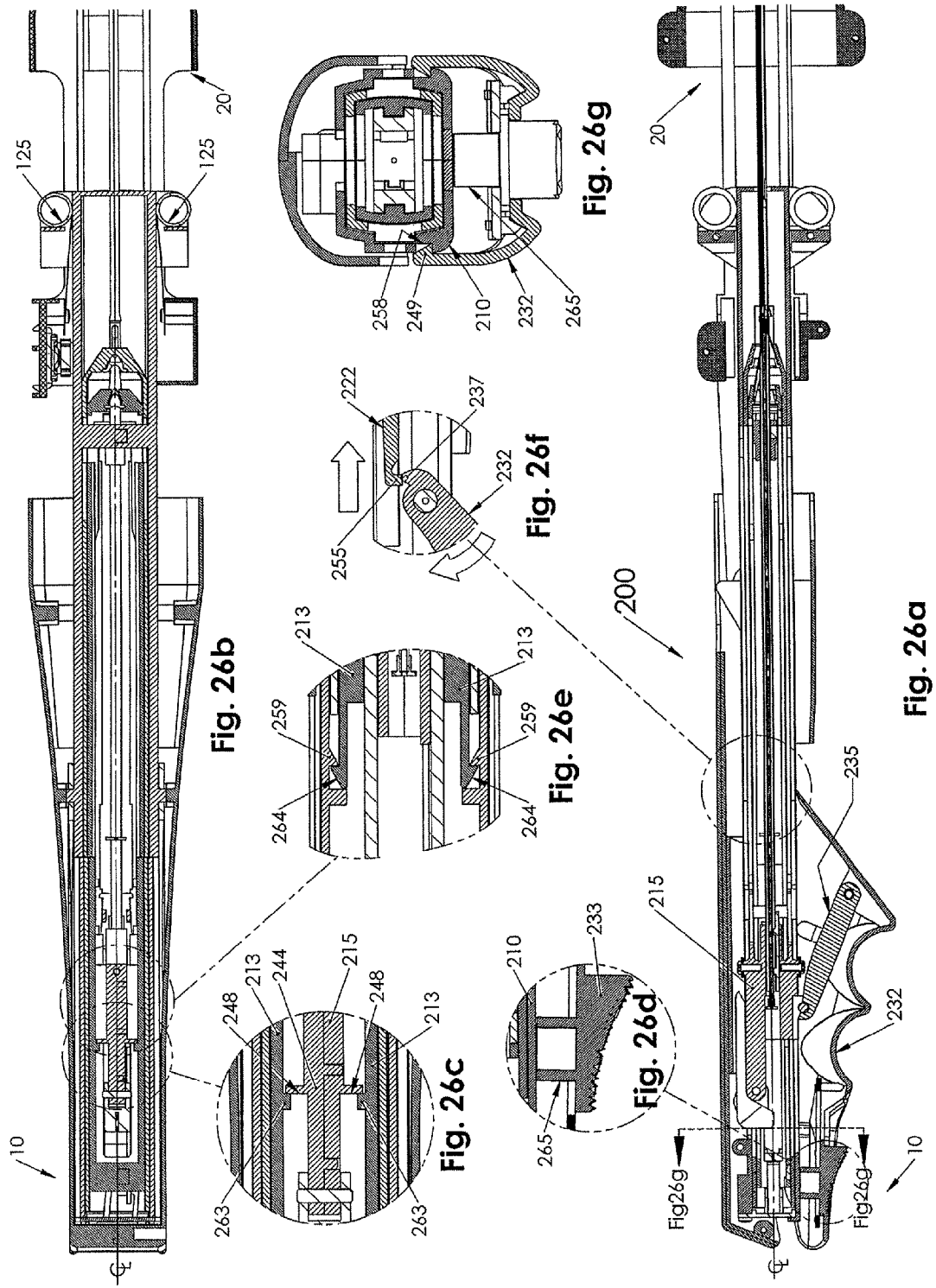

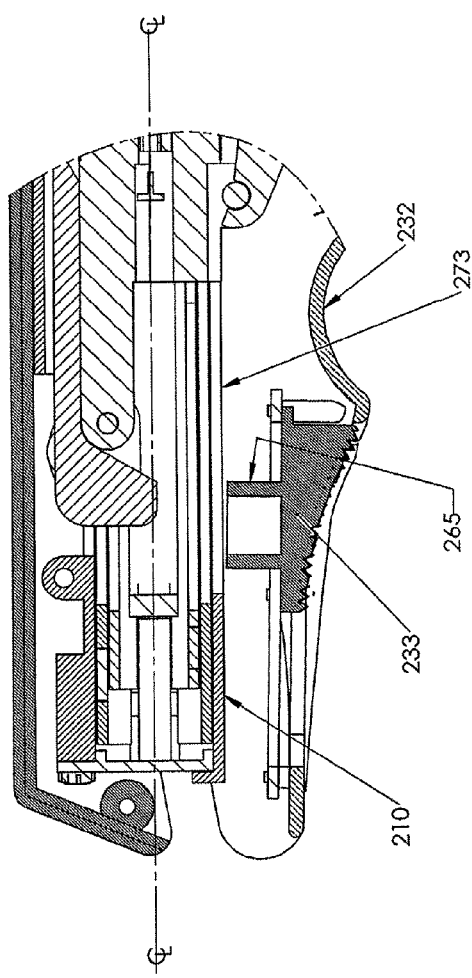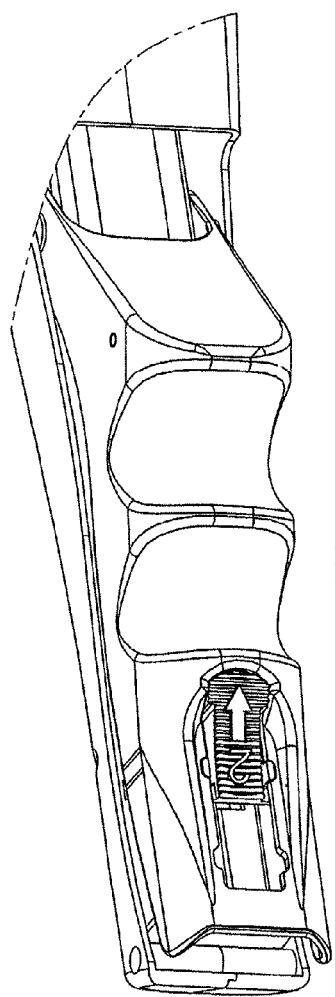
Fig. 28a
Fig. 28b

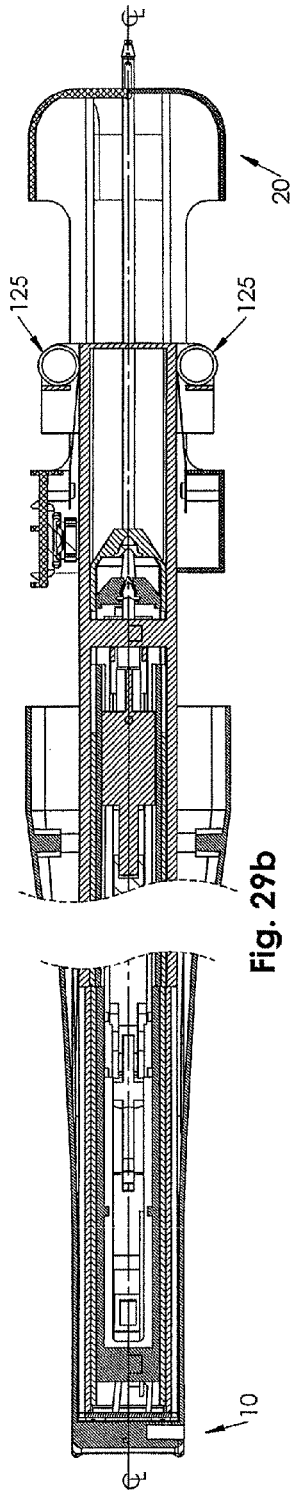
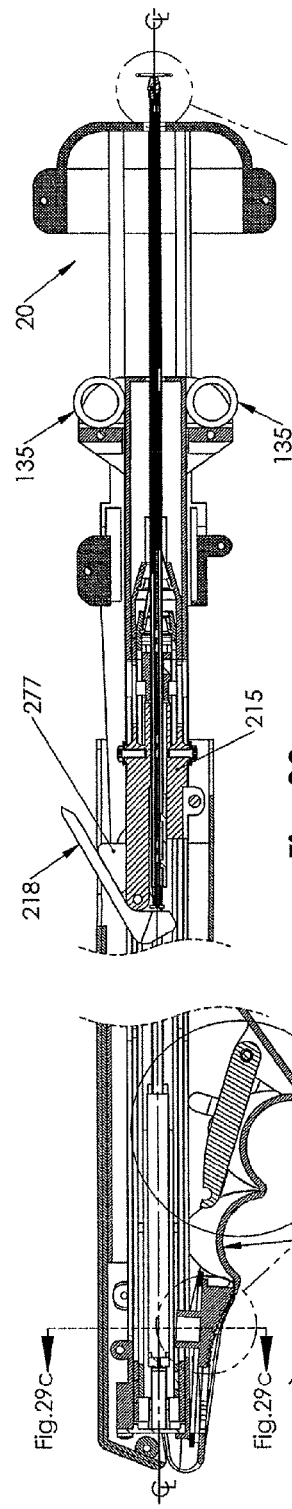
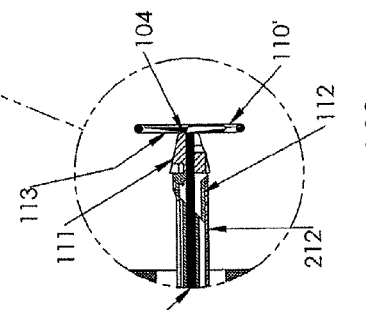
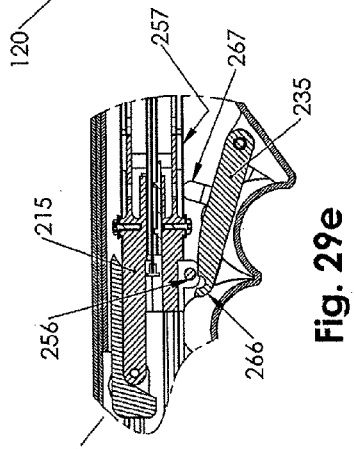
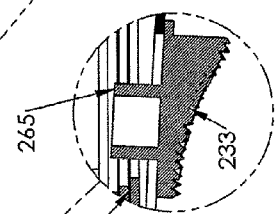
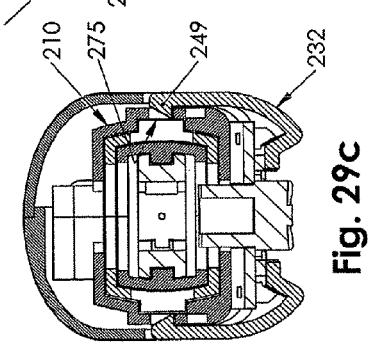

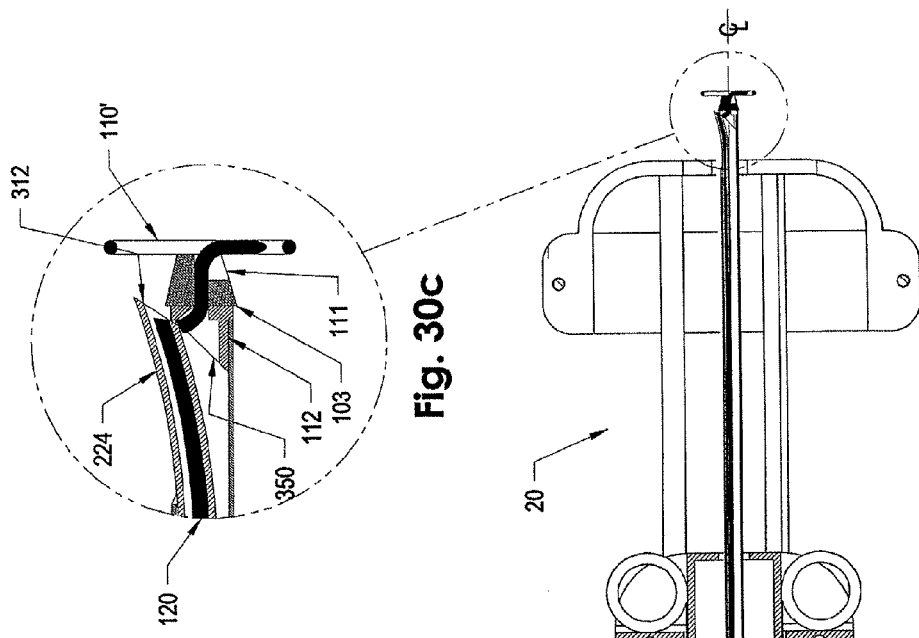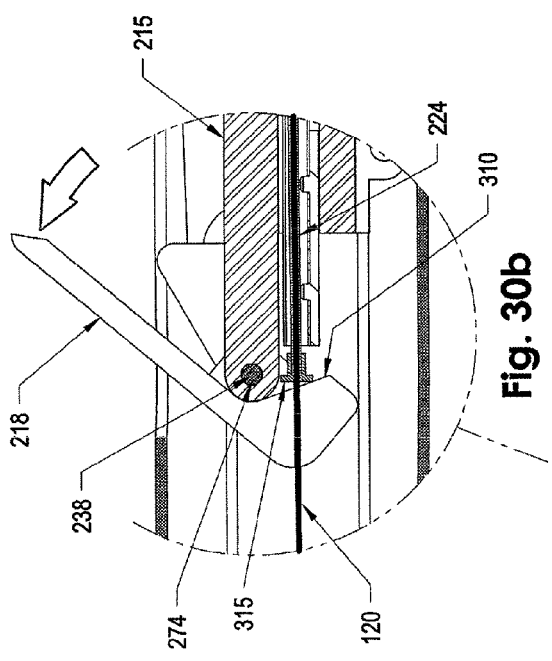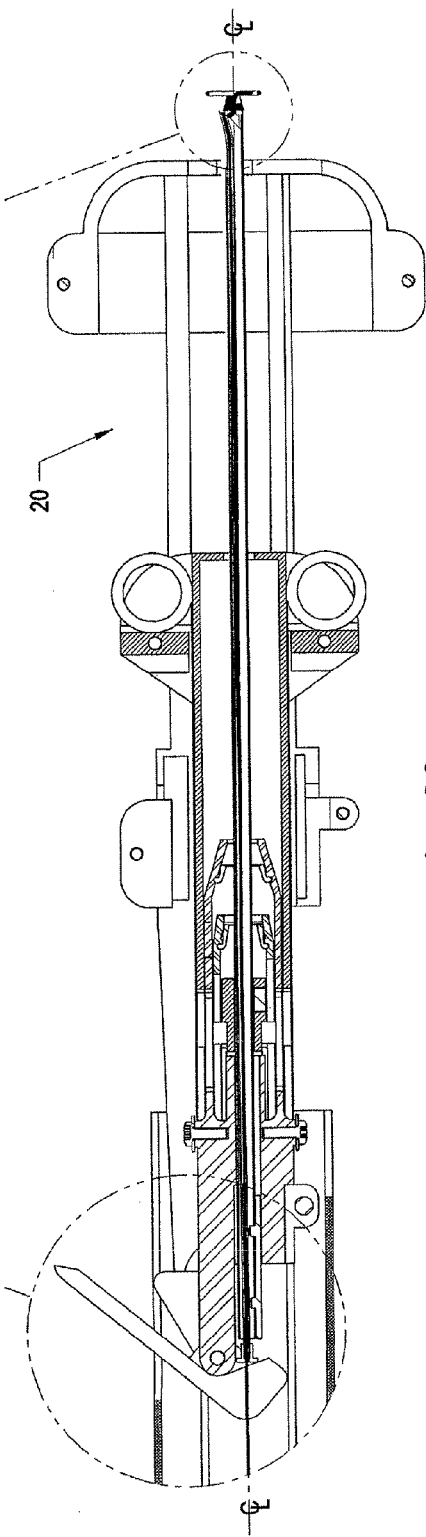
Fig. 30a
Fig. 30b
Fig. 30c

CLOSURE DEVICE, DEPLOYMENT APPARATUS, AND METHOD OF DEPLOYING A CLOSURE DEVICE

RELATED APPLICATION DATA

The present application is a continuation in part of U.S. patent application Ser. No. 12/204,977, filed Sep. 5, 2008 now U.S. Pat. No. 8,137,380, which claims benefit of U.S. provisional patent application No. 60/971,618, filed Sep. 12, 2007, and is hereby incorporated by reference in its entirety.

BACKGROUND OF THE INVENTION

1. Field of Invention

The present invention relates generally to medical devices and methods for sealing and closing passages formed through tissue. More specifically, the present invention relates to devices for sealing or closing an opening formed through biological tissue comprising a distal or outside margin or surface, and a proximal or inside margin or surface (i.e., a wall thickness), and to apparatuses and methods for delivering such devices, to control (or prevent or stop) bleeding (or the flow of other biological fluid or tissue). The openings comprise punctures, incisions, or other openings formed through biological tissue such as blood vessels or organs.

2. Description of Prior Art

Access to arterial and venous vascular systems is necessary for intravascular surgical procedures such as cardiac catheterizations and interventional procedures such as percutaneous transluminal coronary angioplasty or stenting. These intravascular surgical procedures generally are performed by inserting a hollow needle through a patient's skin (percutaneously) and any intervening tissue into the vascular system, e.g., an artery such as a femoral artery. A guide wire may then be passed through the needle lumen into the patient's blood vessel. Once the guide wire is in place the needle may be removed, leaving the guide wire in place. An introducer sheath may be advanced over the guide wire into the vessel, e.g., in conjunction with or subsequent to a dilator. A catheter or other device utilizing the percutaneous opening may then be advanced through a lumen of the introducer sheath and over the guide wire into the desired intravascular position.

Upon completing the intravascular procedure, the catheter, introducer sheath, guide wire and other medical device components may be removed, leaving an opening in the blood vessel wall (the so-called puncture site, or arteriotomy) and the proximal tissue tract through which blood can flow to the outside (bleeding). External pressure (manual compression) may be applied to the percutaneous puncture site until clotting and wound sealing occur. This procedure, however, may be expensive and time consuming, requiring as much as an hour of a physician's or nurse's time. It is also uncomfortable for the patient, and requires that the patient remain immobilized in the operating room, catheterization laboratory, or holding area. In addition, a risk of hematoma exists from bleeding before hemostasis occurs.

Once the bleeding has stopped, an elastic bandage (pressure bandage) or sandbag is often placed over the site of the puncture; this exerts pressure so as to prevent the blood clot from being washed away by the pressure in the blood vessel which can easily happen, especially in the case of an arterial puncture. This pressure bandage or sandbag must remain in place for some time, varying from clinic to clinic from 8 to 24 hours. During the period of time that the pressure bandage is in place, the patient must remain resting in bed. After removing the pressure bandage, the patient can become mobile again. This usually means, in practice, that following a percutaneous arterial procedure, the patient must stay in the hospital for a prolonged period of time, often overnight.

This external pressure procedure (manual compression) is associated with quite a few complications which are inherent in the technique. Intense bleeding can occur in addition to pseudo-aneurysms (whereby a passage exists, via the puncture site, between the lumen of the blood vessel and a clot situated around the blood vessel (hematoma), arteriovenous fistulas (passages between the arterial and venous systems of blood vessels) and retroperitoneal hematomas can also arise. Neighboring nerves can also become compressed or traumatized from direct pressure or profuse bleeding, resulting in pain, sensation disturbances or even paralysis of the groups of muscles which are innervated by these nerves. These complications arise in approximately 1-3% of all procedures. Surgical intervention is sometimes necessary whereby the hematoma is relieved and the puncture site is sutured over (and, if required, any fistula is sealed).

Various apparatuses and devices have been suggested and are being used for percutaneously sealing a vascular puncture by occluding or approximating the margins (edges) of the puncture site (These apparatuses and devices should be known to those skilled in the art, all of which need not be specifically referenced herein). These apparatuses and devices relate to closure devices that must be manually deployed via a deployment instrument. See, e.g., U.S. Pat. No. 5,676,689, issued to Kensey et al. With respect to the prior art, the efficacy of vascular closure depends strongly on the user's ability to position the closure means accurately with respect to the puncture site while the procedure is performed blindly. The manual deployment means of such vascular closure devices (characterized by multiple user-performed steps and device manipulations) necessitates the user to develop a highly subjective "feel" or "tactile technique" to reliably position the closure device correctly.

This requirement of tactile manipulation coupled with the many user-induced procedural steps, difficulty of use, long learning curves, and low precision (of the prior art devices) has lead to a slow adoption rate for vascular closure devices among cardiac catheterization laboratories. As a result, the benefits to the patient (comfort and improved medical outcome) and to the institution (enhanced throughput and decreased costs) are compromised.

SUMMARY OF THE INVENTION

It is therefore a principal object and an advantage of the present invention to provide deployment devices or instruments (that are used to deploy closure implants) that offer improved ease-of-use as compared with the current devices (as discussed supra), i.e., that: (1) minimize tactile manipulation, (2) minimize user-induced procedural steps, (3) minimize user training time to learn how to effectively use the deployment devices or instruments, (4) increase closure precision, and (5) increase the typical user's desire to use such deployment devices or instruments. More specifically, it is a principal object and an advantage of the present invention to provide deployment devices or instruments with automated functionality.

It is another object and advantage of the present invention to provide a closure device that provides a better, more effective seal on a repeatable basis, as compared with the first generation closure devices described supra.

It is a further object and advantage of the present invention to provide a closure device that dissolves (biodegrades) in vivo, allowing for future arterial access, i.e. 're-sticks'.

It is another object and advantage of the present invention to provide a closure device that is operable to lock in place, to stabilize the closure implant (the device) across the vessel wall, i.e., where the implant construct compresses the vessel wall and then is held in place (locked) such that it is immovable. One of the risks of bleeding in existing devices is that they don't provide a closure construct which is resistant to dislodgement due to physiologic motion (hip flexion, etc.). Hence, a locked (or stable) device in accordance with an embodiment of the present invention would allow for a more secure early ambulation of the patient.

In accordance with the foregoing objects an advantages, an embodiment of the present invention provides medical devices and methods for sealing and closing passages formed through tissue that overcome the problems of the prior art. More specifically, devices for sealing or closing an opening formed through biological tissue comprising a distal or outside margin or surface, and a proximal or inside margin or surface (i.e., a wall thickness), and apparatuses and methods for delivering such devices, to control (or prevent or stop) bleeding (or the flow of other biological fluid or tissue), are provided. The openings comprise punctures, incisions, or other openings formed through biological tissue such as blood vessels or organs.

In accordance with an embodiment of the present invention, a closure device is provided for sealing openings formed through biological tissue of various sizes (e.g., openings formed as a result of small percutanous puncture procedures such as diagnostic catheterization or coronary angioplasty or stenting, and openings formed as a result of large percutaneous puncture procedures such as mitral valve repair techniques).

In accordance with an embodiment of the present invention, a closure device for sealing an opening formed through biological tissue is provided which comprises a footplate, a plug, and a wire in a pre-deployed closure device deployment configuration and position.

In accordance with an embodiment of the present invention, a closure device for sealing an opening formed through biological tissue is provided which comprises a footplate, a plug, and a wire in a post-deployed closure device deployment configuration and position.

In accordance with an embodiment of the present invention, the footplate comprises a monolithic structure, i.e., fabricated as a single structure (wire form) comprising a distal portion of the wire. The distal portion of the wire that comprises the footplate comprises a looped or elliptically shaped distal portion of the wire. The monolithic embodiment of the footplate is operable to plastically deform.

In accordance with an embodiment of the present invention, the footplate comprises a structure which is separate from and permanently fixed to the wire. The footplate portion comprises a stamped or machined plate portion. In this embodiment, a portion, preferably a distal portion, of the wire can be welded to the footplate. This welded embodiment of the footplate is operable to plastically deform. Alternatively, a portion, preferably a distal portion, of the wire is attached to the footplate either by a ball-and-socket mechanism/configuration, or hingedly attached to the footplate by a hinge mechanism.

In accordance with an embodiment of the present invention, the footplate is separate from and may be hingedly attached to the wire, such as the ball-and-socket mechanism mentioned supra.

In accordance with an embodiment of the present invention, the wire is attached to the footplate by a ball-and-socket configuration whereby the ball is integral to, and coaxial with, the wire, and whereby the diameter of the ball (sphere) is greater than the diameter of the wire. Further, whereby the ball is co-located with the distal end of the wire. The ball may be formed on the distal end of the wire by a method such as melting (making the wire material molten to flow into a ball, or spherical shape and then allowing the ball to cool and solidify) where the heating source may be, e.g., a laser or an induction-type heating means, or other heating source. Alternatively, the ball-shaped end may be a separate spherically-shaped part (such as a solid sphere with a through-hole) which is attachable to the distal end of the wire by such means as, e.g., crimping, rotary swaging, laser welding, or other acceptable means.

In accordance with an embodiment of the present invention, the footplate and the wire (including a separate spherically-shaped part as the ball-end) comprise a biocompatible and biocorrodible metal.

In accordance with an embodiment of the present invention, the footplate and the wire (including a separate spherically-shaped ball-end) comprise a biocompatible and biocorrodible metal comprising magnesium.

In accordance with an embodiment of the present invention, the footplate and the wire (including a separate spherically-shaped ball-end) comprise a biocompatible and biocorrodible metal comprising a magnesium alloy (e.g., Mg 9980A, Mg 9990A, Mg 9995A, AM100A, AZ63A, AZ91A, AZ91B, AZ91C, AZ92A, AZ81A, EK30A, EK41A, EZ33A, HK31A, HZ32A, K1A, ZE41A, ZH62A, ZK51A, ZK61A, AZ31B, AZ31C, AZ61A, AZ80A, HM31A, M1A, ZK21A, ZK60A, (P)ZK60B, HM21A, ZE10A, TA54A, WE54, WE43, ZW3, AZM, AZ80, AZ31, ZM21, ZK60, and the like).

In accordance with an embodiment of the present invention, the footplate and the wire (including a separate spherically-shaped ball-end) comprise a biocompatible and biocorrodible metal comprising a magnesium alloy comprising magnesium and a rare earth metal.

In accordance with an embodiment of the present invention, the footplate and the wire (including a separate spherically-shaped ball-end) comprise a biocompatible and biocorrodible metal comprising a magnesium alloy comprising magnesium and at least one rare earth metal, wherein the rare earth metal is selected from the group consisting of scandium, lanthanum, cerium, praseodymium, neodymium, promethium, samarium, europium, gadolinium, terbium, dysprosium, holmium, erbium, thulium, ytterbium and lutetium, among others.

In accordance with an embodiment of the present invention, the footplate comprises a bioabsorbable polymer and the wire (including a separate spherically-shaped ball-end) comprises a biocompatible and biocorrodible metal, including the biocompatible and biocorrodible metals discussed supra.

In accordance with an embodiment of the present invention, the footplate comprises a bioabsorbable polymer (e.g., Poly-L-Lactic Acid (PLLA), Poly-Lactic-Co-Glycolic Acid (PLGA), and Poly-Glycolic Acid (PGA), and the like), and the wire may comprise a biocompatible and biocorrodible metal as disclosed supra.

In accordance with an embodiment of the present invention, the footplate may comprise a biocompatible and biocorrodible metal and the wire may comprise a bioabsorbable polymer, including the biocompatible and biocorrodible metals and bioabsorbable polymers as disclosed supra.

Embodiments of the footplate can be fabricated by using a number of manufacturing techniques. These include, but are not limited to, molding, extruding, machining, stamping, casting, forging, laser cutting and/or processing, laminating, adhesively fixing, welding, combinations thereof, among others, with effectiveness, as needed or desired.

In accordance with an embodiment of the present invention, the wire comprises a tensile element.

In accordance with an embodiment of the present invention, the wire comprises a tensile element, wherein the tensile element comprises a multifilament.

In accordance with an embodiment of the present invention, the wire comprises a tensile element, wherein the tensile element comprises a multifilament, wherein the multifilament comprises a multifilament braided section.

In accordance with an embodiment of the present invention, the wire comprises a tensile element, wherein the tensile element comprises a monofilament.

In accordance with an embodiment of the present invention, the footplate and the wire may both comprise a bioabsorbable polymer, including the bioabsorbable polymers as disclosed supra.

In accordance with an embodiment of the present invention, the plug comprises a bioabsorbable polymer, including the bioabsorbable polymers as disclosed supra.

In accordance with an embodiment of the present invention, the plug comprises a biocompatible and biocorrodible metal, including the biocompatible and biocorrodible metals as disclosed supra.

In accordance with an embodiment of the present invention, the plug is conically-shaped and comprises a distal portion and a proximal portion, wherein a diameter of the plug's distal portion is smaller than a diameter of the plug's proximal portion.

Embodiments of the plug can be fabricated by using a number of manufacturing techniques. These include, but are not limited to, molding, extruding, machining, deep drawing, casting, forging, laser cutting and/or processing, laminating, adhesively fixing, welding, combinations thereof, among others, with effectiveness, as needed or desired.

In accordance with an embodiment of the present invention, the closure device is biodegradable.

In accordance with an embodiment of the present invention, the footplate is formulated to biodegrade in vivo at a rate greater than the plug such that the footplate completely degrades prior to the complete degradation of the plug.

In accordance with an embodiment of the present invention, a deployment device or instrument that is easy to use, that minimizes the need for tactile manipulation, provides for a minimal number of user-induced procedural steps, requires a minimal amount of user training time ("short learning curve") to learn how to effectively use the deployment device or instrument, and which has high precision, all of which leads to an increase in the typical user's desire to use such a deployment device or instrument, is provided. More specifically, in accordance with an embodiment of the present invention, a deployment device or instrument with automated functionality for deploying closure devices of an embodiment of the present invention is provided.

In accordance with an embodiment of the present invention, a deployment device or instrument that utilizes a housing, at least one first bias or elastic member (e.g., coil spring, leaf spring, constant force spring, or other member or mechanism capable of storing and releasing kinetic energy), a first moveable/slidable element, and a first release mechanism (e.g., pin release, hook-and-shoulder release, cam-action release, toggle release, or other mechanism capable of releasing a component or components under a spring load), is provided.

In accordance with an embodiment of the present invention, a deployment device or instrument that utilizes a housing, at least one second bias or elastic member (e.g., coil spring, leaf spring, constant force spring, or other member or mechanism capable of storing and releasing kinetic energy), a second moveable/slidable element, and a second release mechanism (e.g., pin release, hook-and-shoulder release, toggle release, or other mechanism capable of releasing a component or components under a spring load), is provided.

In accordance with an embodiment of the present invention, a deployment device or instrument manufactured primarily of thermoplastic parts is provided, which is disposable immediately after the vascular closure device of an embodiment of the present invention has been deployed. The deployment device of an embodiment of the present invention manufactured primarily of thermoplastic parts can offer a cost effective means (via inexpensive materials) to close an opening formed in biological tissue.

In accordance with an embodiment of the present invention, a system for sealing an opening formed through biological tissue (such as a percutaneously formed puncture comprising an opening formed in a wall of a blood vessel) comprising a closure device for sealing the opening and a deployment device for deploying the closure device into the opening to seal the opening, to control (or prevent or stop) bleeding (or the flow of other biological fluid or tissue), is provided. The percutaneously formed puncture further comprises a tissue tract contiguous with the opening formed in the wall of the blood vessel, which extends through the tissue to the surface of the skin overlying the blood vessel. The closure device comprises a plug, a wire, and a footplate, as described supra. The deployment device comprises: distal C-tubes comprising an outer distal C-tube and an inner distal C-tube housed within the outer distal C-tube, a skin flange assembly (a portion of which is coaxial with the longitudinal axis of the wire), a housing shell, a control housing, proximal tubes comprising an outer proximal tube and an inner proximal tube, a push tube, a slide barrel assembly comprising a slide barrel and a cut-off lever, a bias member comprising a plurality of lateral constant force springs, a second bias member comprising an upper constant force spring and a lower constant force spring, a wire ferrule comprising an elongated U-shaped structure wherein the U-shaped structure comprises a closed proximal end and an open distal end, and a squeeze lever handle assembly comprising a squeeze lever handle, a button held within a retainer portion of the squeeze lever handle, wherein the button is slidable within the retainer portion, and a link.

In accordance with an embodiment of the present invention, in a pre-deployed closure device deployment configuration and position, the footplate resides within the distal end of the outer distal C-tube. The proximal end of the footplate abuts the distal end of the inner distal C-tube. The plug is proximal to the footplate, and resides along the longitudinal axis of the wire within the distal portion of the outer proximal tube and is distally adjacent to the push tube. The wire extends proximally from the proximal end of the footplate through the inner distal C-tube, through an axial hole in the plug, and through the push tube, and attaches to an inner portion of the proximal closed end of the wire ferrule.

In accordance with an embodiment of the present invention, the distal C-tubes are concentrically nested together forming a main conduit area therethrough. The main conduit area is operable to serve as a blood marking passageway. The outer distal C-tube and an inner distal C-tube each comprise a side hole which are concentrically lined up with one another and are operable to serve as an atmospheric exit for proximal blood flow from the blood vessel through the blood marking passageway. The outer distal C-tube includes an inlet hole towards the outer distal C-tube's distal end. This inlet hole serves as an entrance to the blood marking passageway and is preferably located towards the proximal end of the footplate's pre-deployed closure device deployment position. This allows for an indication that the entire footplate is within the blood vessel. The proximal blood flow through the blood marking passageway is due to a lower pressure at the atmospheric exit than at the inlet hole.

In accordance with an embodiment of the present invention, the main conduit area is operable to serve as a deployment area for deploying the plug. The distal C-tubes are operable to locally expand and disassociate creating an irreversible un-nested condition to allow passage of the plug into the post-vascular deployment configuration and position, wherein the plug comprises a proximal diameter which is larger than an inner diameter of the main conduit area.

In accordance with an embodiment of the present invention, the distal C-tubes are operable to independently slide coaxially with the longitudinal axis of the wire.

In accordance with an embodiment of the present invention, the deployment device further comprises a guide wire lumen comprising a proximal guide wire exit and a distal guide wire entrance for insertion of a guide wire. Upon insertion of the guide wire, the guide wire extends percutaneously in a proximal direction from the lumen of a blood vessel through the percutaneously formed puncture and to the distal guide wire entrance. From the distal guide wire entrance, the guide wire extends proximally through the guide wire lumen to the proximal guide wire exit wherein the guide wire proximally exits from the guide wire lumen.

In accordance with an embodiment of the present invention, the skin flange assembly comprises a distal end and a proximal end, and is operable to distally slide along the longitudinal axis of the control housing. The proximal portion slides along the outside portion of the control housing and the distal portion slides along the outside portion of the distal C-tubes.

In accordance with an embodiment of the present invention, the control housing is partially housed by the skin flange assembly.

In accordance with an embodiment of the present invention, the proximal tubes are housed within the control housing and are operable to independently slide along the longitudinal axis of the wire.

In accordance with an embodiment of the present invention, the slide barrel is generally distal to the position where the proximal portion of the wire attaches to the wire ferrule within the control housing. The slide barrel assembly is operable to distally slide along the longitudinal axis of the wire.

In accordance with an embodiment of the present invention, the push tube is operable to push the plug into a post-deployed closure device deployment configuration and position. The push tube resides within the proximal tubes. A distal end of the push tube is adjacent to the plug. (Alternatively, the distal end of the push tube can be adjacent to an insert, which is adjacent to the plug). A proximal end of the push tube partially stretches through the slide barrel assembly, is distal to a proximal portion of a slide barrel assembly, and is underneath a cut-off lever. The proximal end of the push tube can be nested within an alignment key. The push tube is operable to distally slide along the longitudinal axis of the wire, and is operable to push the plug through the main conduit area.

In accordance with an embodiment of the present invention, the cut-off lever comprises a proximal portion that is hingedly attached by a hinge pin mechanism to the slide barrel. The cut-off lever is operable to move (hingedly movable) about the hinge pin mechanism in a perpendicular direction such that its distal end rotates up and away from the longitudinal axis of the wire.

In accordance with an embodiment of the present invention, the lateral constant force springs reside partially within the skin flange assembly and comprise a left lateral constant force spring and a right lateral constant force spring. The left lateral constant force spring and the right lateral constant force spring each comprises a flat portion and a roll spring portion. The roll spring portions of the lateral constant force springs reside at a lateral outside distal portion of the control housing (within the distal end of the skin flange assembly). A proximal end of the flat portion of the left lateral constant force spring resides within the left inside proximal portion of the skin flange assembly and is attached to the inside proximal portion of the skin flange assembly by an acceptable attachment means (e.g., screw), and extends distally along a left outside portion of the control housing to the roll spring portion of the left lateral constant force spring. A proximal end of the flat portion of the right lateral constant force spring resides within the right inside proximal portion of the skin flange assembly and is attached to the inside proximal portion of the skin flange assembly by an acceptable attachment means (e.g., screw), and extends distally along a right outside portion of the control housing to the roll spring portion of the right lateral constant force spring.

In accordance with an embodiment of the present invention, the lateral constant force springs are operable to move the skin flange portion in a distal direction by a constant distal force.

In accordance with an embodiment of the present invention, the lateral constant force springs are operable to apply a constant distal force to an outside surface of the skin, just proximal to the percutaneous puncture.

In accordance with an embodiment of the present invention, the lateral constant force springs are operable to apply a constant tensile proximal force to the wire wherein the constant tensile proximal force seats the footplate against an inside wall of the blood vessel. A datum is created at a point where the footplate is seated.

In accordance with an embodiment of the present invention, the deployment device further comprises a rotary damping system partially residing within the skin flange assembly and along an outside portion of the control housing. The rotary damping system is operable to partially resist, and not fully negate, the constant distal force created by the lateral constant force springs on the skin flange assembly.

In accordance with an embodiment of the present invention, the upper and lower constant force springs partially reside within the skin flange assembly, wherein the upper constant force spring and lower constant force spring each comprises a flat portion and a roll spring portion. A proximal end of the lower flat spring portion of the lower constant force spring is attached (by an acceptable fastening means, e.g., a screw) to a lower portion of the slide barrel, and distally extends along a lower outside portion of the control housing to the lower roll spring portion. The lower roll spring portion resides at a lower distal outside portion of the control housing (within the distal portion of the skin flange assembly). A proximal end of the upper flat spring portion of the upper constant force spring is attached (by an acceptable fastening means, e.g., a screw) to an upper portion of the slide barrel, and distally extends along an upper outside portion of the control housing to the upper roll spring portion. The upper roll spring portion resides at an upper distal outside portion of the control housing (within the distal portion of the skin flange assembly).

In accordance with an embodiment of the present invention, the upper constant force spring and the lower constant force spring are operable to move the slide barrel assembly in a distal direction by a constant distal force. The slide barrel assembly is operable to push the push tube in a distal direction by the constant distal force applied by the upper and lower constant force springs to the slide barrel. The plug is pushed percutaneously into the percutaneous puncture and into a post-deployed closure device deployment configuration and position (e.g., within the opening formed in the wall of the blood vessel), wherein the post-vascular closure device deployment position is controlled by the creation of the datum with the wire and the footplate in order to seal the opening formed in the wall of the blood vessel. Thus, this opening through biological tissue (e.g., formed in the wall of the blood vessel) comprising a distal or outside margin or surface, and a proximal or inside margin or surface (i.e., a wall thickness), provides a "platform" for which the closure device of an embodiment of the present invention is useful.

In accordance with an embodiment of the present invention, the wire ferrule resides within the proximal tubes and is operable to longitudinally slide along the longitudinal axis of the control housing.

In accordance with an embodiment of the present invention, the squeeze lever handle of the squeeze lever handle assembly is removably attached to the proximal end of the skin flange assembly by lateral upper hook-shaped ends. The lateral upper hook-shaped ends comprise a left upper hook-shaped end and a right upper hook-shaped end. The link of the squeeze lever handle assembly comprises an upper hook-shaped portion and a lower portion. The upper hook-shaped portion of the link is removably attachable to a lower hinge pin mechanism of the slide barrel and the lower portion of the link is attached to the squeeze lever handle by a hinge pin mechanism.

The deployment device can be formed from a number of suitably durable materials. In one embodiment, the deployment device is formed from a combination of suitable plastic (such as thermoplastic), and metal. In modified embodiments, other suitable plastics, metals, alloys, ceramics, or combinations thereof, among others, may be effectively utilized, as needed or desired. Suitable surface coatings or finishes may be applied, as required or desired.

Embodiments of the deployment device can be fabricated by using a number of manufacturing techniques. These include, but are not limited to; molding, extruding, machining, stamping, casting, forging, laser cutting and/or processing, laminating, adhesively fixing, welding, combinations thereof, among others, with effectiveness, as needed or desired.

In accordance with an embodiment of the present invention, a method of actuating a deployment device for purposes of automatically deploying a closure device is provided. The method employs a user-induced first squeezing action which creates automatic actuation of a first release mechanism (e.g., a hook-and-shoulder release) and simultaneously, at least one first elastic member is allowed to impart kinetic energy on a first moveable/slidable element.

In accordance with an embodiment of the present invention, a method of actuating a deployment device for purposes of automatically deploying a closure device is provided. The method employs a second user-induced squeezing action which creates automatic actuation of a second release mechanism (e.g., a hook-and-shoulder release) and simultaneously, at least one second elastic member is allowed to impart kinetic energy on a second movable/slidable element.

In accordance with an embodiment of the present invention, a method of deploying a closure device of an embodiment of the present invention to control (or prevent or stop) bleeding (or the flow of other biological fluid or tissue) by sealing or closing openings formed through biological tissue such as percutaneously formed punctures, incisions, or other openings, such as in blood vessels (e.g., an artery such as the femoral artery), organs, and the like, is provided. For example, this method can be performed at the conclusion of a diagnostic or therapeutic intravascular surgical procedure.

In accordance with an embodiment of the present invention, a closure device for sealing an opening formed through biological tissue comprising a plug, a rigid wire comprising a plastically deformable portion configurable between an unrestrained position and a restrained position relative to the plug, and a footplate attached to the wire is provided.

At least one of the plug, wire, and footplate can be at least partially formed of a biocorrodible metal. The biocorrodible metal can comprise magnesium or a magnesium alloy. The magnesium alloy can comprise AZ31.

The plug of the closure device can comprise a first portion having a first dimension and a second portion having a second dimension that is greater than the first dimension. The footplate can be positioned distally to the first portion of the plug and the deformable portion can be positioned proximally to the second portion of the plug.

The plug can comprise a distal surface and a proximal surface, wherein an area of the plug's distal surface is smaller than an area of the plug's proximal surface. The wire of the closure device can be in the restrained position, and contain a plastically deformed bend that is positioned in secure engagement with the proximal surface of the plug. The wire can comprise a longitudinal axis, and the plastically deformed bend can be bent at about a 30 to 90 degree angle from the longitudinal axis.

The plug can also be substantially t-shaped, substantially conically-shaped, or substantially bugle-shaped. The plug can include a passageway through which the wire extends, and the plug can be movable along the wire.

The footplate of the closure device can be a substantially looped distal portion of the wire. The footplate can comprise an elongated plate portion attached to a distal end of the wire, and an aperture formed therethrough. The footplate can comprise an elongated plate portion comprising a socket, wherein a distal end of the wire is captured by the socket. The distal end of the wire can be substantially spherically shaped. The footplate can comprise a longitudinally shaped plate portion that is hingedly attached to the distal end of the wire.

The wire of the closure device can be a tensile element selected from the group consisting of a monofilament and a multifilament.

The footplate and plug can be biodegradable. The footplate can be operable, or adapted, to biodegrade at a rate greater than that of the plug, such that the footplate completely biodegrades prior to the complete biodegradation of the plug.

In accordance with an embodiment of the present invention, a closure device deployment device comprising (a) a housing extending along a longitudinal axis, (b) at least one bias member adapted to exert a bias force, (c) a first sliding member connected to the bias member so that the bias force is applied to the sliding member, and (d) a bias member release mechanism moveable between a first position and a second position so that the first sliding member is constrained with respect to the housing when the bias member release mechanism is in the first position is provided. Also, the bias member release mechanism is moveable between a first position and a second position so that the first sliding member is slidable along the direction of the longitudinal axis when the bias member release mechanism is in the second position, wherein the bias force actuates the first sliding member to slide along the direction of the longitudinal axis when the bias member release mechanism is in the second position. The closure device can be a footplate extending along an elongated plane.

The deployment device can further comprise at least a first distal C-tube interconnected to the elongated housing. The first distal C-tube can comprise a pivot point adapted to actuate the footplate from an elongated planar position parallel to the longitudinal axis to an elongated planar position substantially perpendicular to the longitudinal axis.

The deployment device can further comprise a second distal C-tube interconnected to the housing, wherein the first distal C-tube is concentrically housed within the second distal C-tube forming a main conduit area therethrough. The closure device can comprise a plug, wherein the plug is movable through the main conduit area. The outer distal C-tube can further comprise an elongated guidewire lumen attached thereto. The second distal C-tube can comprise an inlet aperture that is operable, or adapted, to allow biological fluid from the biological tissue to proximally flow into the main conduit area.

Each of the first and second distal C-tubes can comprise an outlet aperture which are concentrically aligned and are operable, or adapted, to serve as an atmospheric exit for the proximal flow of the biological fluid. Each of the inner and outer distal C-tubes can be adapted to locally expand and disassociate from one another to allow the movement of the plug through the main conduit area. Each of the inner and outer distal C-tubes can be adapted to independently coaxially slide along the longitudinal axis.

The at least one bias member can comprise a lateral constant force spring comprising a distal portion and a proximal portion. The first sliding member can comprise a skin flange assembly, wherein the proximal end of the lateral constant force spring is interconnected to the skin flange assembly. The lateral constant force spring can be adapted to displace the skin flange assembly in a distal direction when the bias member release mechanism is in the second position. The skin flange assembly can further comprise at least one proximal portion, wherein at least one proximal portion of the skin flange assembly further comprises a proximal end including the bias member release point, wherein the bias member release point further comprises an undercut portion. The bias member release mechanism can further comprise a handle interconnected to the housing comprising at least one hooked shaped end, the at least one hooked shaped end is configured to selectively engage the undercut portion.

The at least one bias member can comprise a constant force spring comprising a proximal end and a distal end selected from the group consisting of an upper constant force spring and a lower constant force spring. The first sliding member can comprise a slide barrel, wherein the proximal end of the constant force spring is interconnected to the slide barrel. The slide barrel can further comprise a bottom portion including the bias member release point, wherein the bias member release point can further comprise a hinge pin. The bias member release mechanism can further comprise a squeeze lever handle assembly interconnected to the housing comprising a link having a hooked shaped end, the hooked shaped end being configured to selectively disengage from the hinge pin.

In accordance with an embodiment of the present invention, a closure device comprising a rigid plastically deformable wire extending along a longitudinal axis and having a proximal portion and a distal end, a footplate extending along an elongated plane and located at the distal end of the wire pivotable between a first position where the elongated plane is at least substantially parallel to the longitudinal axis and a second position where the elongated plane is not substantially parallel to the longitudinal axis, and a substantially rigid plug adapted to move along the wire from the proximal portion to the distal end to a position adjacent to the footplate in the second position is provided. The footplate can be unitary with the wire, and the footplate and wire can be constructed as separate pieces.

In accordance with an embodiment of the present invention, a closure device for sealing an opening formed through biological tissue comprising a plug, a wire, and a footplate, wherein at least one of the plug, the wire, and the footplate is at least partially formed of a biocorrodible metal, is provided. The biocorrodible metal can comprise magnesium or a magnesium alloy. The magnesium alloy can comprise AZ31. The plug can be at least partially formed of a first magnesium alloy and the footplate can be at least partially formed of a second magnesium alloy, wherein the first magnesium alloy and the second magnesium alloy are different magnesium alloys.

In accordance with an embodiment of the present invention, a closure device for sealing an opening formed through biological tissue comprising a plug, a wire, a footplate, and a connection mechanism adapted to connect the wire and the footplate together. The connection mechanism comprises a substantially spherically shaped ball portion, and a socket portion adapted to capture the ball portion. The ball portion can be connected to the footplate and the socket portion can be connected to the wire. Alternatively, the ball portion can be connected to the wire and the socket portion can be connected to the footplate. The footplate can be rotatable with respect to the wire about at least a first and a second axis. The footplate can be rotatable with respect to the wire about more than two axes.

In accordance with an embodiment of the present invention, a closure device deployment device comprising a housing extending along a longitudinal axis, a first distal C-Tube interconnected to the housing, a second distal C-tube interconnected to the housing, wherein the first distal C-tube is concentrically housed within the second distal C-tube forming a main conduit area therethrough, and each of the first and second distal C-tubes are adapted to independently coaxially slide along the longitudinal axis. The closure device can comprise a plug, wherein the plug is movable through the main conduit area. Each of the inner and outer distal C-tubes can be adapted to locally expand and disassociate from one another to allow the movement of the plug through the main conduit area.

BRIEF DESCRIPTION OF THE DRAWINGS

The present invention will be more fully understood and appreciated by reading the following Detailed Description in conjunction with the accompanying drawings, in which:

FIG. 7a is a partially exposed top side perspective view of the deployment device, according to an embodiment of the present invention.

FIG. 7b is a magnified window view of a portion of the deployment device of FIG. 7a, according to an embodiment of the present invention.

FIG. 7c is a magnified window view of a portion of the deployment device of FIG. 7a, according to an embodiment of the present invention.

FIG. 21a is a right side cross-sectional view of a partially exposed section of the deployment device, according to an embodiment of the present invention.

FIG. 21b is a top side cross-sectional view of a partially exposed section of the deployment device, according to an embodiment of the present invention.

FIGS. 21c and 21d are magnified window views of portions of the deployment device of FIG. 21a, according to an embodiment of the present invention.

FIG. 22a is a right side cross-sectional view of a partially exposed section of the deployment device, according to an embodiment of the present invention.

FIG. 22b is a top side cross-sectional view of a partially exposed section of the deployment device, according to an embodiment of the present invention.

FIGS. 22c and 22d are magnified window views of portions of the deployment device of FIG. 22b, according to embodiments of the present invention.

FIG. 22e is a magnified window view of a portion of the deployment device of FIG. 22a, according to embodiments of the present invention.

FIG. 23a is a right side cross-sectional view of a partially exposed section of the deployment device, according to an embodiment of the present invention.

FIG. 23b is a top side cross-sectional view of a partially exposed section of the deployment device, according to an embodiment of the present invention.

FIGS. 23c and 23d are magnified window views of portions of the deployment device of FIG. 23b, according to embodiments of the present invention.

FIG. 23e is a magnified window view of a portion of the deployment device of FIG. 23a, according to embodiments of the present invention.

FIG. 24a is a right side cross-sectional view of a partially exposed section of the deployment device, according to an embodiment of the present invention.

FIG. 24b is a top side cross-sectional view of a partially exposed section of the deployment device, according to an embodiment of the present invention.

FIGS. 24c-24f are magnified window views of portions of the deployment device of FIG. 24b, according to embodiments of the present invention.

FIG. 25a is a right side cross-sectional view of a partially exposed section of the deployment device, according to an embodiment of the present invention.

FIG. 25b is a top side cross-sectional view of a partially exposed section of the deployment device, according to an embodiment of the present invention.

FIGS. 25c-25d are magnified window views of portions of the deployment device of FIG. 25b, according to embodiments of the present invention.

FIG. 26a is a right side cross-sectional view of a partially exposed section of the deployment device, according to an embodiment of the present invention.

FIG. 26b is a top side cross-sectional view of a partially exposed section of the deployment device, according to an embodiment of the present invention.

FIGS. 26d and 26f are magnified window views of portions of the deployment device of FIG. 26a, according to embodiments of the present invention.

FIG. 26g is a magnified vertical cross-sectional view through a portion of the deployment device of FIG. 26a, according to embodiments of the present invention.

FIGS. 26c and 26e are magnified window views of portions of the deployment device of FIG. 26b, according to embodiments of the present invention.

FIG. 28a is a right side cross-sectional view of a partially exposed section of the deployment device, according to an embodiment of the present invention.

FIG. 28b is an under side perspective view of the deployment device, according to an embodiment of the present invention.

FIG. 29a is a right side cross-sectional view of a partially exposed section of the deployment device, according to an embodiment of the present invention.

FIG. 29b is a top side cross-sectional view of a partially exposed section of the deployment device, according to an embodiment of the present invention.

FIGS. 29d, 29e and 29f are magnified window views of portions of the deployment device of FIG. 29a, according to embodiments of the present invention.

FIG. 29c is a magnified vertical cross-sectional view through a portion of the deployment device of FIG. 29a, according to embodiments of the present invention.

FIG. 30a is a right side cross-sectional view of a partially exposed section of the deployment device, according to an embodiment of the present invention.

FIGS. 30b-30c are magnified window views of portions of the deployment device of FIG. 30a, according to embodiments of the present invention.

DETAILED DESCRIPTION

Figure 1A:
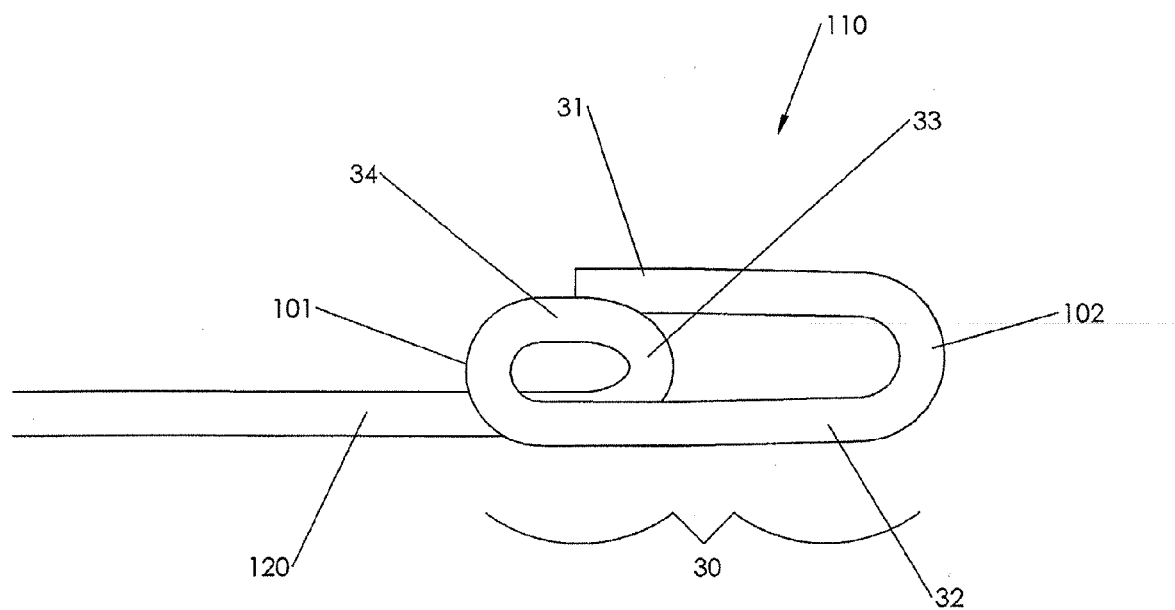
FIGS. 1a-1p are perspective views of footplates according to embodiments of the present invention.

Reference will now be made in detail to the present preferred embodiments of the invention, examples of which are illustrated in the accompanying drawings.

In accordance with an embodiment of the present invention, closure device 100 comprising a footplate 110 (the footplate may include any of the embodiments of the footplate, as discussed infra), a plug 111, and a wire 120 is provided and can be used to seal or close an opening formed through biological tissue, such as a percutaneously formed puncture (the puncture comprises the opening formed through the wall of the blood vessel and a tissue tract contiguous with the opening formed through the biological tissue, which extends through the tissue and to skin overlying the blood vessel), an incision, or some other type of opening formed through biological tissue, such as a blood vessel, organ, or the like, to control (or prevent or stop) bleeding (or the flow of other biological fluid or tissue). For example, the closure device 100 of an embodiment of the present invention can be used to seal an arteriotomy, which is an opening or incision in an artery, such as the femoral artery, and is formed in conjunction with a percutaneously formed puncture (an open tissue tract through the skin and tissue just above the blood vessel) by a clinician during a diagnostic or therapeutic intravascular surgical procedure.

In accordance with an embodiment of the present invention, the closure device 100 may be in a pre-deployed closure device deployment configuration and position or in a post-vascular closure device deployment configuration and position. A pre-deployed closure device deployment configuration and position includes a configuration and position where the closure device 100 resides within a deployment device 200 of an embodiment of the present invention (which is used to deploy the closure device 100 into, e.g., an opening in the wall of a blood vessel, to seal the blood vessel to stop blood from flowing through the opening). A post-deployed closure device deployment configuration and position includes a configuration and position where the closure device 100 resides within and through the opening in the wall of the blood vessel.

The closure device 100, the pre- and post-deployed closure device deployment configurations and positions, the deployment device 200, and the method of deploying the closure device 100 to seal an opening in the wall of a blood vessel, with reference to the figures, is more fully described infra.

Referring now to the drawings where like numbers refer to like parts throughout, FIG. 1a shows a footplate 110 according to an embodiment of the present invention. This embodiment shows a footplate 110 in a pre-deployed closure device deployment configuration and position, wherein the footplate 110 is within a distal end of a deployment device 200 (not shown). The footplate 110 comprises a unitary length of a distal portion of the wire 120 (monolithic structure) bent into an elongated configuration presenting an elongated U-shaped loop 30. The elongated U-shaped loop 30 comprises an open proximal end 101, a closed distal end 102, and a pair of longitudinally laterally spaced extending legs 31, 32. The closed distal end 102 and pair of longitudinally laterally spaced extending legs 31, 32 are substantially coplanar in a common plane and substantially parallel to the longitudinal axis of the control housing 210 of the deployment device 200. The closed distal end 102 of the elongated U-shaped loop 30 defines a longitudinal distal end of the bent wire elongated configuration. The pair of longitudinally-extending laterally spaced legs 31, 32 of the elongated U-shaped loop comprises a free leg 31, having a free proximal end located at the open proximal end of the elongated U-shaped loop 101, and a connecting leg 32. A helically shaped connecting portion 33 connects to the wire 120. The helically shaped connecting portion 33 is operable to permanently (plastically) deform at a bending region. The wire 120 is axial to a longitudinal axis of the control housing 210. The wire 120 is proximal to the footplate 110, and the helically shaped connecting portion 33 extends between a joining leg 34 (which is substantially coplanar with the longitudinally-extending laterally spaced legs 31, 32) and the wire 120 at the open proximal end 101 of the elongated U-shaped loop 30.

Figure 1B:
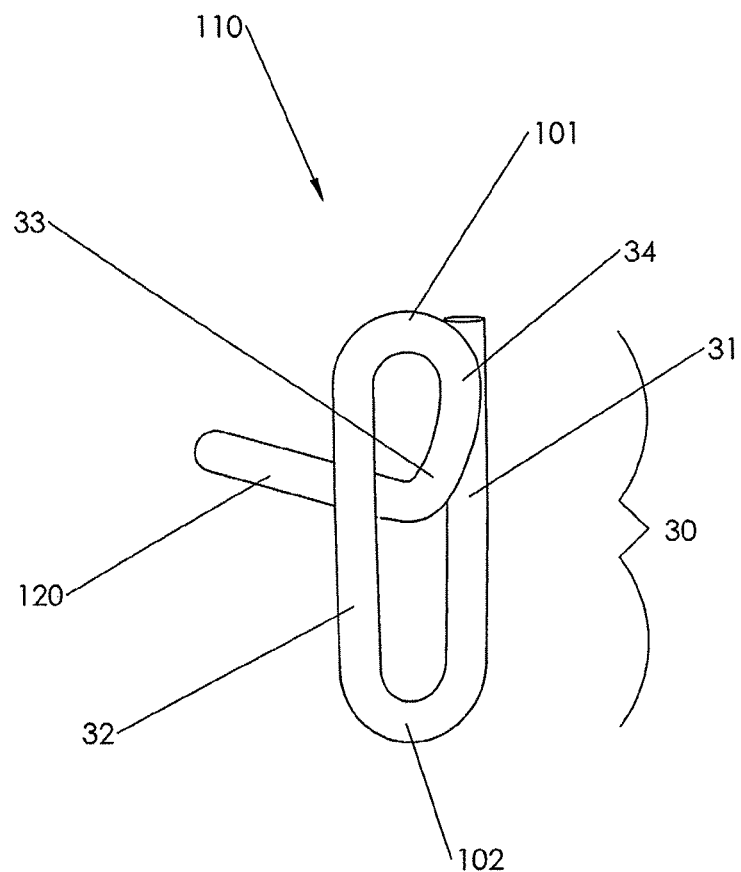

Turning to FIG. 1b, the footplate 110 according to an embodiment of the present invention is illustrated. This embodiment shows the footplate 110 (of FIG. 1a) in a post-deployed closure device deployment configuration and position, wherein a portion of the footplate 110 is seated against an inside wall of a blood vessel (e.g., an artery, not shown) under a percutaneous puncture therein (not shown). The helically shaped connecting portion 33 comprises a bending region, wherein the bending region is permanently (plastically) deformed. The closed end 102 and pair of longitudinally laterally spaced extending legs 31, 32 remain substantially coplanar in a common plane, and are substantially perpendicular to a longitudinal axis of the puncture and substantially parallel to a plane of the inside wall of the blood vessel. The wire 120 extends proximally from the helically shaped connecting portion 33 through the opening in the wall of the blood vessel to the tissue tract wherein the wire 120 is axial to the longitudinal axis of the puncture (prior to being cut and bent by the deployment device 200).

Figure 1C:
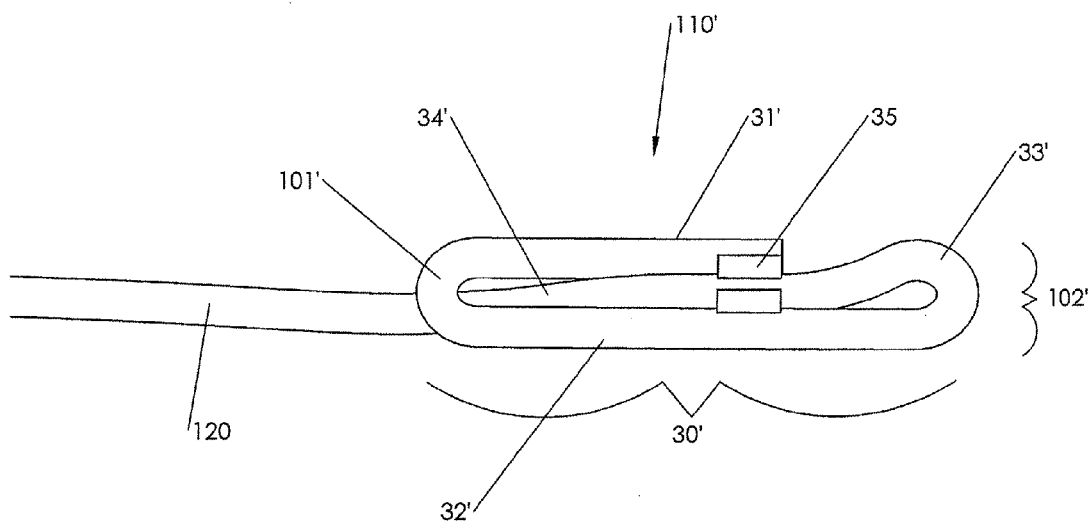

Turning to FIG. 1c, a footplate according to an embodiment of the present invention is illustrated. This embodiment shows a footplate 110' in a pre-deployed closure device deployment configuration and position, wherein the footplate 110' is within the distal end of a deployment device 200 (not shown). The footplate 110' comprises a unitary length of a distal portion of the wire 120 (monolithic structure) bent into an elongated configuration presenting an elongated U-shaped loop 30'. The elongated U-shaped loop 30' comprises an open distal end 102', a closed proximal end 101', and a pair of longitudinally laterally spaced extending legs 31', 32'. The closed proximal end 101' of the elongated U-shaped loop 30' defines a longitudinal proximal end of the bent wire elongated configuration. The pair of longitudinally-extending laterally spaced legs of the elongated U-shaped loop 30' comprise a free leg 31' having a free distal end located at the open distal end 102' of the elongated U-shaped loop 30, and a connecting leg 32'. An arcuately-curved connecting portion 33', and a medial leg 34' comprising a bending region are shown. The arcuately-curved connecting portion 33' extends between the connecting leg 32' and the medial leg 34' at the open distal end 102', defining a longitudinal distal end of the bent wire configuration. The elongated U-shaped loop 30' and the arcuately-curved connecting portion 33' are substantially coplanar in a common plane and axial to a longitudinal axis of the control housing 210 of the deployment device 200. The arcuately-curved connecting portion 33' medially curves toward the connecting leg 32' to the medial leg 34', in between the free leg 31' and the connecting leg 32'. Each of the free leg 31' and the connecting leg 32' is secured to a distal portion of the medial leg by a spot weld 35. The spot weld 35 may comprise an electron beam spot weld or a laser spot weld. The distal end of the free leg ends at a point where the free leg is spot welded to the medial leg 34' (but could be longer or shorter). The medial leg 34' extends proximally toward and under (but could extend over) the closed proximal end 101', and extends beyond the closed proximal end 101' at an angle from the common plane to the wire 120, wherein the wire 120 is proximal to the footplate 110'.

Figure 1D:
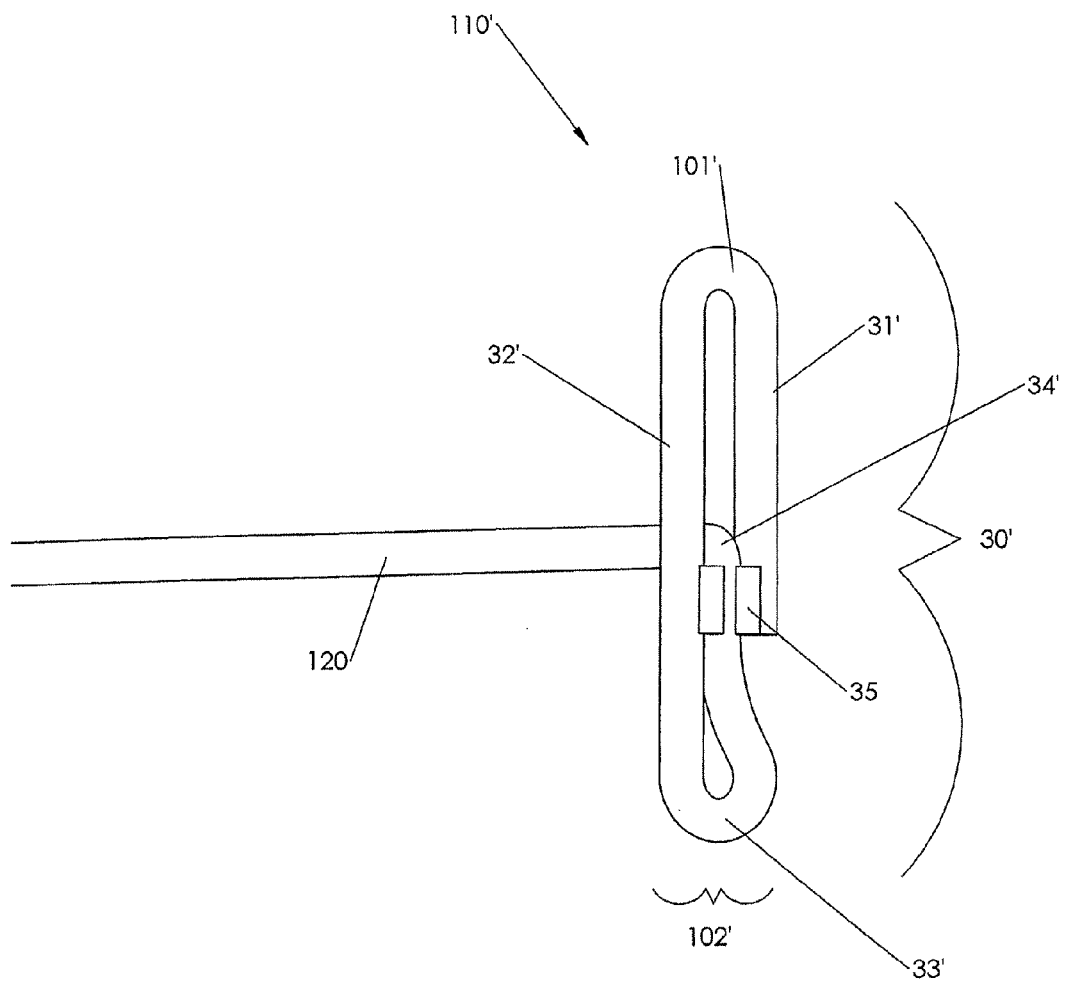

Turning to FIG. 1d, the footplate 110' according to an embodiment of the present invention is illustrated. This embodiment shows the footplate 110' of FIG. 1c in a post-deployed closure device deployment configuration and position, wherein a portion of the footplate 110' is seated against an inside wall of a blood vessel (e.g., an artery, not shown) under a percutaneous puncture therein (not shown). The bending region (preferably at the proximal margin of the spot weld 35 in the medial leg 34') is permanently (plastically) deformed. The elongated U-shaped loop 30' and the arcuately-curved connecting portion 33' remain substantially coplanar in a common plane, and are substantially perpendicular to a longitudinal axis of the puncture and substantially parallel to a plane of the inside wall of the blood vessel. The wire 120 extends proximally from the bending region through the opening in the wall of the blood vessel and inside the tissue tract wherein the wire 120 is axial to the longitudinal axis of the puncture (prior to being cut and bent by the deployment device 200).

Figure 1E:
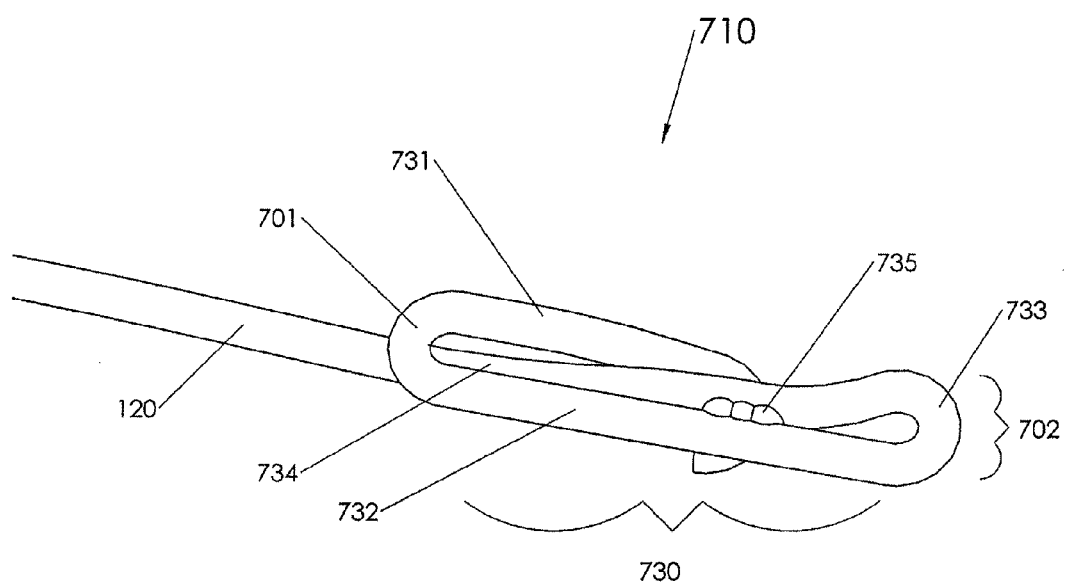
Figure 1F:
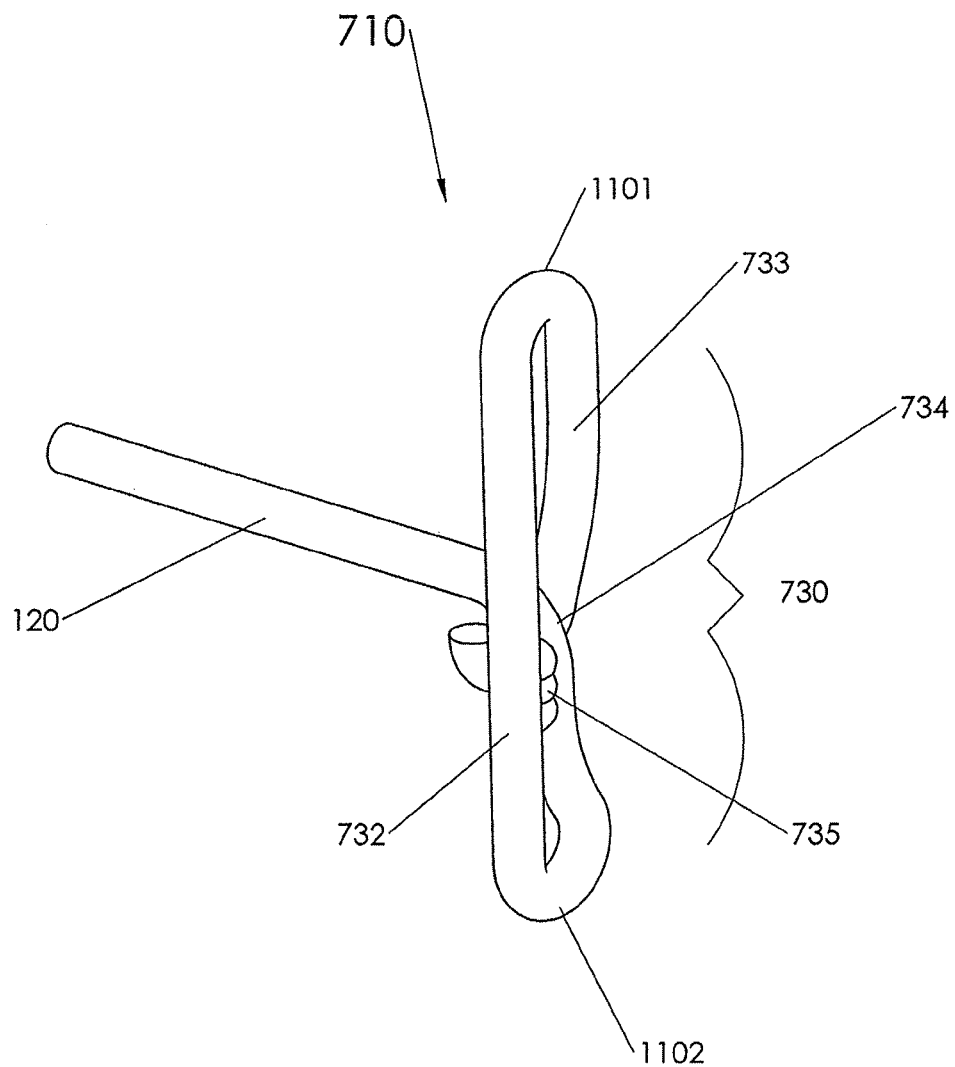

Turning to FIGS. 1e-1f, a footplate 710 according to an embodiment of the present invention is shown. These embodiments of the footplate are similar to the footplates illustrated in FIGS. 1c-1d, respectively, except for free leg 731 and spot weld 735. As shown in FIG. 1e and FIG. 1f, free leg 731 comprises a hooked distal end, and the spot weld 735 only secures medial leg 734 to connecting leg 732. An elongated U-shaped loop 730, a proximal 1101 and distal end 1102, and an arcuately-curved connecting portion 733 are also shown.

Figure 1G:
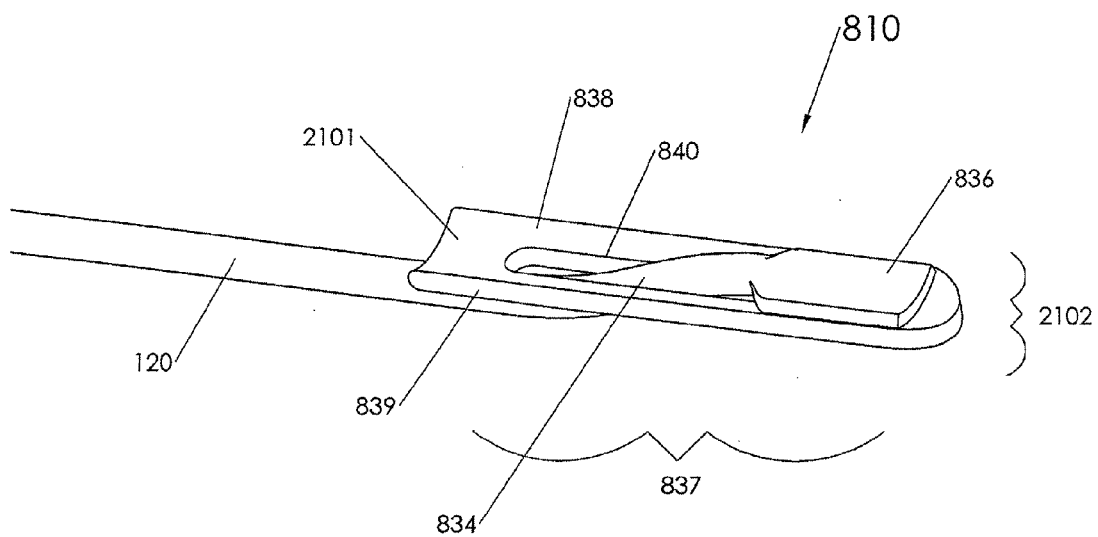

Turning to FIG. 1g, a footplate 810 according to an embodiment of the present invention is shown. This embodiment shows a footplate 810 in a pre-deployed closure device deployment configuration and position, wherein the footplate 810 is within a distal end of a deployment device 200 (not shown). The footplate 810 is a longitudinally shaped block or bar 837. The bar 837 comprises longitudinal aperture 840, a top arcuately-shaped surface 838, a bottom arcuately-shaped surface (not shown) (alternatively, the top and bottom surfaces can be substantially planar), a peripheral side surface 839, a proximal end 2101 and a distal end 2102. The wire 120 is connected to the bar 837 by a flat or coined distal end 836 (preferably welded), which is connected to the distal portion 2102 of the top arcuately-shaped surface 838 of the bar 837 (could also be connected to the bottom arcuately-shaped surface). The coined distal end 836 proximally extends to a medial portion 834, which proximally extends through the aperture 840 and under (but could extend over) the proximal end 2101.

Figure 1H:
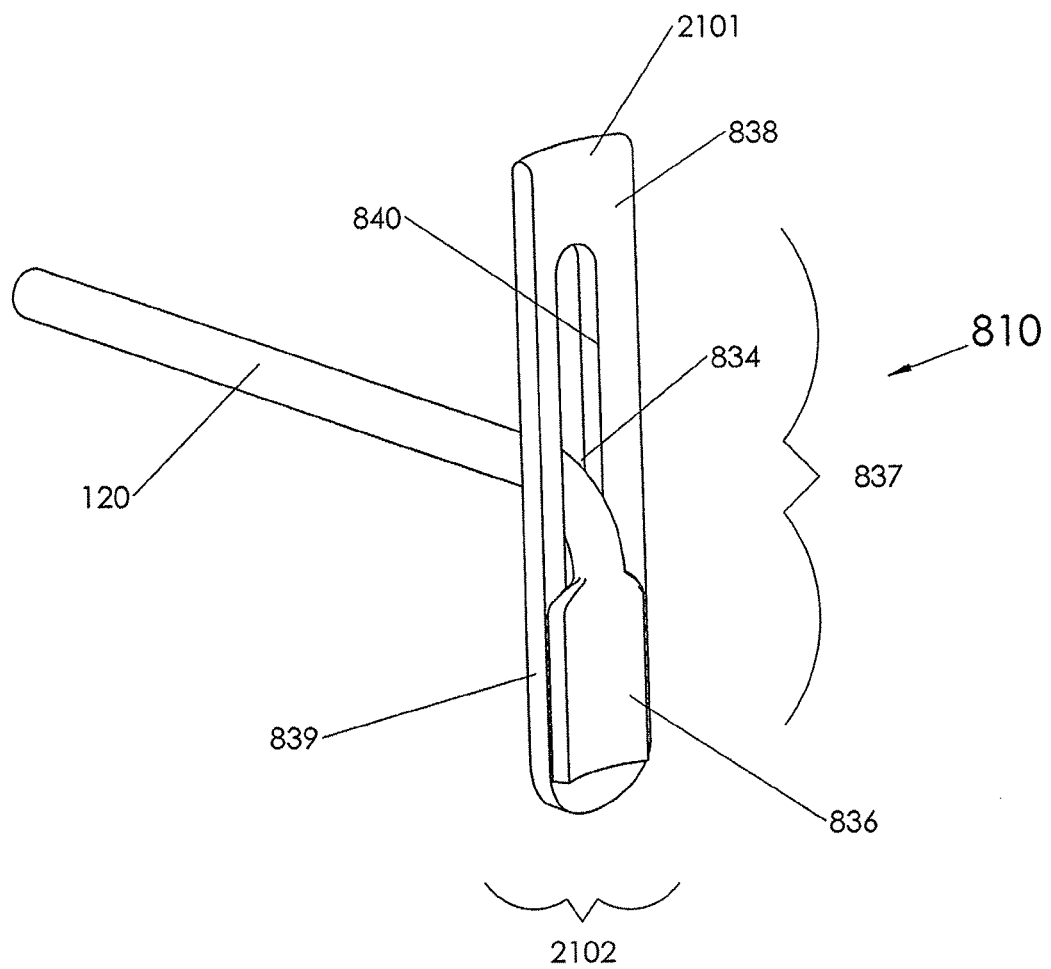

Turning to FIG. 1h, the footplate 810 according to an embodiment of the present invention is illustrated. This embodiment shows the footplate 810 of FIG. 1g in a post-deployed closure device deployment configuration and position, wherein a portion of the footplate 810 is seated against an inside wall of a blood vessel (e.g., an artery, not shown) under a percutaneous puncture therein (not shown). The medial portion 834 comprises a bending region wherein the bending region is permanently (plastically) deformed. The medial portion 834 proximally extends through the aperture 840. The wire 120 extends proximally from the medial portion 834 through the opening in the wall of the blood vessel to the tissue tract, wherein the wire 120 is coaxial to the longitudinal axis of the puncture (not shown) (prior to being cut and bent by the deployment device 200).

Figure 1I:
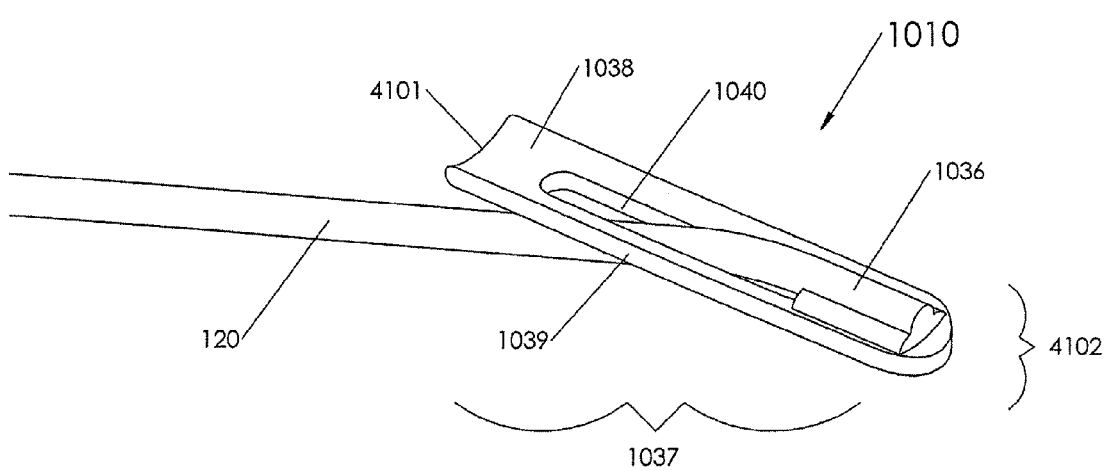
Figure 1J:
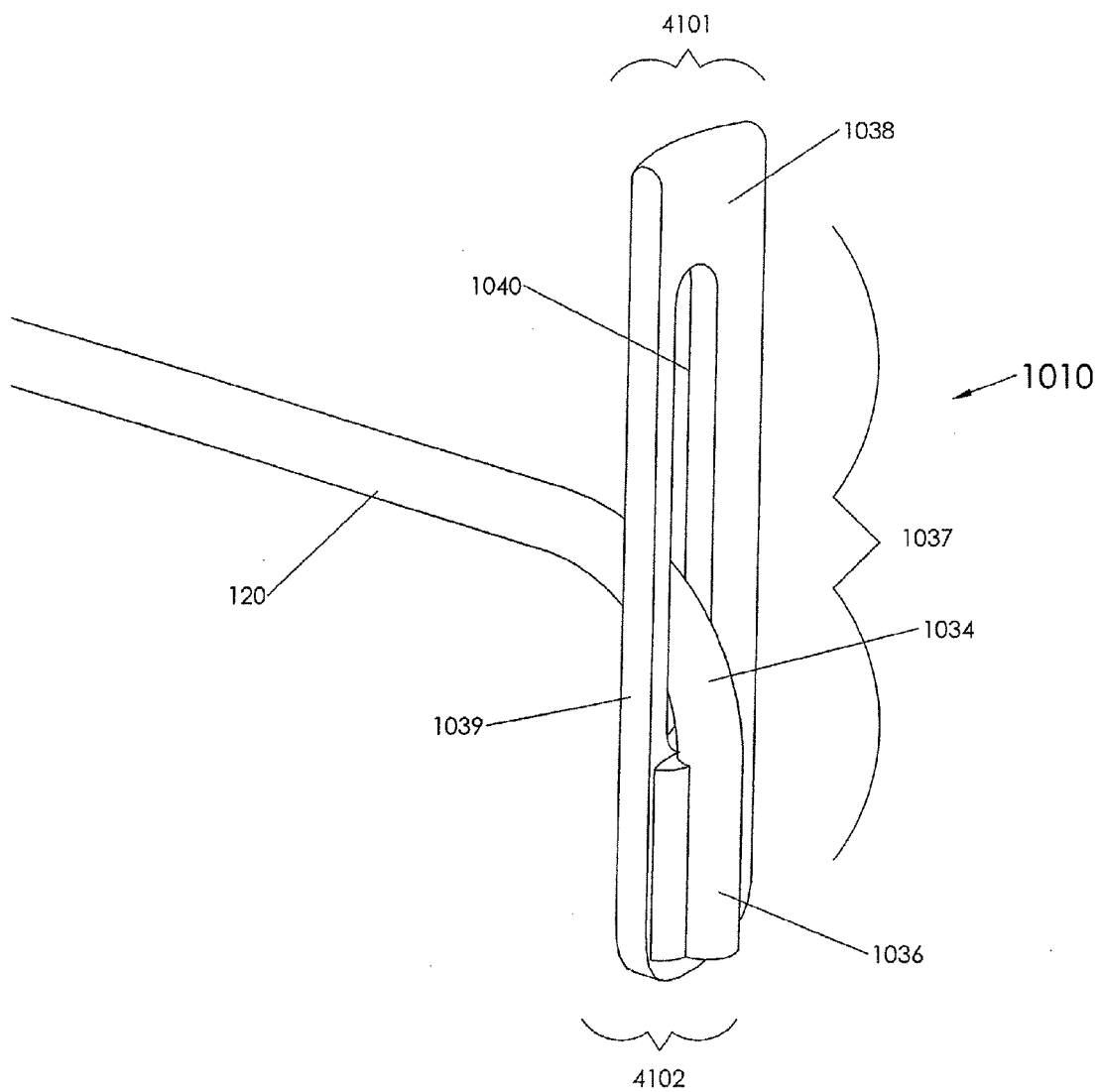

Turning to FIGS. 1i-1j, a footplate 1010 according to an embodiment of the present invention is shown. These embodiments of the footplate are similar to the footplates illustrated in FIGS. 1g-1h, respectively, except for the distal end 1036 of the wire 120. The distal end 1036 is neither flattened nor coined (but is left as the same circular cross-section as the remainder of the wire). The wire 120 is affixed (preferably welded) on both sides along the longitudinal interface between the distal portion of the wire 120 and the arcuately-shaped top surface 1038 at the distal end 4102 of the bar 1037 of the footplate 1010. A proximal end 4101, a medial portion 1034, an aperture 1040, and a peripheral side surface 1039 are also shown.

Figure 1K:
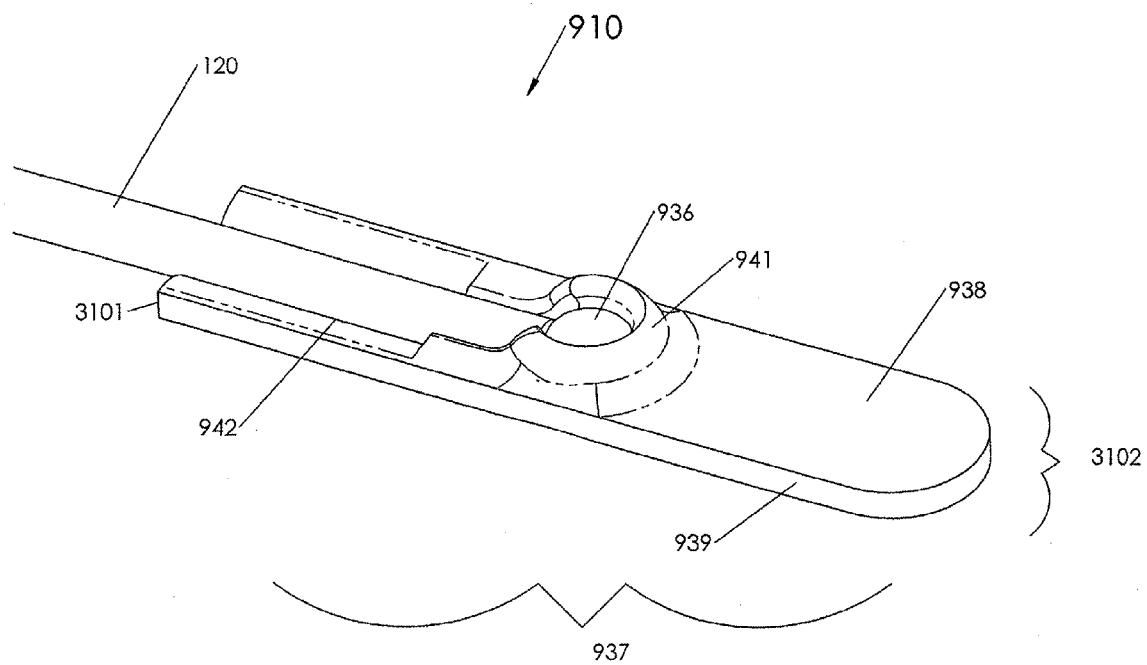
Figure 1L:
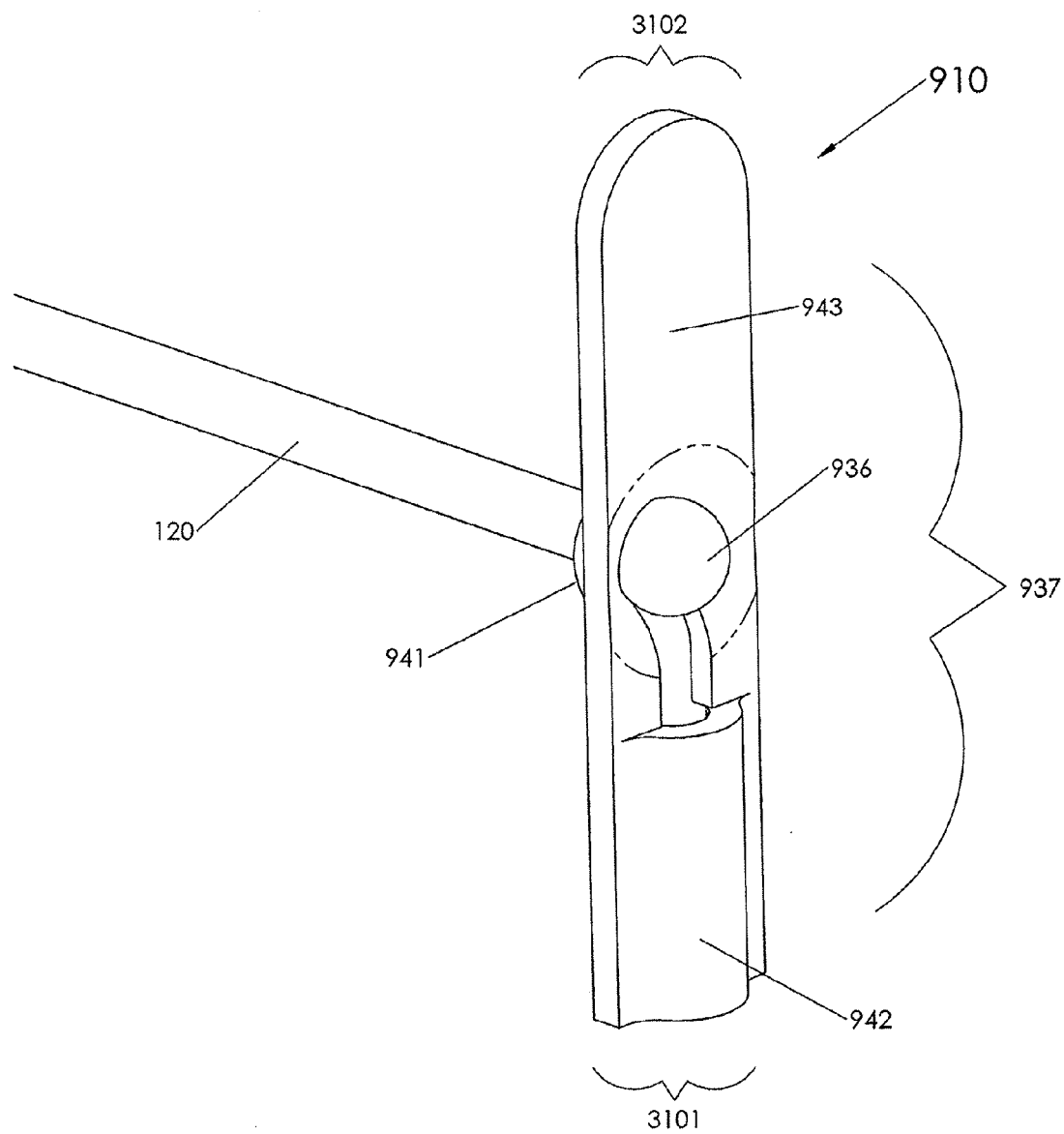

Turning to FIG. 1k, a top perspective view of footplate 910 according to an embodiment of the present invention is shown. This embodiment shows a footplate 910 in a pre-deployed closure device deployment configuration and position, wherein the footplate 910 is within a distal end of a deployment device 200 (not shown). The footplate 910 comprises a longitudinally shaped block or bar 937. The bar 937 comprises a top substantially planar surface 938, a bottom substantially planar surface (not shown), a peripheral side surface 939, a proximal end 3101 and a distal end 3102. The wire 120 is connected to the bar 937 by a ball-shaped end 936, which is connected to a socket 941 of the top planar surface 938 of the bar 937 (could also be connected to the bottom planar surface). The socket 941 is shaped like a "C" to allow for the actuation of the footplate 910, as shown in FIG. 1l. A portion of the wire 120 may sit in an arcuately-shaped depressed section 942 of the top surface 938 of the bar 937.

Turning to FIG. 1l, a bottom perspective view of the footplate 910 according to an embodiment of the present invention is shown. This embodiment shows the footplate 910 of FIG. 1i in a post-deployed closure device deployment configuration and position, wherein a portion of the footplate 910 is seated against an inside wall of a blood vessel (e.g., an artery, not shown) under a percutaneous puncture therein (not shown). There is no bending region in this embodiment of the footplate 910. The bar 937 is operable to rotate pursuant to the ball 936 and socket 941 configuration/mechanism. This establishes a rotation point with the proximal end 3101 rotating down and in the distal direction and the distal end 3102 rotating up (could alternatively rotate in the opposite direction with an alternative configuration) and in the proximal direction about the established rotation point. FIG. 1l shows the footplate 910 in its fully actuated or rotated position. The wire 120 extends proximally from the ball 936 through the opening in the wall of the blood vessel to the tissue tract, wherein the wire 120 is axial to the longitudinal axis of the puncture (not shown) (prior to being cut and bent by the deployment device 200). A bottom substantially planar surface 943 is shown, which may further comprise a protruding section comprising the bottom portion of the depressed section 942 of the top surface 938 of the bar 937.

Figure 1M:
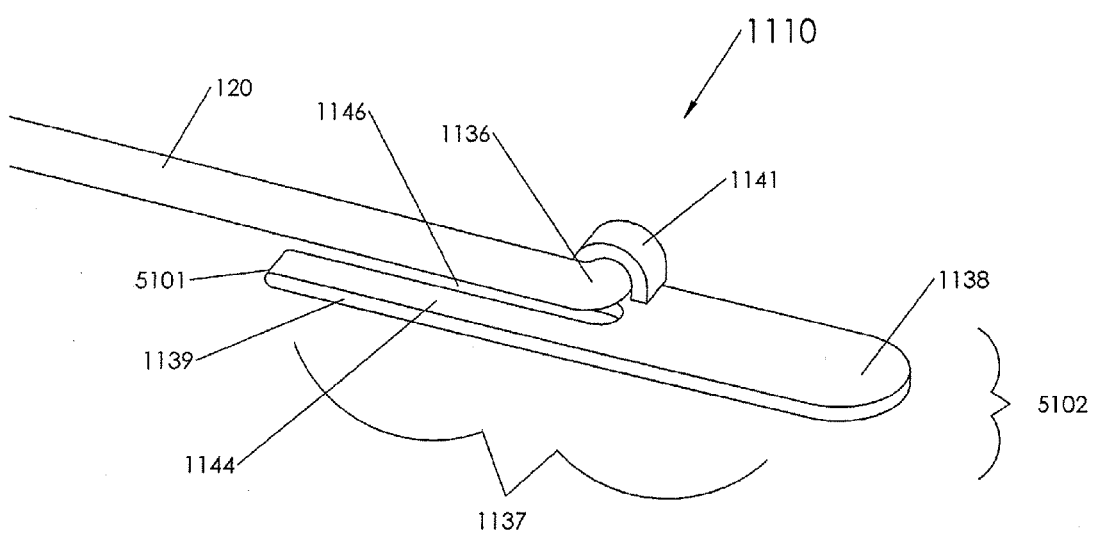

Turning to FIG. 1m, a top perspective view of footplate 1110 according to an embodiment of the present invention is shown. This embodiment shows a footplate 1110 in a pre-deployed closure device deployment configuration and position, wherein the footplate 1110 is within a distal end of a deployment device 200 (not shown). The footplate 1110 comprises a longitudinally shaped block or bar 1137. The bar 1137 is "y-shaped" and comprises a top substantially planar surface 1138, a bottom substantially planar surface 1143 (not shown), a peripheral side surface 1139, a proximal end 5101, a distal end 5102 and two proximally extending substantially coplanar legs 1144 and 1145 (not shown) which are separated by a slot 1146. The wire 120 is connected to the bar 1137 by a hinge mechanism comprising a hooked shaped end 1136, which is connected to a half-circled portion 1141 that is attached to the top substantially planar surface 1138 of the bar 1137 (could also be connected to the bottom planar surface).

Figure 1N:
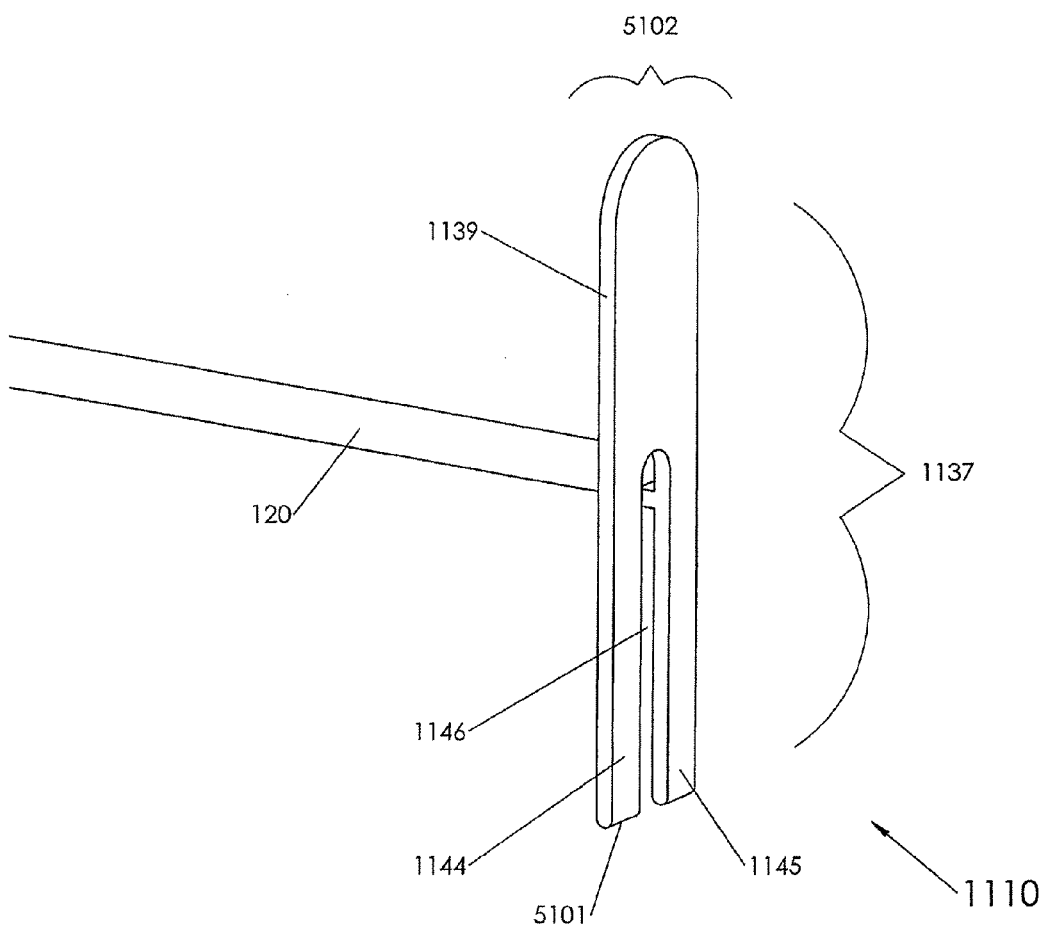

Turning to FIG. 1n, a bottom perspective view of footplate 1110 according to an embodiment of the present invention is shown. This embodiment shows the footplate 1110 of FIG. 1m in a post-deployed closure device deployment configuration and position, wherein a portion of the footplate 1110 is seated against an inside wall of a blood vessel (e.g., an artery, not shown) under a percutaneous puncture therein (not shown). There is no bending region in this embodiment of the footplate 1110. The bar 1137 is operable to rotate pursuant to the hinge mechanism, which establishes a rotation point, with the proximal end 5101 rotating down and in the distal direction and the distal end 5102 rotating up and in the proximal direction, about the established rotation point (could alternatively rotate in the opposite direction with an alternative configuration). FIG. 1n shows the footplate 1110 in its fully actuated or rotated position. The wire 120 extends proximally through the opening in the wall of the blood vessel to the tissue tract, wherein the wire 120 is axial to the longitudinal axis of the puncture (not shown) (prior to being cut and bent by the deployment device 200). A bottom substantially planar surface 1143 is also shown.

Figure 1O:
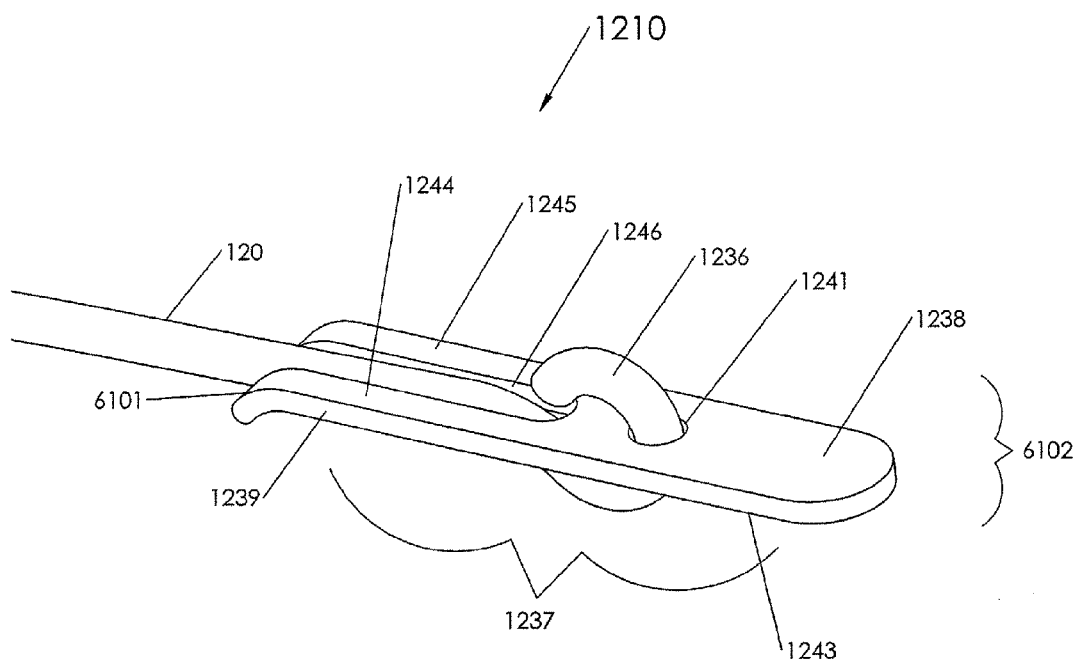
Figure 1P:
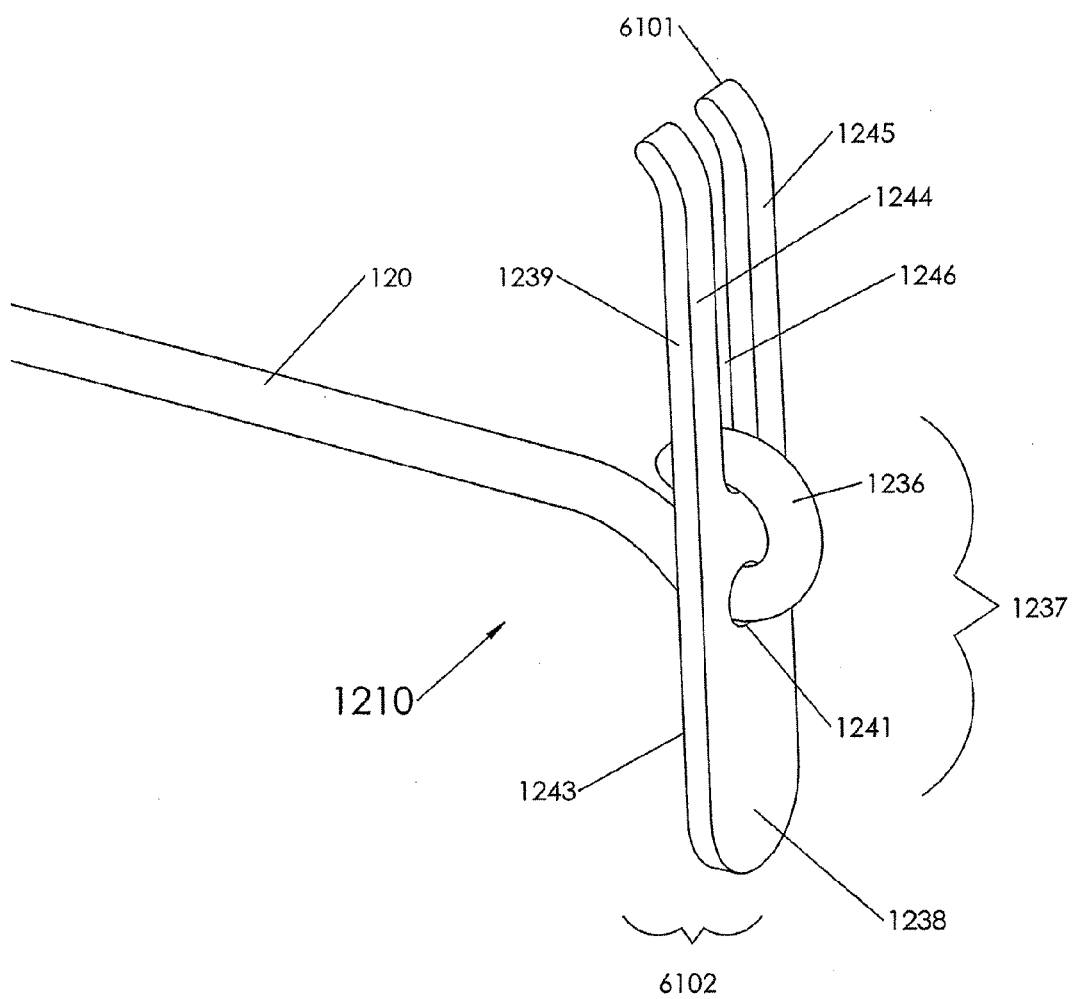

Turning to FIGS. 1o-1p, a footplate 1210 according to an embodiment of the present invention is shown. These embodiments of the footplate are similar to the footplate embodiments illustrated in FIGS. 1m-1n, respectively, except for the hook-shaped distal end 1236 of the wire 120 and its attachment through an aperture 1241 and slot 1246. The hooked-shaped distal end 1236 is attached to the bar 1237 through an aperture 1241. The hooked-shaped distal end 1236 stretches through the aperture 1241 from the bottom substantially planar surface 1243 to the top substantially planar surface 1238, and then hooks through the slot 1246 thereby securing the footplate 1210 to the wire 120. A bar 1237, a distal end 6102 and a proximal end 6101, a top substantially planar surface 1238, a bottom substantially planar surface 1243, a peripheral side surface 1239, two proximally extending substantially coplanar legs 1244 and 1245, a slot 1246, and a wire 120, are also shown.

In accordance with an embodiment of the present invention, the deployment device 200 with the closure device 100 of an embodiment of the present invention is described below with reference to the figures. References regarding the footplate are specifically made to footplate 110', as an example of a footplate that may be used. However, it is to be understood that any footplate embodiment including those referenced supra, may be used in place of footplate 110'.

Figure 2A:
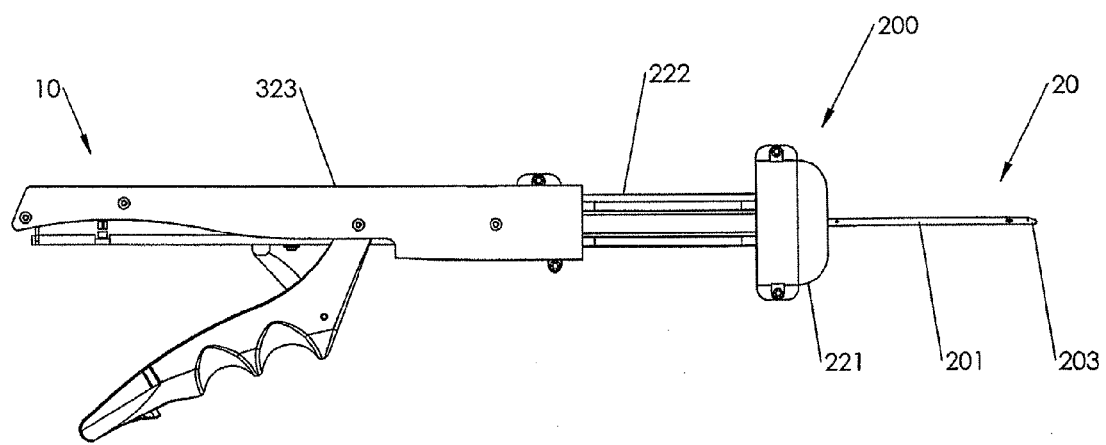
FIG. 2a shows a fully assembled right side perspective view of the deployment device, according to an embodiment of the present invention.
Figure 2B:
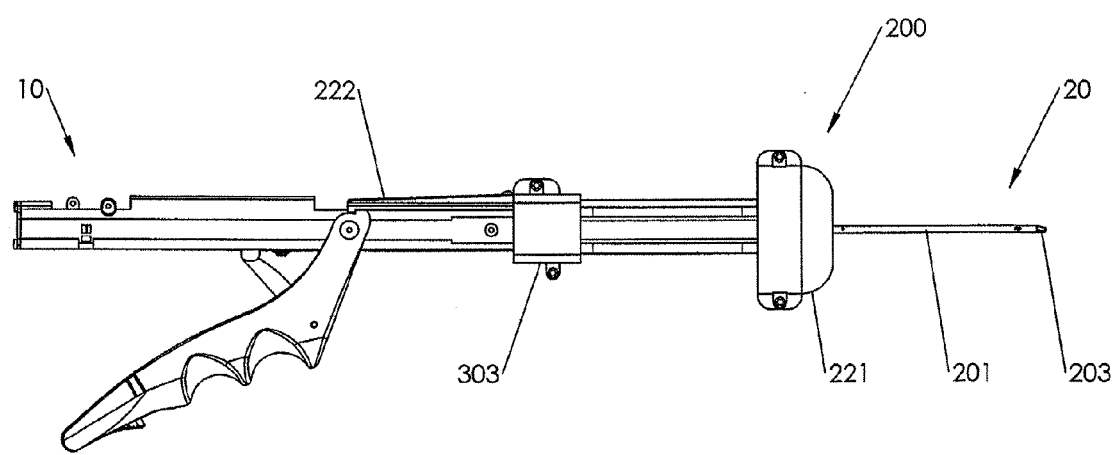
FIG. 2b is a partially exposed right side perspective view of the deployment device, according to an embodiment of the present invention.
Figures 3A, 3B:
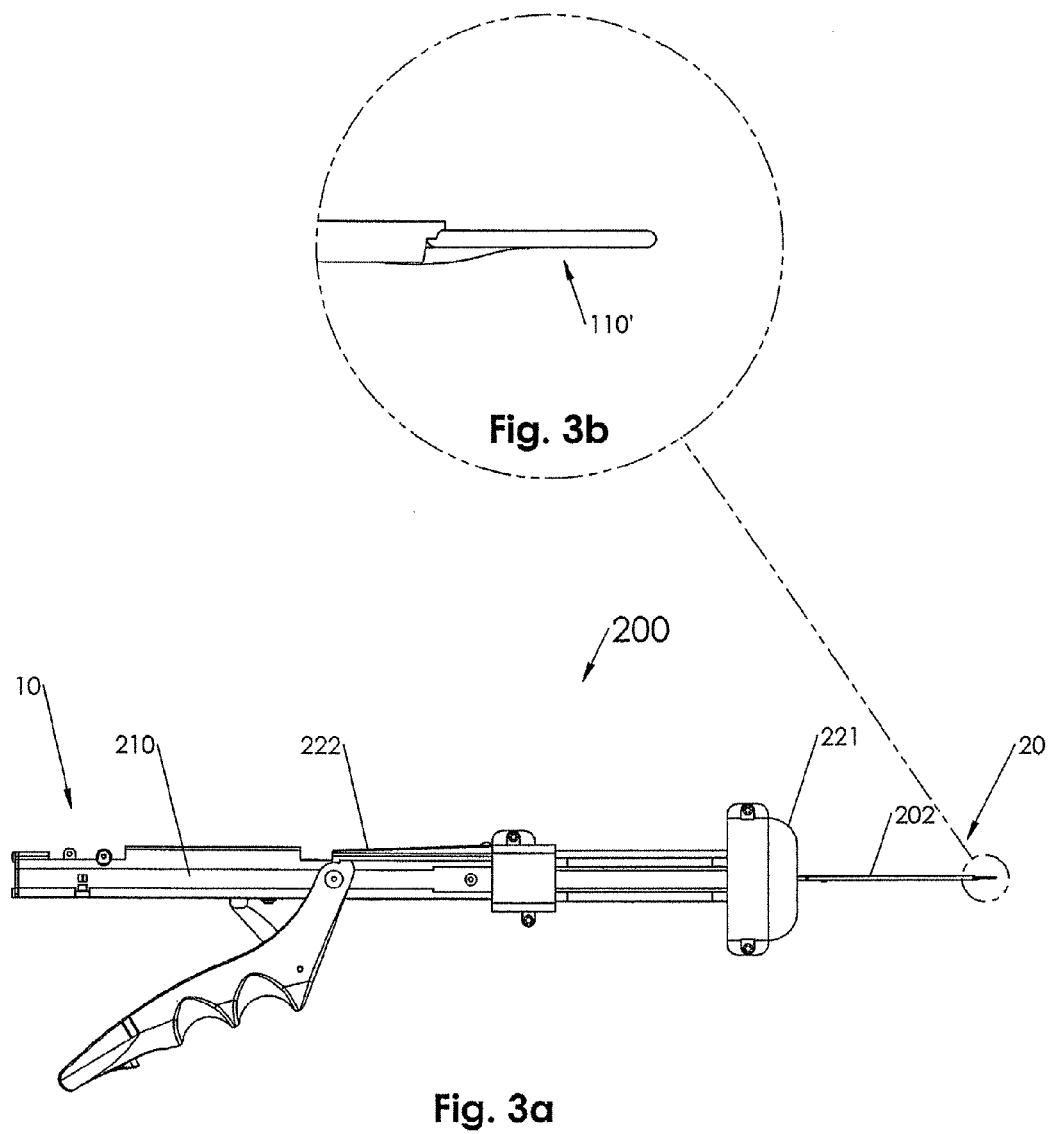
FIG. 3a is a partially exposed right side perspective view of the deployment device, according to an embodiment of the present invention.
FIG. 3b is a magnified window view of a portion of the deployment device of FIG. 3a, according to an embodiment of the present invention.
Figure 4B:
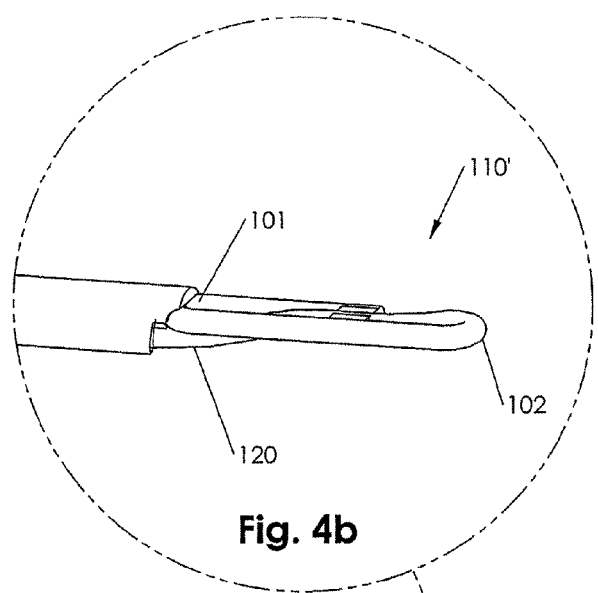
FIG. 4b is a magnified window view of a portion of the deployment device of FIG. 4a, according to an embodiment of the present invention.
Figure 4A:
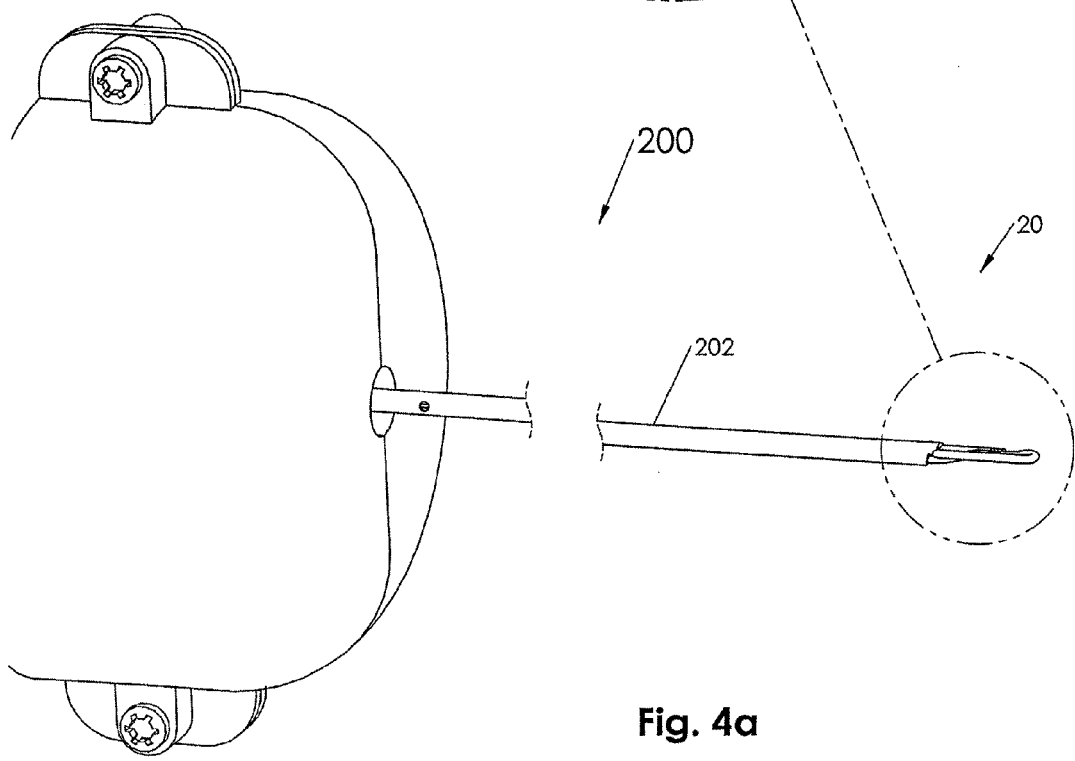
FIG. 4a is a perspective view of a distal portion of the of the deployment device, according to an embodiment of the present invention.

Turning to FIGS. 2a-4b, right side views (FIG. 2a shows a fully assembled deployment device 200, and FIGS. 2b, 3 and 4 are partially exposed views of the deployment device 200, i.e., missing parts to reveal other parts of the deployment device 200) of a deployment device 200, with a proximal end 10 and a distal end 20, according to an embodiment of the present invention is illustrated. In accordance with an embodiment of the present invention, prior to deployment into a vessel that requires sealing, the footplate 110' is located at the distal end 20 of a deployment device 200 and resides within an outer distal C-tube 201, while the remainder of the wire 120 is located proximally to the distal footplate 110' within the deployment device 200 ending at a wire ferrule 250 (see FIG. 7a, which is described infra). The footplate 110' is in an axial position relative to the longitudinal axis of the control housing 210 of the deployment device 200. The footplate's 110' proximal end 101 abuts the distal end of an inner distal C-tube 202, as described infra (see FIGS. 4a-4b).

Figure 5A:
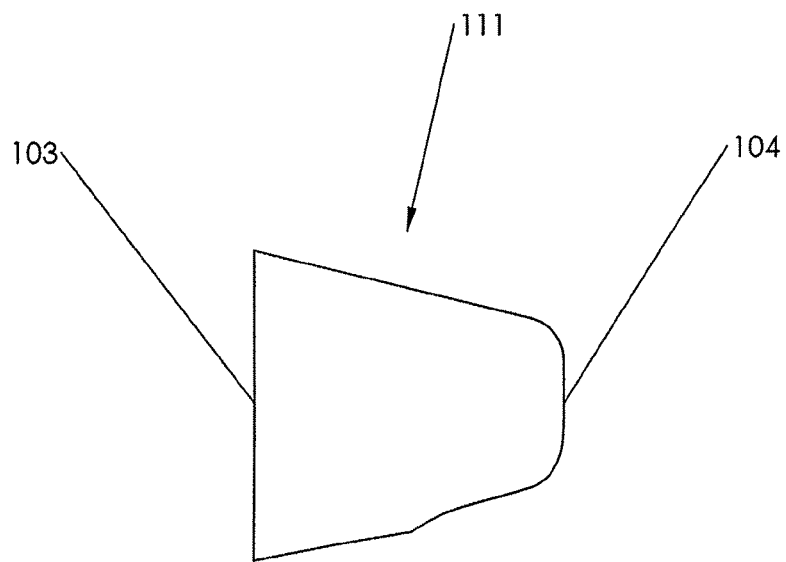
FIGS. 5a-5f are perspective views of the plug, according to an embodiment of the present invention.
Figure 5B:
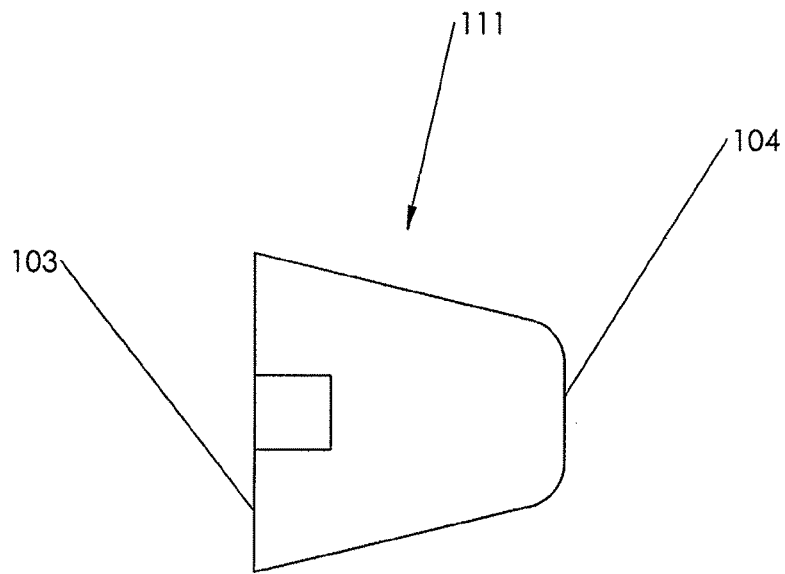
Figure 5C:
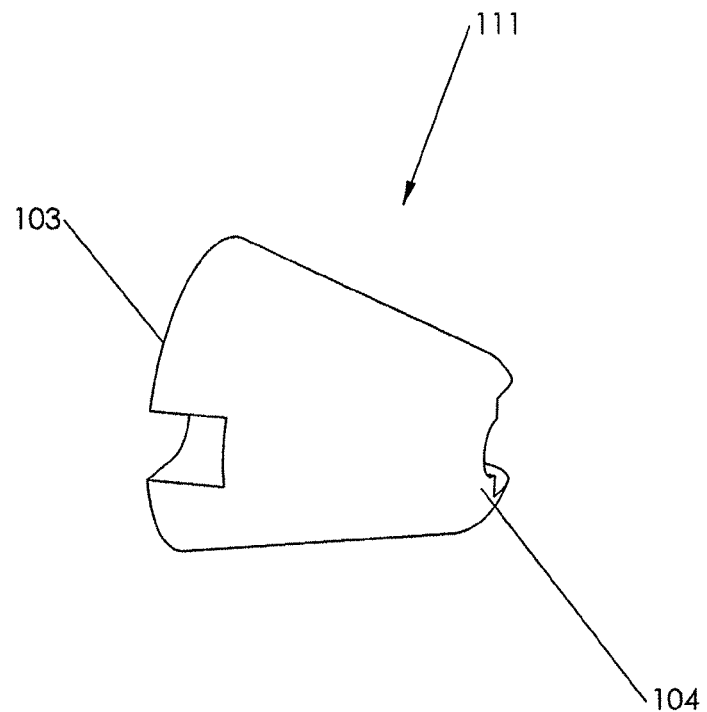
Figure 5D:
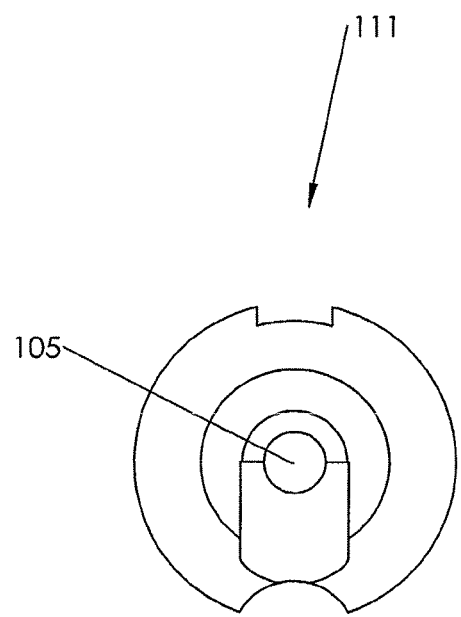
Figure 5E:
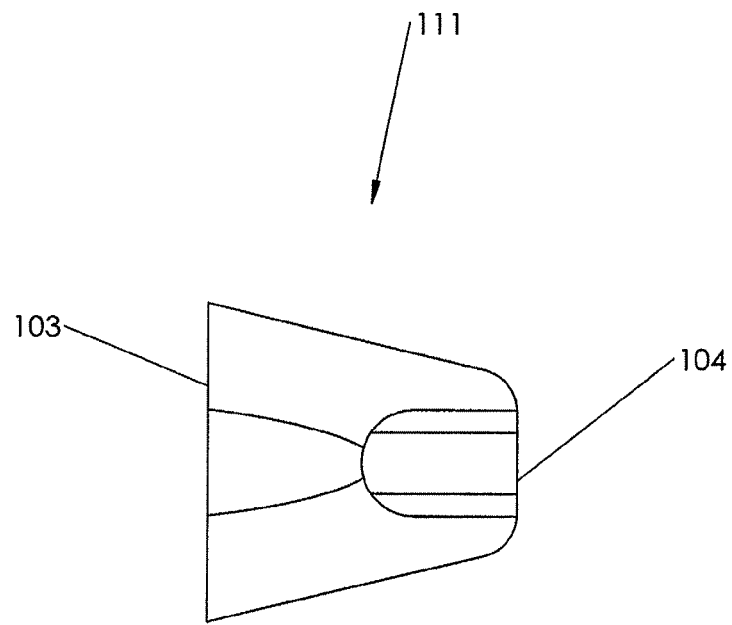
Figure 5F:
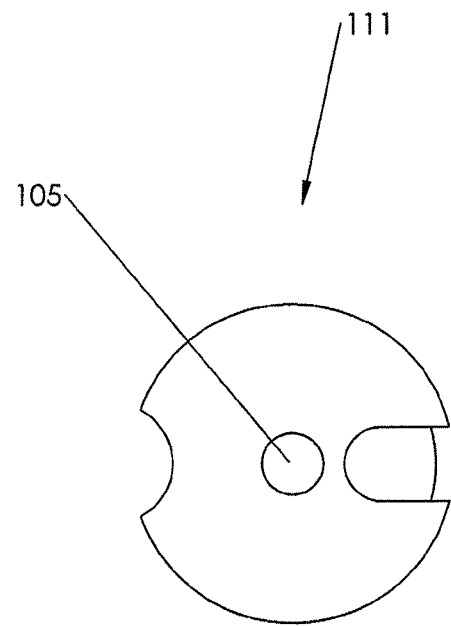

Turning to FIGS. 5a-f, a plug 111 according to an embodiment of the present invention is illustrated. These embodiments show a plug 111 that is conically-shaped and comprises a distal portion (or end) 104 and a proximal portion (or end) 103, wherein a diameter of the plug's distal portion 104 is smaller than a diameter of the plug's proximal portion 103. The diameter of the plug 111 at its largest point is greater than the diameter of the main conduit area 205 of the deployment device, as discussed infra. Turning to FIG. 5a, a right side view of the plug 111 is shown. Turning to FIG. 5b, a top side view of the plug 111 is shown. Turning to FIG. 5c, a left side inverted view of the plug 111 is shown. Turning to 5d, a front side view of the plug 111 with a lumen 105 is shown. Turning to FIG. 5e, a bottom side view of the plug 111 is shown. Turning to FIG. 5f, a rear side view of the plug 111 with a lumen 105 is shown. One or more "cutouts" or "cavities" may be provided in the distal end of the plug to allow nesting of the plug 111 with the footplate 110' and wire 120, according to an embodiment of the present invention. Also, one or more "cutouts" or "cavities" may be provided in the proximal end of the plug 111 to allow the insert 112 (see FIG. 10b) in the distal end of a push tube 212 to maintain rotational control of the plug 111 with respect to the footplate 110', according to an embodiment of the present invention. Embodiments of the present invention contemplate a plug 111 with various combinations of "cutouts" or without any "cutouts".

Figure 6B:
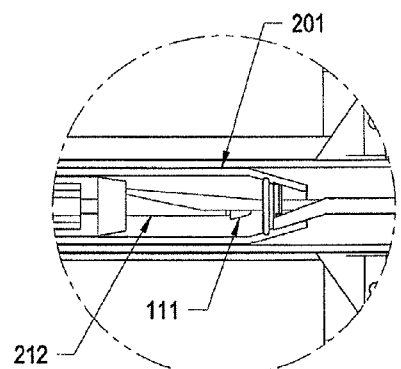
FIG. 6b is a magnified window view of a portion of the deployment device of FIG. 6a, according to an embodiment of the present invention.
Figure 6A:
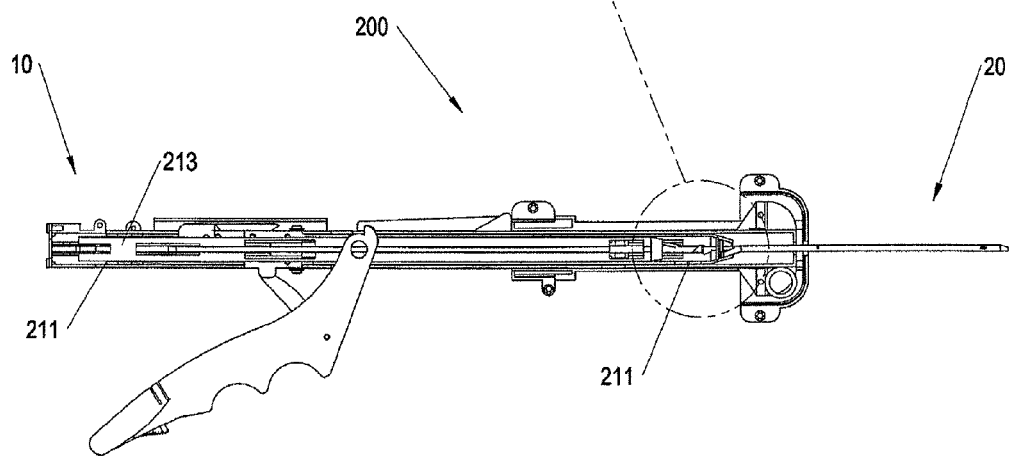
FIG. 6a is a partially exposed right side perspective view of the deployment device, according to an embodiment of the present invention.
Figure 6C:
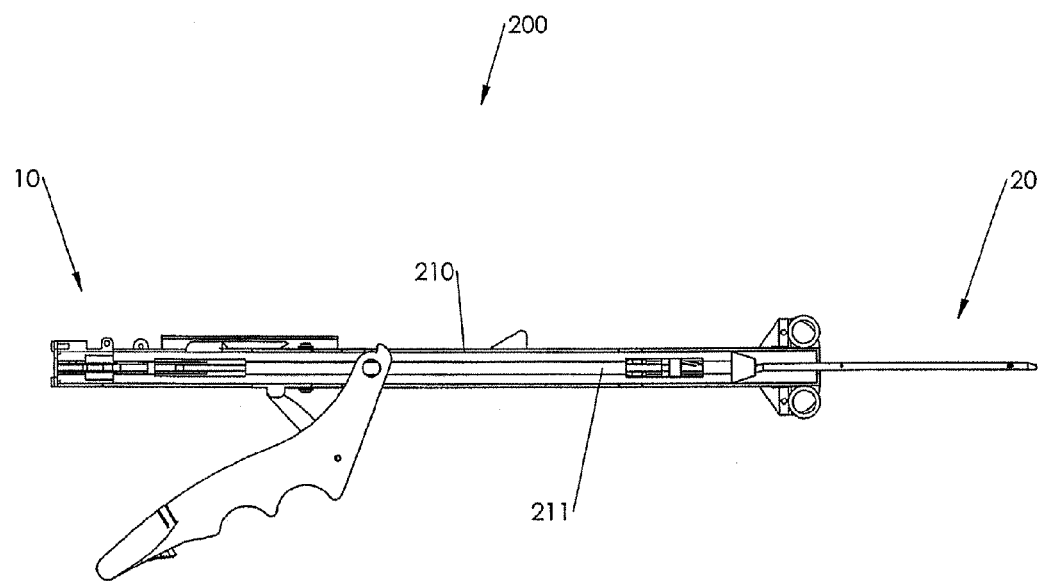
FIG. 6c is a partially exposed right side perspective view of the deployment device, according to an embodiment of the present invention.

Turning to FIGS. 6a-6c, a partially exposed right side view of a deployment device 200 in accordance with an embodiment of the present invention is illustrated. In accordance with an embodiment of the present invention, prior to deployment into a vessel that requires sealing (i.e., a pre-deployed closure device deployment configuration and position), the plug 111 is located proximally to the footplate 110' and along the longitudinal axis of the wire 120. The plug 111 is distally adjacent to the push tube 212, inside a distal portion of an outer proximal tube 211 (which is inside a control housing 210) of the deployment device 200.

Turning to FIGS. 7a-7c, a partially exposed top view of the deployment device according to an embodiment of the present invention is illustrated. This embodiment shows the location of the wire 120 within the deployment device 200. The wire 120 stretches from the footplate 110' through a longitudinally axial hole 105 (not shown) in the plug 111 in a distal to proximal direction. The wire 120 stretches from the footplate 110' through an inner distal C-tube 202 (not shown), and a sheer tube 224 (within the push tube 212), to the inner proximal end of a wire ferrule 250.

In accordance with an embodiment of the present invention, a pre-deployed closure device deployment configuration (default configuration) of the deployment device 200 of an embodiment of the present invention will be described generally from its distal end 20 to its proximal end 10, infra. Generally, in appropriate figures, acceptable fastening means (e.g., screws) are labeled with the number 226 and washers are labeled with the number 214. The method of use of the deployment device 200, and the closure device 100 in its post-deployed closure device deployment configuration and position, will be described infra.

Figure 8:
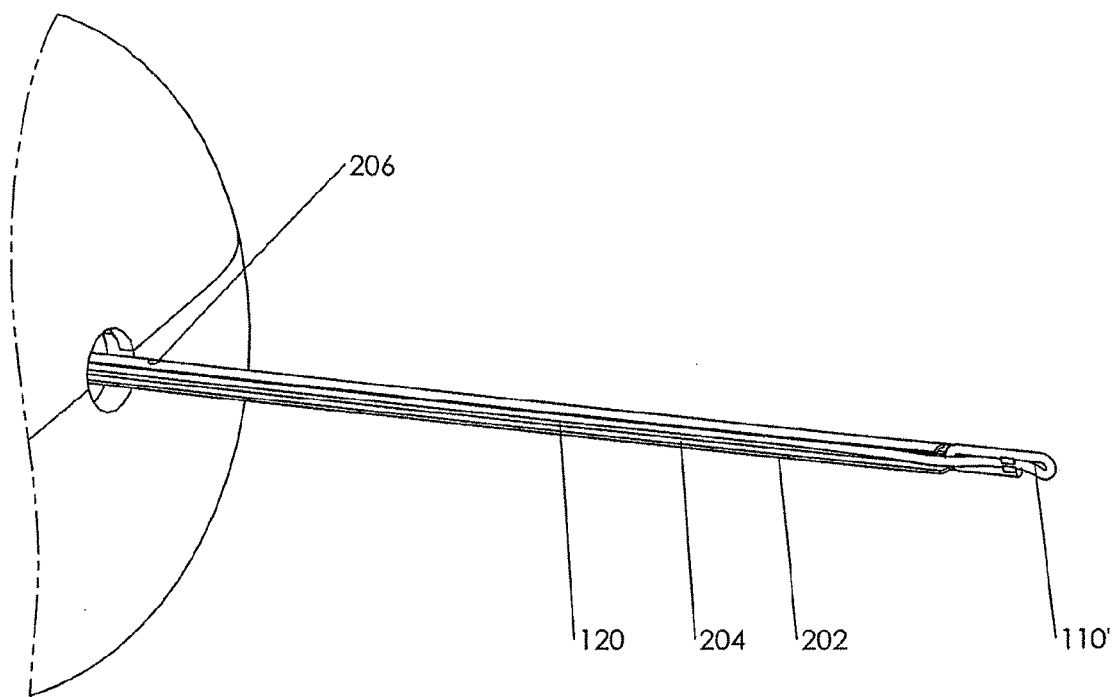
FIG. 8 is a perspective view of a partially exposed distal portion of the deployment device, according to an embodiment of the present invention.

Turning back to FIGS. 2a-2b, these embodiments show a deployment device 200 comprising an outer distal C-tube 201. The outer distal C-tube's 201 distal end comprises a narrowed nose or tip portion 203. This nose portion 203 of the outer distal C-tube 201 is the portion of the deployment device which houses the footplate 110' (not shown). The remainder of the outer distal C-tube 201 houses an inner distal C-tube 202 (see FIG. 8), comprising a longitudinal opening 204 in its bottom portion, and the wire 120. These distal C-tubes are concentrically nested together forming a main conduit area 205, which is described infra.

Figure 9B:
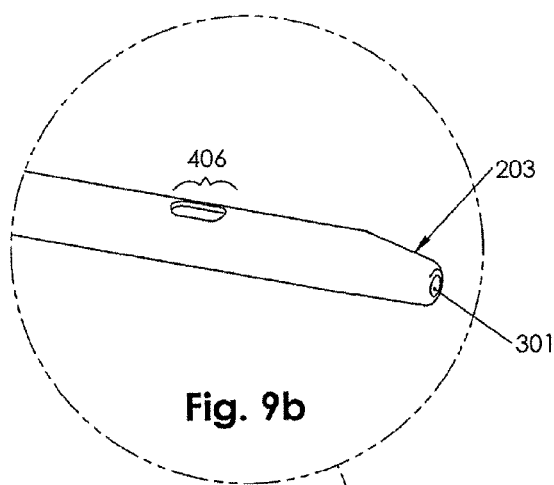
FIG. 9b is a magnified window view of a portion of the deployment device of FIG. 9a, according to an embodiment of the present invention.

Turning to FIGS. 8, 9a-9c, distal views of the deployment device 200 according to an embodiment of the present invention are illustrated. FIG. 9b shows the entrance—inlet hole 406—to a main conduit area 205 (see FIG. 9c) formed by the outer distal C-tube 201 and inner distal C-tube 202, which serves as a blood marking passageway. The inlet hole 406 resides toward the outer distal C-tube's 201 distal end. Further, the outer distal C-tube 201 and inner distal C-tube 202 each contains a side hole 206 (an atmospheric exit) which are concentrically aligned with one another. The side hole 206 is proximal to the footplate 110' and distal to the plug 111 (not shown). The side hole 206 is operable to serve as an atmospheric exit for proximal blood flow flowing from the blood vessel and into the inlet hole 406, and through the blood marking passageway 205. This proximal blood flow that exits the side hole 206 indicates that the footplate and distal portion of the deployment device 200 have entered the blood vessel (not shown, which is described infra). The main conduit area 205 additionally is operable to serve as a deployment area for deploying the plug 111, wherein the distal C-tubes are operable to locally expand and disassociate creating an irreversible un-nested condition to allow passage of the plug 111 into a post-vascular deployment configuration and position (see FIG. 9d).

Figure 9A:
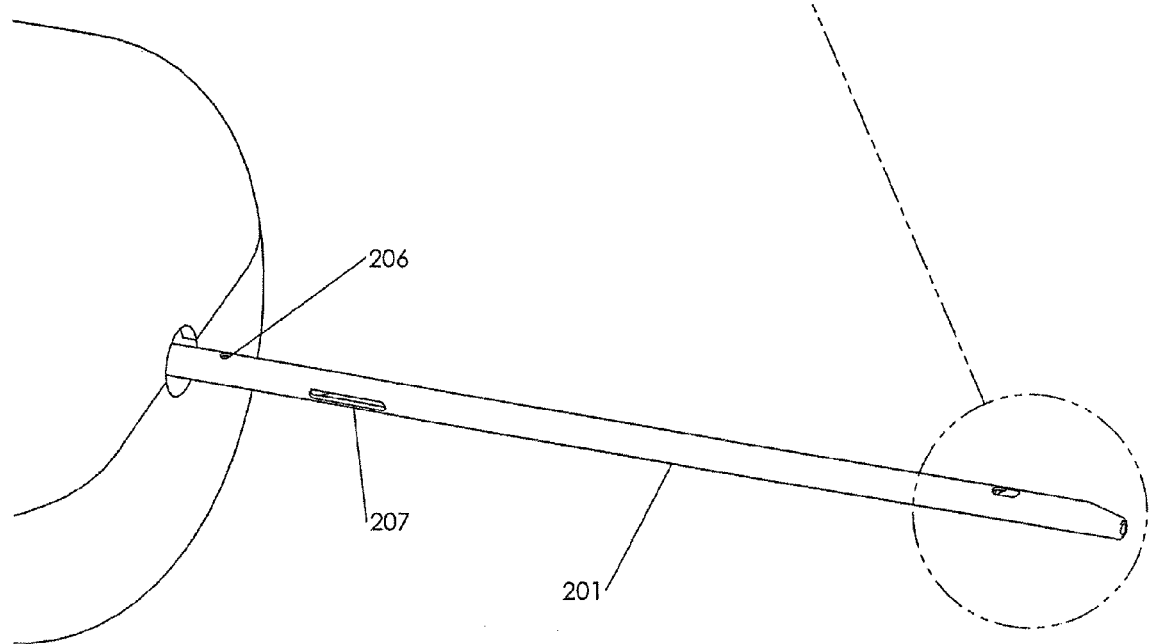
FIG. 9a is a perspective view of a distal portion of the deployment device, according to an embodiment of the present invention.
Figure 9C:
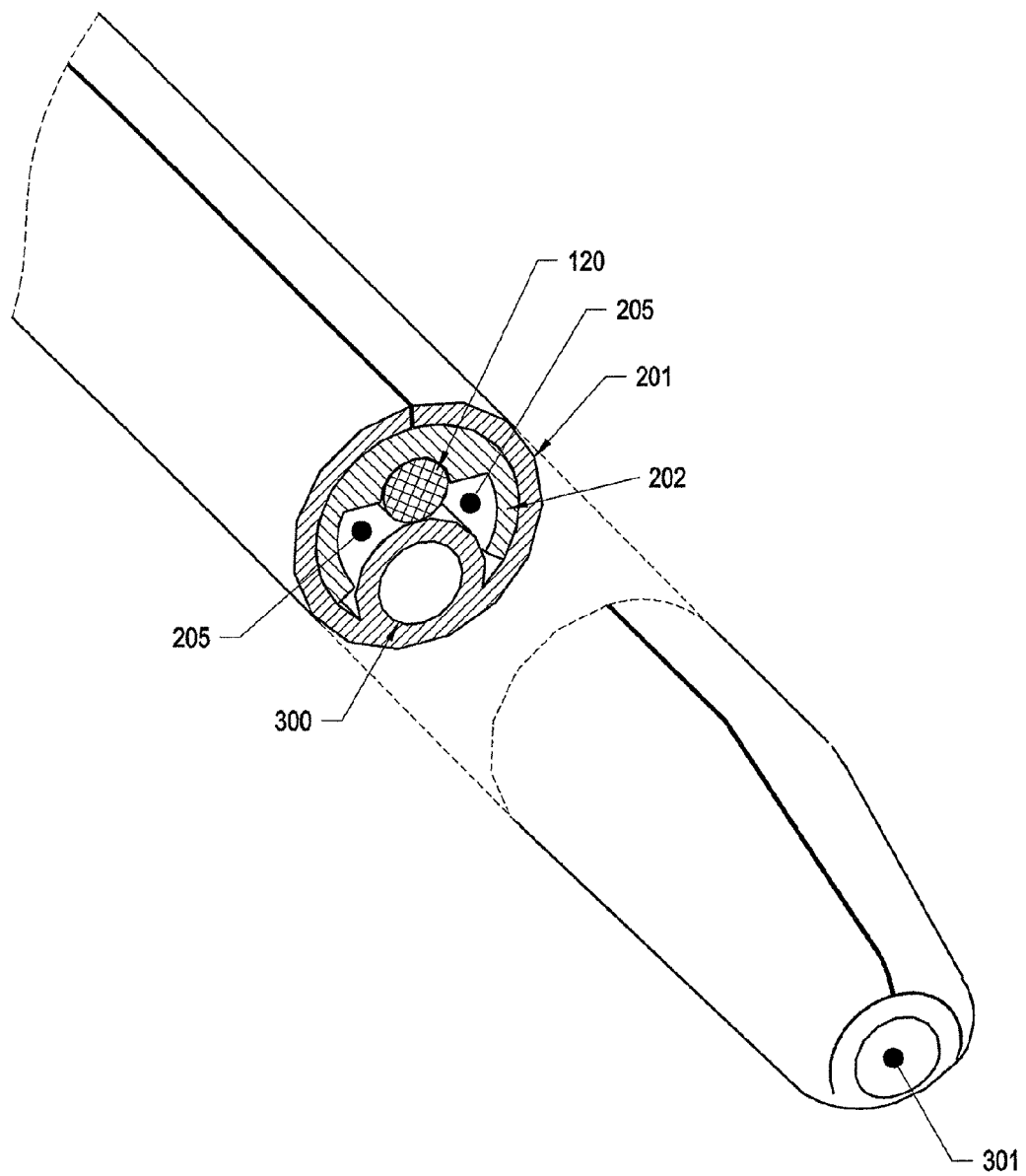
FIG. 9c is a cutaway perspective view of the distal end of the deployment device, according to an embodiment of the present invention.

In accordance with an embodiment of the present invention, FIGS. 9a & 9b are views of the distal portion of the deployment device 200 and FIG. 9c is a cut-away view of the distal portion of the deployment device 200, which shows the nested configuration of the outer distal C-tube 201 (including the guidewire lumen 300) and the inner distal C-tube 202, which together form the blood marking passageway 205, and a passageway in which the wire 120 nests, according to an embodiment of the present invention. The outer distal C-tube 201 comprises a guide wire lumen 300 (see FIG. 9c) comprising a proximal guide wire exit 207 (see FIG. 9a) and a distal guide wire entrance 301 (see FIGS. 9b & 9c) for insertion of a guide wire (not shown). The proximal guide wire exit 207 is proximal to the footplate 110' and distal to the plug's 111 pre-deployed closure device deployment position. The distal guide wire entrance 301 is located at the most distal point (at the distal nose portion 203) of the deployment device 200.

In accordance with an embodiment of the present invention, the outer distal C-tube 201 and inner distal C-tube 202 can move independently of one another in the longitudinal direction, i.e., the distal C-tubes are operable to independently slide along the longitudinal axis of the wire 120 (e.g., to allow and to assist in the actuation of the footplate 110' to a substantially perpendicular position relative to the longitudinal axis of the control housing 210 once inside the lumen of the artery, as will be discussed infra).

Figure 10B:
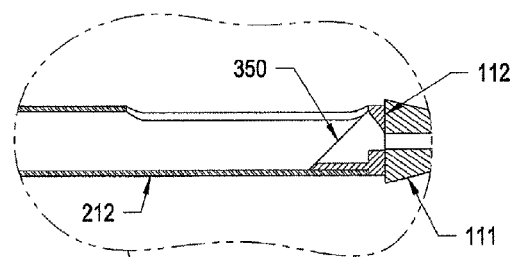
FIG. 10b is a magnified window view of a portion of the deployment device of FIG. 10a, according to an embodiment of the present invention.
Figure 10A:
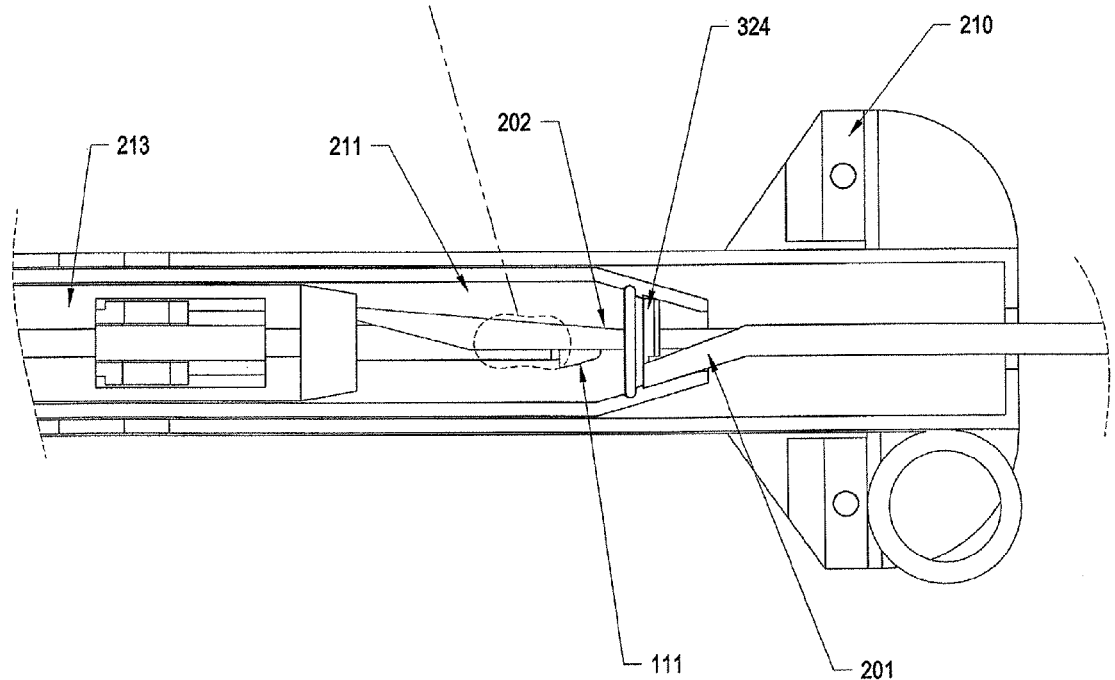
FIG. 10a is a right side perspective view of a partially exposed section of the deployment device, according to an embodiment of the present invention.

Turning to FIG. 10a-10b, a partially exposed right side view of the deployment device 200 in accordance with an embodiment of the present inventions is illustrated. This embodiment shows that the proximal ends of the outer distal C-tube 201 and inner distal C-tube 202 end just within an outer proximal tube 211 (the inner distal C-tube 202 ends at a retainer ring 325 (see FIG. 11, which is described infra) and slightly more proximally than the outer distal C-tube 201, which ends at a ring retainer 324 (see FIG. 11). The outer proximal tube 211 is surrounded by a control housing 210, which is in turn partially surrounded by a skin flange assembly 222 (not shown) comprising a distal portion 221 and a proximal portion 303 (see FIG. 2b). The skin flange assembly 222 (not shown) is operable to distally slide along a longitudinal axis of the wire 120, and along an outside portion of the control housing 210 and an outside portion of the distal C-tubes. The plug 111 is distally adjacent to an insert 112 and the distal end of a push tube 212, which mainly resides directly within an inner proximal tube 213 (which resides within the outer proximal tube 211, etc.) which stretches in the proximal direction to about the proximal end 10 of the deployment device 200 (see FIGS. 6a-6b). The proximal tubes are operable to independently slide along the longitudinal axis of the wire 120.

Figure 11:
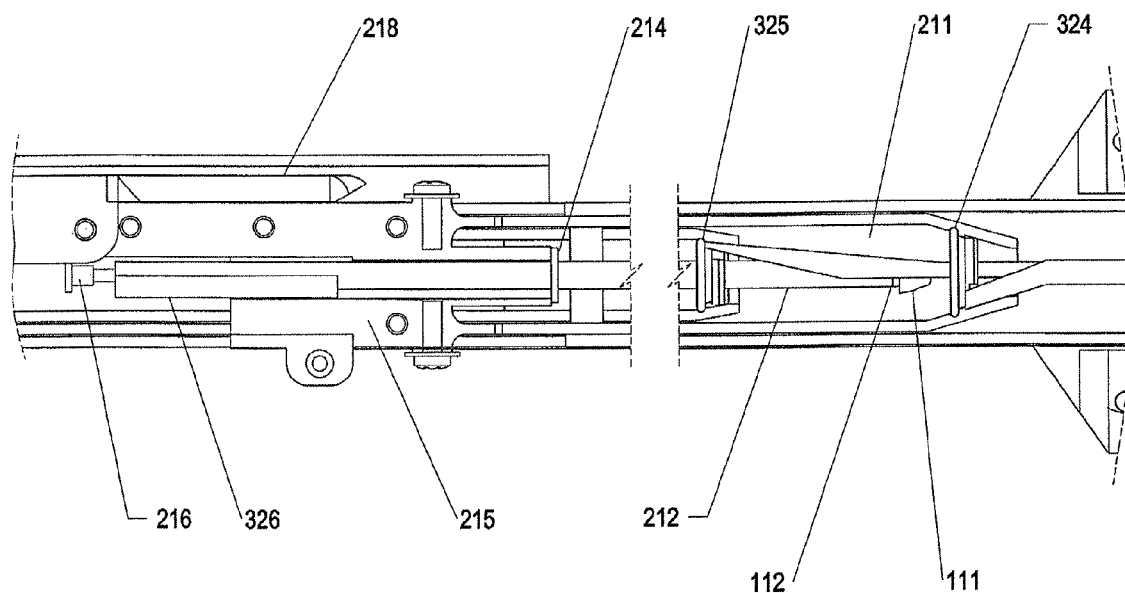
FIG. 11 is a right side perspective view of a partially exposed section of the deployment device, according to an embodiment of the present invention.
Figure 12:
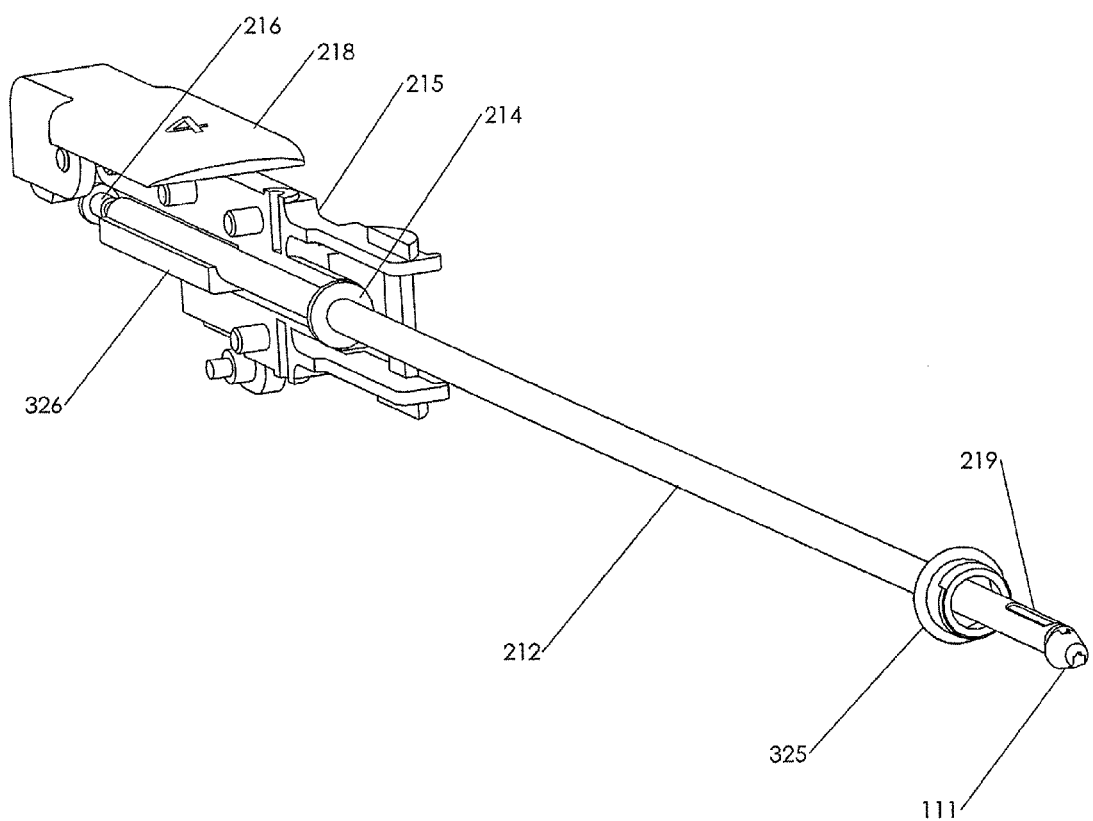
FIG. 12 is a right side perspective view of a partially exposed section of the deployment device, according to an embodiment of the present invention.
Figure 13:
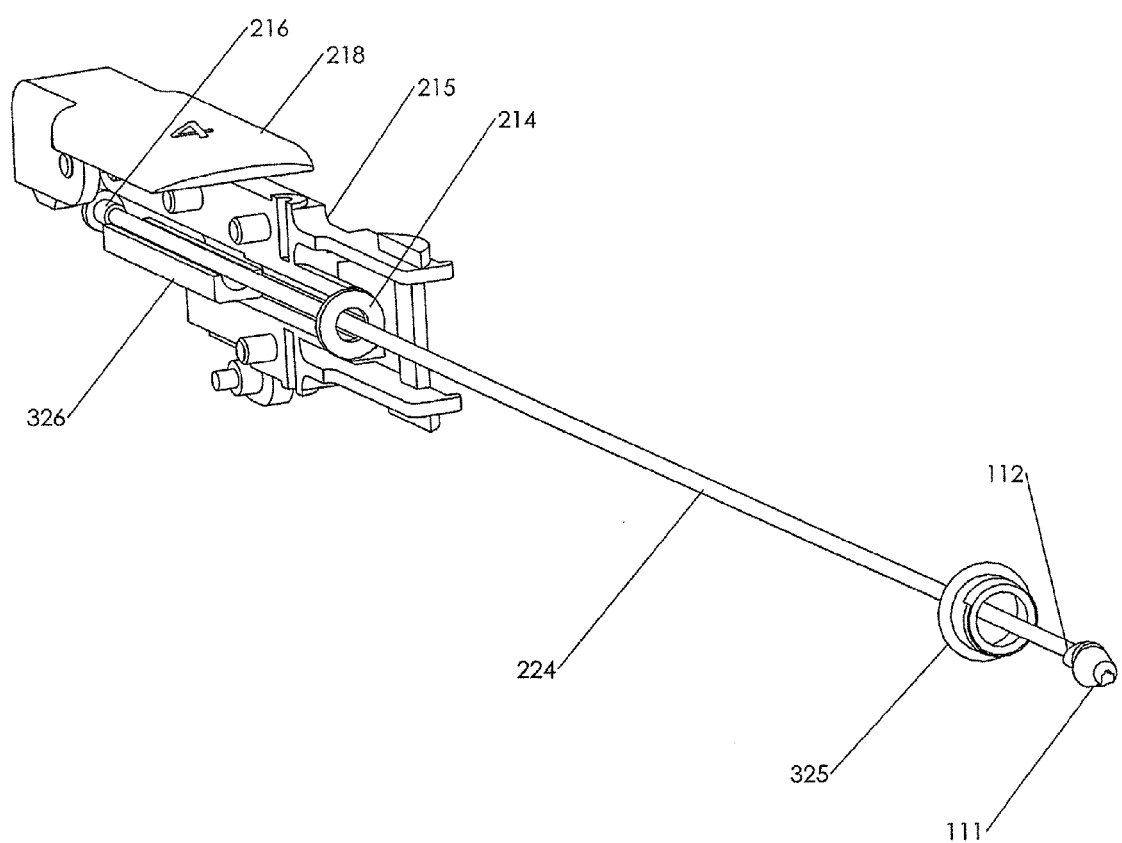
FIG. 13 is a right side perspective view of a partially exposed section of the deployment device, according to an embodiment of the present invention.

Turning to FIGS. 11-13, partially exposed right side views of the deployment device 200 of an embodiment of the present invention are illustrated. This embodiment shows the push tube 212, which resides within the proximal tubes (211, 213) and is surrounded by a ring retainer 325 at its distal end, and is cradled by an alignment key 326 at its proximal end. The push tube 212 extends proximally from the push tube insert 112 (which is affixed to the distal end of the push tube 212 by an appropriate means such as a weld) through a washer 214 (which is welded to the push tube 212 and whose proximal surface is adjacent to the distal end of a slide barrel 215), and protrudes through the main body of the slide barrel 215 such that its most proximal tip is approximately adjacent to the most proximal end of the slide barrel. At its distal end on the top, the push tube 212 has an opening 219 (which is a slot) that extends in a proximal direction from a point just slightly proximal of the distal tip of the push tube 212. Concentrically contained within the push tube 212 is a shear tube 224 which extends in a proximal direction from the push tube insert's 112 angled proximal surface 350 (see FIG. 30c) back to its most proximal end (slightly proximal of the most proximal end of the push tube 212). The proximal end of the shear tube 224 has a cap 216 affixed to it. The push tube 212 and the shear tube 224 are operable to distally slide along the longitudinal axis of the wire 120. The push tube 212 is operable to push the plug 111 through the main conduit area 205 into its post-deployed closure device deployment configuration and position as is discussed infra. The shear tube 224 (in conjunction with the push tube insert 112) is operable to both bend and shear-off the wire 120 into its post-vascular closure deployment configuration, as described infra.

Figure 14:
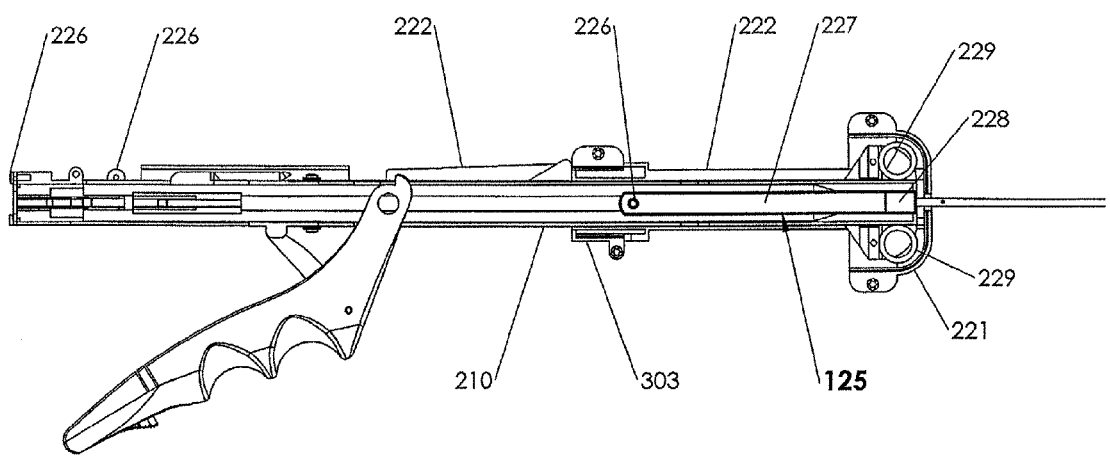
FIG. 14 is a right side perspective view of a partially exposed section of the deployment device, according to an embodiment of the present invention.
Figure 15:
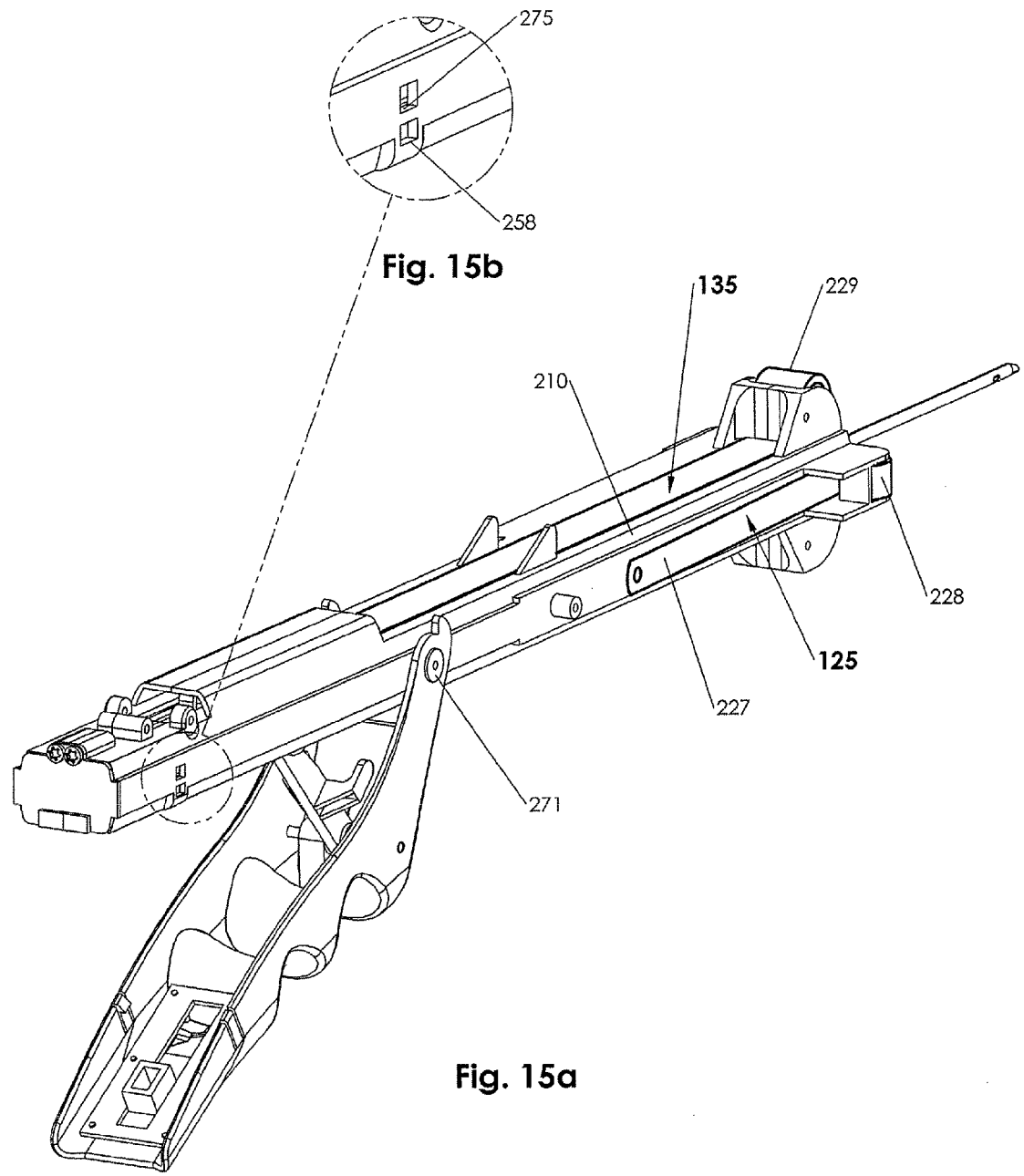
FIG. 15a is a partially exposed right side perspective view of the deployment device, according to an embodiment of the present invention.
FIG. 15b is a magnified window view of a portion of the deployment device of FIG. 15a, according to an embodiment of the present invention.
Figure 16:
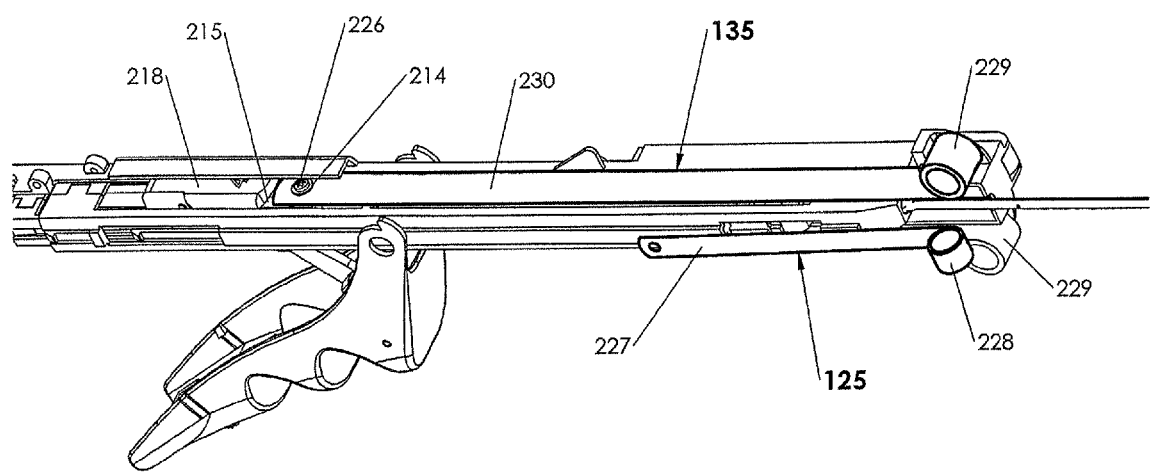
FIG. 16 is a right side perspective view of a partially exposed section of the deployment device, according to an embodiment of the present invention.

Turning to FIGS. 14-16, a partially exposed right side view of the deployment device 200 (shown in the default position) according to an embodiment of the present invention is illustrated. In accordance with an embodiment of the present invention, constant force springs comprising a plurality of lateral constant force springs, comprising a left lateral constant force spring 125 and a right lateral constant force spring 125, are provided. The lateral constant force springs 125 (left and right) each comprise a flat portion 227 and a roll spring portion 228. The roll spring portion 228 of each of the lateral constant force springs 125 (left and right) resides (nests) partially within the distal portion of the control housing 210, on the left and right side respectively (see FIG. 15*a*) and is covered by (contained within) the distal portion 221 of the skin flange assembly 222 (see FIG. 14). The flat portion 227 of the lateral constant force springs 125 (left and right) stretches flatly along the outside of the control housing 210 (on the left and right sides respectively) in a proximal direction from the roll spring portion 228, to the inside proximal portion 303 of the right and left sides (respectively) of the skin flange assembly 222 where they are fastened by an acceptable fastening means 226 (see FIG. 14). The lateral constant force springs are operable to move the skin flange assembly 222 in a distal direction by a constant distal force. The lateral constant force springs are also operable to apply a constant distal force to an outside surface of a patient's skin. Further, the lateral constant force springs are operable to apply a constant tensile proximal force to the wire 120. This constant tensile proximal force seats the footplate 110' against an inside wall 403 (not shown) of a blood vessel, wherein a datum is created at a point where the footplate 110' is seated, as discussed infra.

In accordance with an embodiment of the present invention, constant force springs comprising an upper and lower constant force spring 135, each comprising a flat portion 230 and a roll spring portion 229, are provided. The roll spring portions 229 of the upper and lower constant force springs 135 reside (nest) on the outside (on the top and bottom) of the distal end of the control housing 210, and are covered (contained within) the distal portion 221 of the skin flange assembly 222 (see FIG. 14). The flat portions 230 of the upper and lower constant force springs 135 extend proximally from the respective roll spring portions 229 (within the distal portion of the control housing 210) and stretch flatly along the outside of the control housing 210 (on the top and bottom respectively), and are fastened by an acceptable fastening means (e.g., a screw 226 and washer 214) to about the middle portion (top and bottom, respectively) of the slide barrel 215 (see FIG. 16). The upper and lower constant force springs 135 are operable to move the slide barrel 215 in a distal direction by application of a constant distal force to the slide barrel 215. The slide barrel 215 is operable to advance the push tube 212 in a distal direction by the constant distal force applied by the upper and lower constant force springs 135 to the slide barrel 215, wherein the plug 111 is pushed percutaneously into a percutaneous puncture (see FIG. 39) and into a post-deployed closure device deployment configuration and position. This post-deployed closure device deployment configuration and position is controlled by the creation of the datum (as discussed infra) with the wire 120 and the footplate 110', in order to seal the opening in the wall of the blood vessel.

Figure 17B:
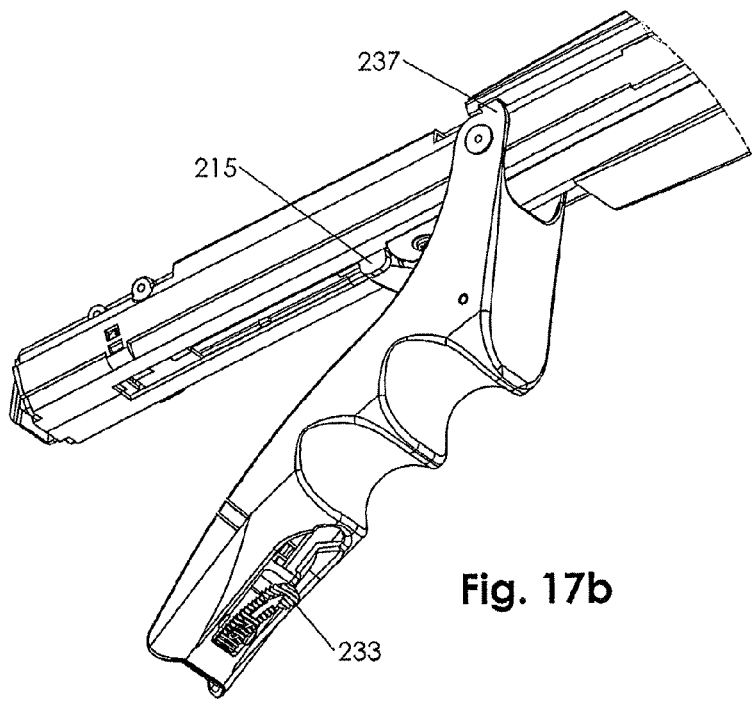
FIG. 17b is a right side perspective view of a partially exposed section of the deployment device, according to an embodiment of the present invention.
Figure 17A:
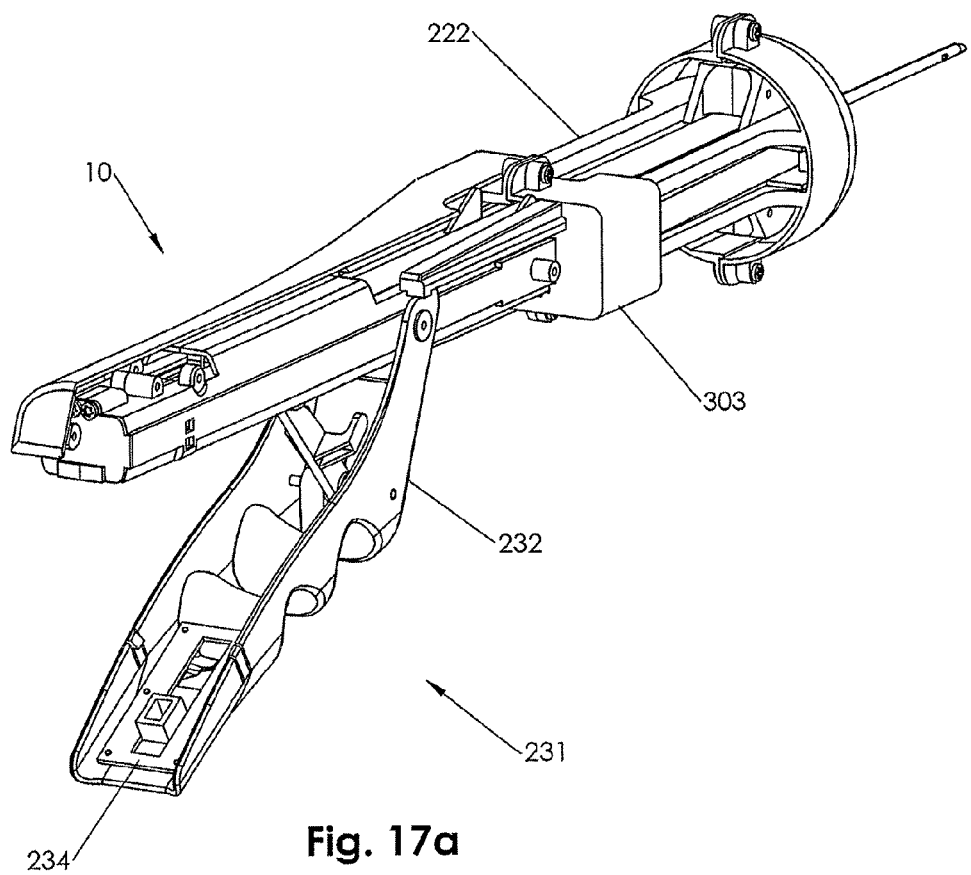
FIG. 17a is a partially exposed right side perspective view of the deployment device, according to an embodiment of the present invention.
Figure 18:
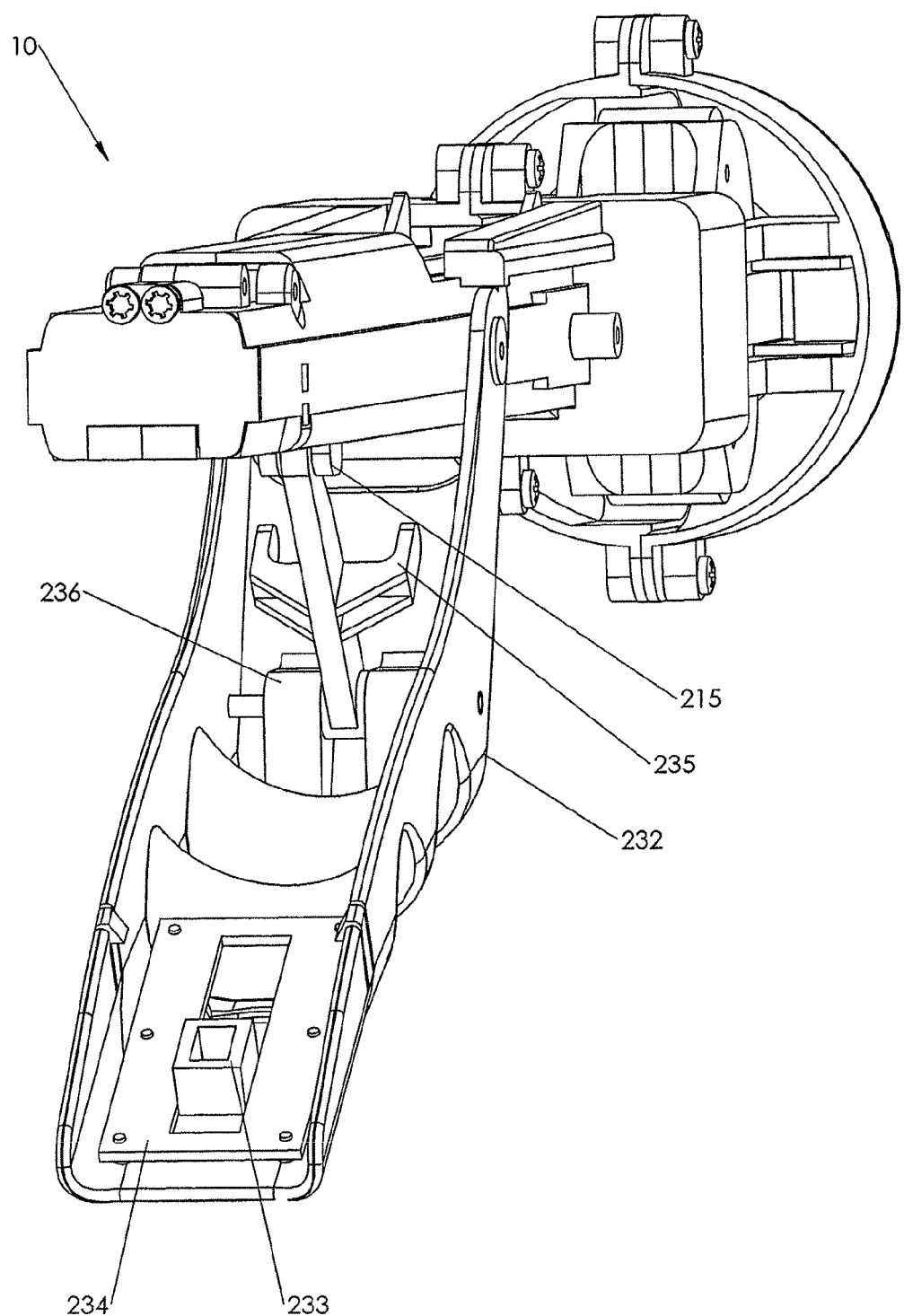
FIG. 18 is a partially exposed rear side perspective view of the deployment device, according to an embodiment of the present invention.

Turning to FIGS. 17*a*, 17*b*, and 18, the proximal end 10 (partially exposed right rear side and rear view) of the deployment device 200 according to an embodiment of the present invention is illustrated. This embodiment shows a squeeze lever handle assembly 231 of the deployment device 200. The squeeze lever handle assembly 231 comprises a squeeze lever handle 232, a button 233 held within a retainer plate 234 of the squeeze lever handle 232, and a link 235. The button 233 is slidable within the retainer portion 234. The link 235 is removably attached at its proximal end (by an upwardly hook-shaped portion or C-feature 266, not shown) to the bottom part (by a hinge pin 256, not shown) of the slide barrel 215 (which transfers mechanical energy to, and creates distal movement of, the slide barrel, upon the squeezing of the squeeze lever handle 232, described infra). The link 235 is attached at the other end (lower portion) to the squeeze lever handle 232 by a hinge pin mechanism 236. The squeeze lever handle 232 is removably attached to the proximal portion 303 of the skin flange assembly 222 (on both the left and right sides of the device) by lateral upper hook-shaped ends 237.

Figure 19:
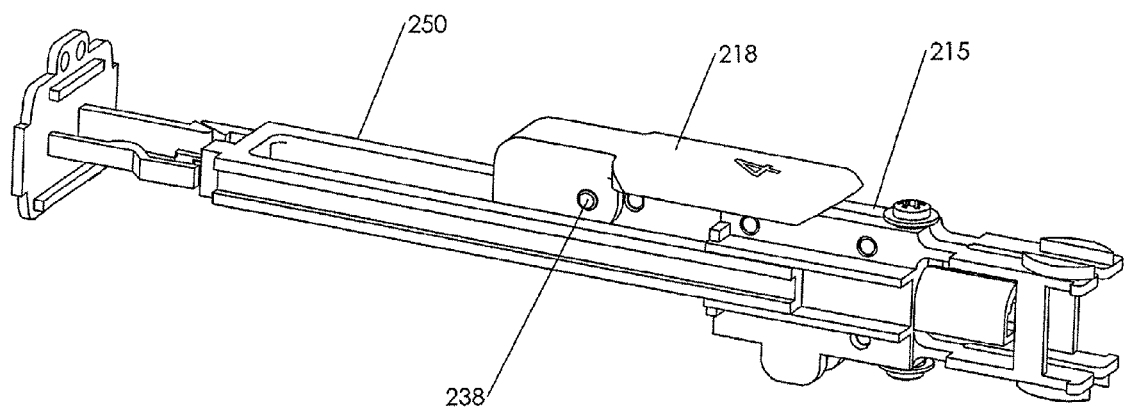
FIG. 19 is a right side perspective view of a partially exposed section of the deployment device, according to an embodiment of the present invention.

Turning to FIG. 19, an exposed right side view of components interlocated in the proximal portion of the deployment device 200 according to an embodiment of the present invention is illustrated. This embodiment shows a slide barrel assembly comprising a slide barrel 215, and a cut-off lever 218 that comprises a proximal portion which is hingedly attached by a hinge pin mechanism 238 to the slide barrel 215. A distal portion of the cut-off lever 218 is hingedly movable about the hinge pin mechanism 238 in a perpendicular direction away from the longitudinal axis of the wire 120 (not shown). The slide barrel 215 is distal to where the proximal end of the wire 120 (not shown) attaches to the wire ferrule 250 and is contained within the control housing 210 (not shown). The slide barrel assembly is operable to distally slide along the longitudinal axis of the wire 120 (not shown).

Figure 20:
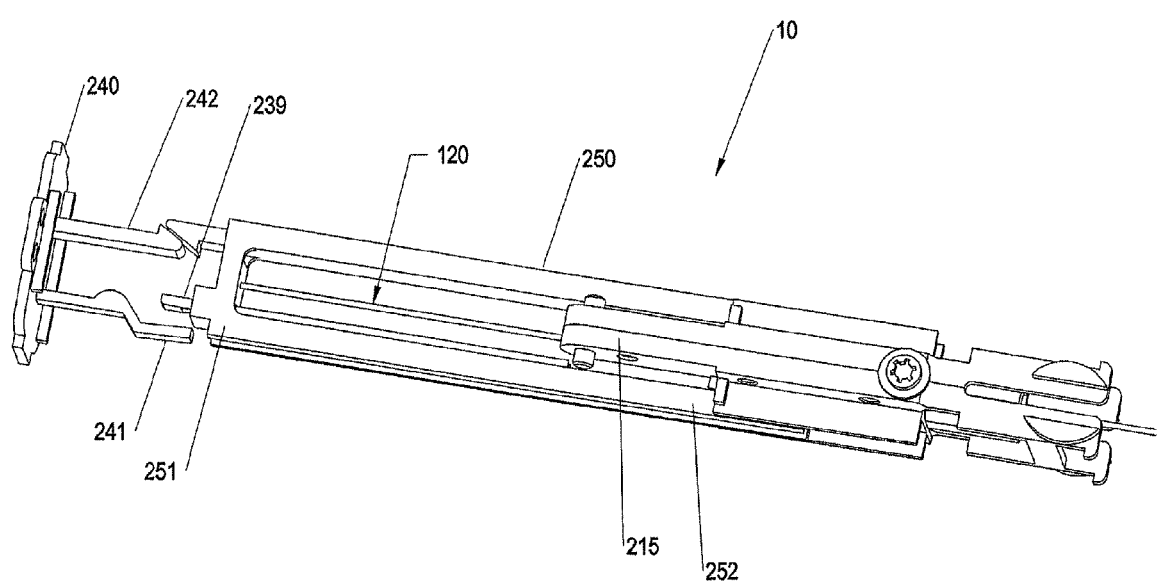
FIG. 20 is a top side perspective view of a partially exposed section of the deployment device, according to an embodiment of the present invention.
Figure 27:
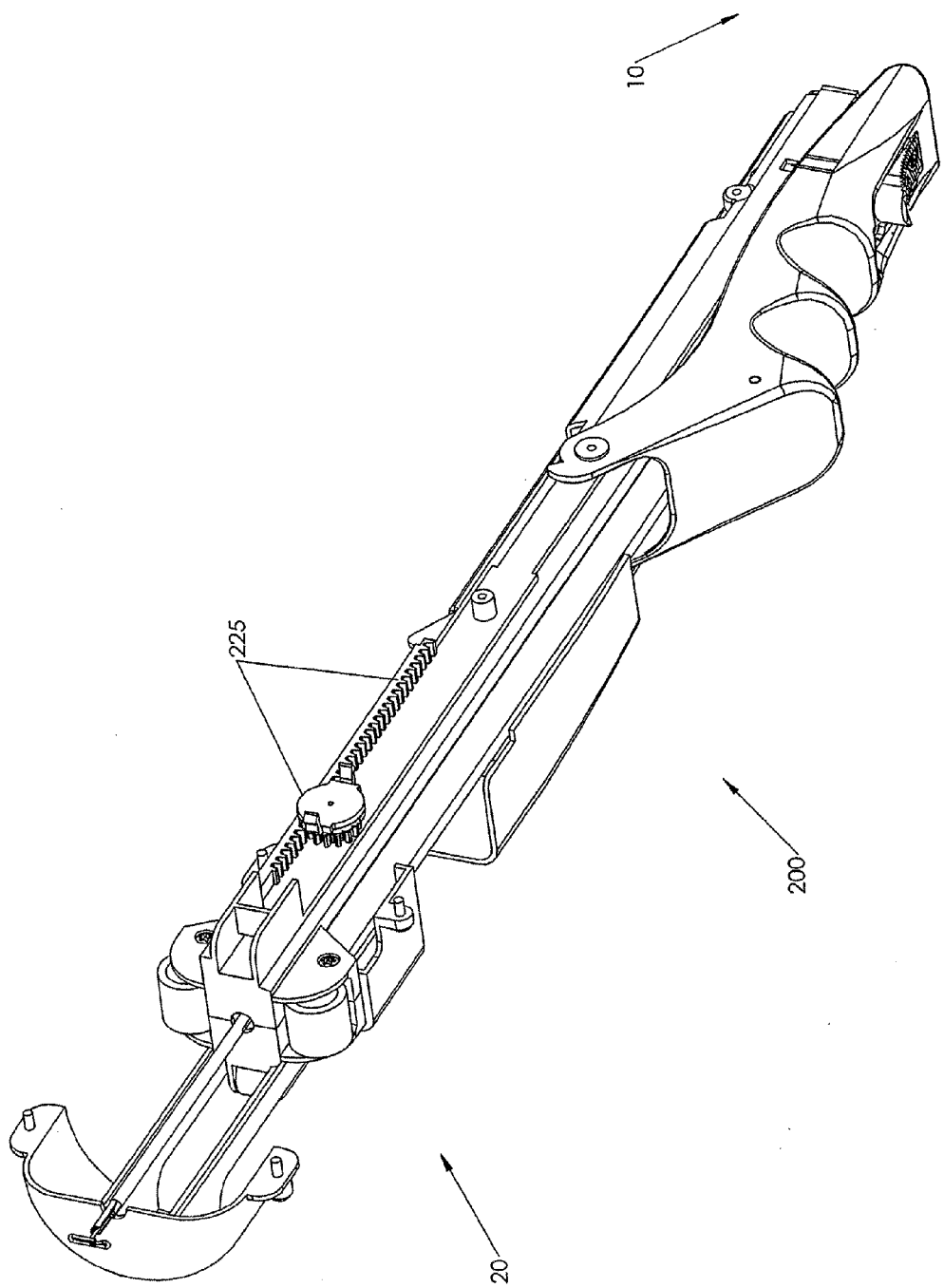
FIG. 27 is a left side perspective view of a partially exposed section of the deployment device, according to an embodiment of the present invention.

Turning to FIG. 20, an exposed top view of components interlocated in the proximal portion of the deployment device 200 according to an embodiment of the present invention is illustrated. This embodiment shows the wire ferrule 250, which comprises an elongated U-shaped structure. The elongated U-shaped structure comprises a closed proximal end 251 and an open distal end 252. The wire ferrule 250 resides within the inner proximal tube 213 (not shown) and is operable to longitudinally slide along the longitudinal axis of the wire 120 (not shown). Protruding through the right-side proximal end of the wire ferrule 250 is a release shaft 239 that extends distally to about the proximal end of the slide barrel 215. Also shown, at the most proximal end 10 of the deployment device 200 is a proximal control housing cap 240, that has two laterally spaced cap fingers (right cap finger 241, left cap finger 242) extending from the proximal control housing cap's 240 distal inner surface.

In accordance with an embodiment of the present invention, at the conclusion of a diagnostic or therapeutic intravascular surgical procedure, a closure device 100 of an embodiment of the present invention is deployed by a deployment device 200 of an embodiment of the present invention to control (or stop or prevent) the bleeding by plugging or sealing the arteriotomy (the method of deployment is described, infra).

Figure 31A:
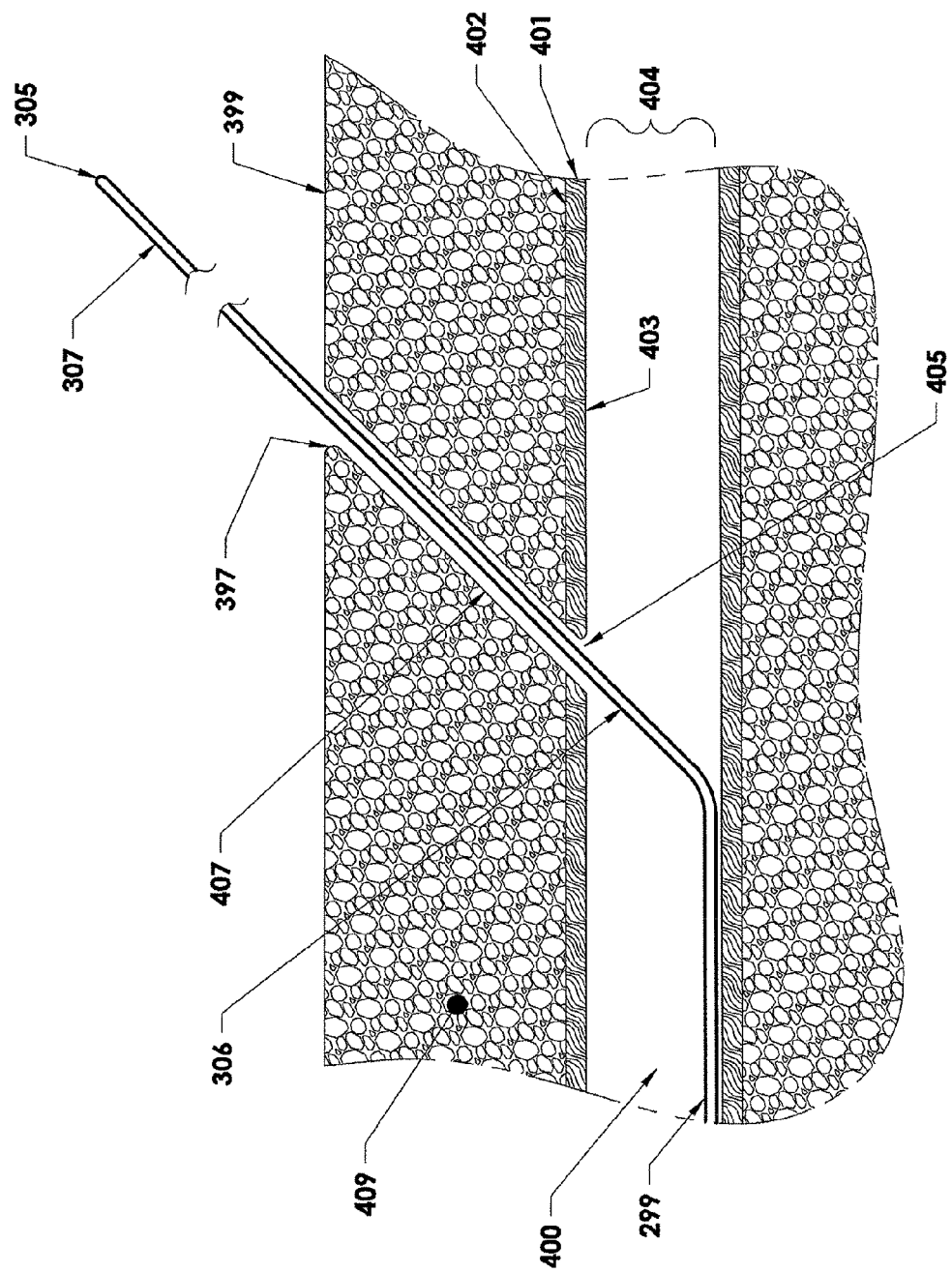
FIGS. 31-41 show the sequential steps in the use of the deployment device to deploy the closure device to seal an opening formed through a blood vessel, according to an embodiment of the present invention.

In accordance with an embodiment of the present invention, following a intravascular surgical procedure, a guide wire 299 (as shown in FIG. 31*a*) is preferably left in the site of the arteriotomy (vessel wall is shown by number 401) after the operating cannula is removed by the clinician. (Alternatively, a new guide wire 299 may be inserted into the arteriotomy). This guide wire 299 extends distally from its exposed portion 307 (outside the patient's body), to its unexposed portion 306 (inside the patient's body), i.e., through the skin puncture 397 of the patient's skin 399, through the tissue tract 407, through the arteriotomy 405, and into the lumen 404 of the blood vessel 400, as described supra.

In accordance with an embodiment of the present invention, a method of sealing an opening (an arteriotomy) formed in the wall 401 of a blood vessel 400 (e.g., an artery such as the femoral artery, where the opening in the wall of the blood vessel was percutaneously formed in conjunction with a tissue tract contiguous with the opening and extending proximally through subcutaneous tissue and through the surface of the skin overlying the blood vessel (the percutaneous puncture) (see FIG. 31a), by a clinician during a diagnostic or therapeutic intravascular surgical procedure, will now be described in a series of motions. That is, those motions/actions initiated by the user, and those motions which occur passively within the assemblies of both the closure device 100 and the deployment device 200. The method comprises providing a system comprising a closure device 100 for sealing an opening (an arteriotomy) formed in the wall 401 of a blood vessel 400 (see FIG. 43), and a deployment device 200 (see FIG. 2a) for deploying the closure device 100 into the opening (the arteriotomy) formed in the wall 401 of a blood vessel 400, to seal the opening 405.

Embodiments of the methods of the present invention, with are described and illustrated herein, are not limited to the sequence of motions/actions described, nor are they necessarily limited to the practice of all of the motions set forth. Other sequences of motions, or less than all of the motions, or simultaneous occurrence of the motions, may be utilized in practicing the embodiments of the invention.

FIGS. 31a-43 show the functionality of the distal portion 20 of the deployment device 200 and the closure device 100 (including the guide wire 299, as described supra) with respect to a patient's anatomy and the incisional architecture of the percutaneously formed puncture created prior to a vascular closure procedure, i.e. skin puncture, tissue tract, arteriotomy, etc., as described infra, in accordance with an embodiment of the present invention.

Turning to FIG. 31a, prior to the beginning of the use of the deployment device 200, the guide wire 299 is in place, i.e., an unexposed portion 306 of the guide wire 299 extends from the patient's skin 399, in a distal direction through the skin puncture 397 and the tissue tract 407, to a position inside the lumen of the blood vessel 404; and an exposed portion 307 (contiguous with the unexposed portion 306) of the guide wire 299 extends in a proximal direction from the patient's skin such that it is outside the patient's body.

Figure 31B:
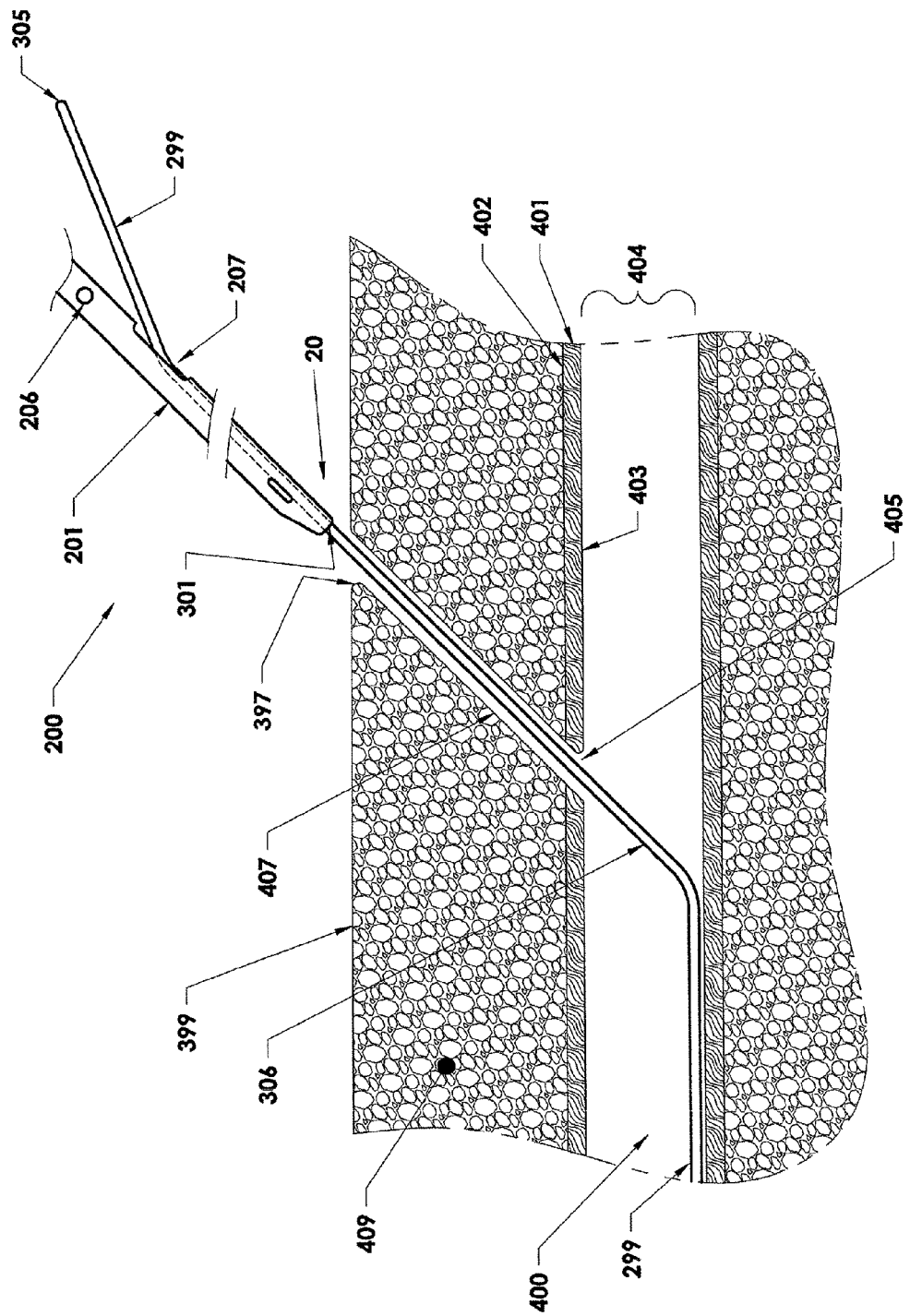
Figure 32:
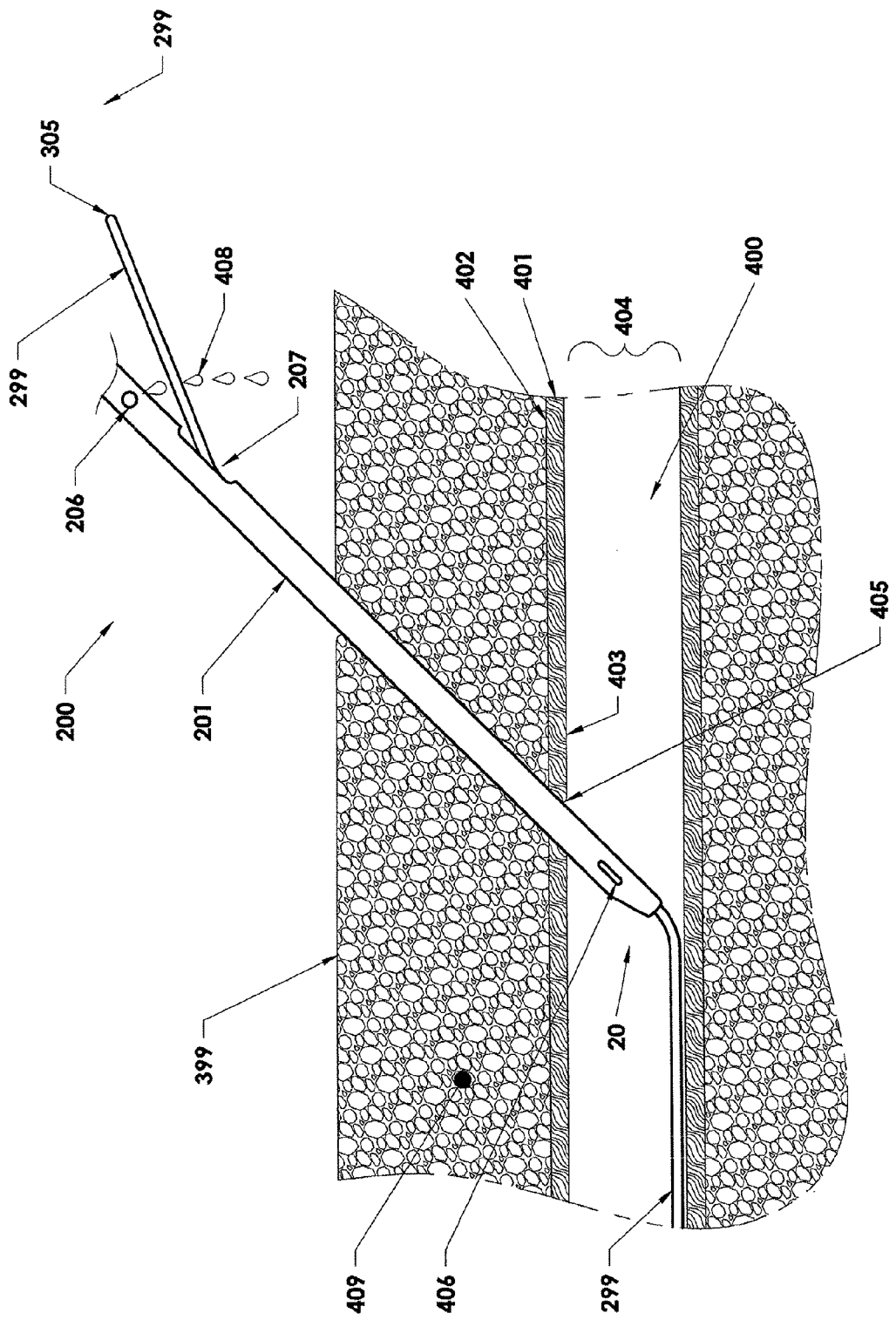
Figure 33:
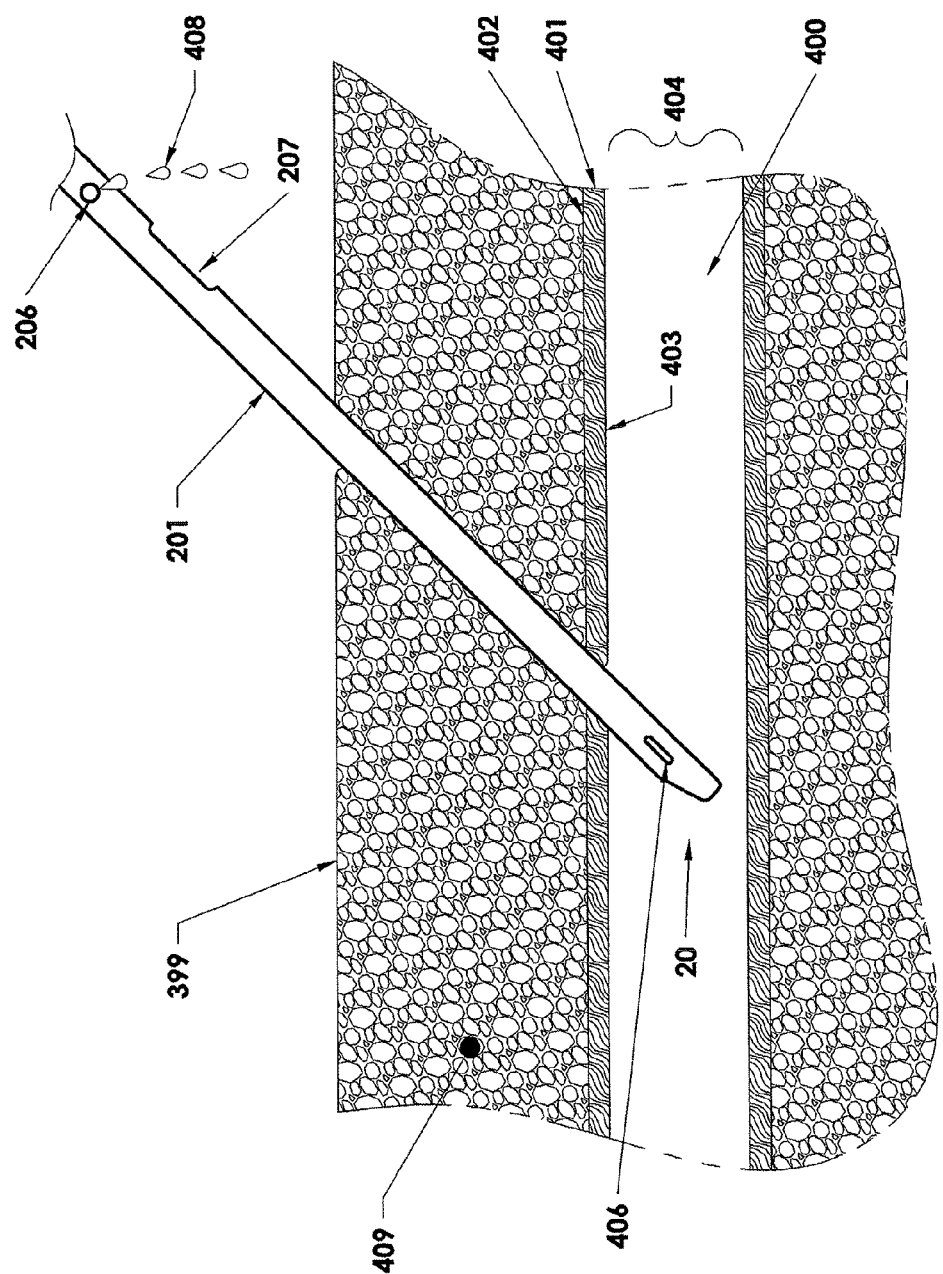

Turning to FIGS. 31b & 32, at the beginning of the deployment of the closure device 100 by the deployment device 200, the proximal tip 305 of the guide wire 299 (which is in a pre-existing position partially inside the patient's body and partially outside the patient's body, as described supra) is inserted into the guide wire entrance 301 (in a proximal direction). The guide wire 299 is further advanced proximally until the proximal end 305 of the guide wire 299 travels through the guide wire exit 207. Once the proximal end 305 of the guide wire 299 has protruded through the guide wire exit 207 and is exposed outside the device, the guide wire 299 is grasped and pulled by the user to remove any slack in the guide wire 299 without changing the position of the guide wire 299 inside the patient's body. The deployment device 200 may then be advanced in a distal direction, over the guide wire 299 such that the distal end 20 of deployment device 200 passes through the skin puncture 397 (at an angle of less than 90° relative to the plane of the surface of a patient's skin 399), continues moving distally through the length of the percutaneously formed puncture, i.e., through the tissue tract 407 (extending through the subcutaneous tissue 409 overlying the vessel 400), and through the arteriotomy 405 into the lumen 404 of the blood vessel 400, until the distal end 20 of the deployment device 200 (comprising the footplate 110' and the distal ends of the distal C-tubes) are intralumenal (inside lumen 404 of the blood vessel 400).

In accordance with an embodiment of the present invention, once inside the vessel 400, owing to the positive arterial blood pressure, blood flows into the main conduit area 205 (which acts as a blood marking passageway) via the inlet hole 406 and then proximally to the side hole 206, where blood droplets 408 can be observed ("blood marking") (see FIG. 32). Such visual observation of proximal blood flow is an affirmative indication to the user that the footplate 110' is positioned inside the vessel 400. The distal end 20 of the deployment device 200 is then preferably advanced a few millimeters more to make sure that the footplate 110' is completely within the lumen 404 of the blood vessel 400, and that the clinician is not observing false blood marking. The guide wire 299 is then completely removed by the user (by pulling it in the proximal direction through the proximal guide wire exit 207) and then disposed of in a proper medical waste container, while the deployment device 200 is held in place by the user. (See FIG. 33—guide wire 299 has been removed, while the distal end 20 of the deployment device 200 remains within the lumen 404 of the blood vessel 400, i.e., the default position).

FIGS. 21a-30c relate to the deployment of the closure device 100 by the deployment device 200 in accordance with an embodiment of the present invention. These figures show the action and automatic functionality of the deployment device 200 as well as depict the sequential displacements (movements) of the various parts within the assembly of the deployment device 200. FIGS. 21a-30c are shown primarily as section views to enable a better understanding of the relative movements of the individual parts within the assembly of the deployment device 200 (without showing the percutaneous puncture, blood vessel, etc.), according to an embodiment of the present invention. In these figures, an axial center-line is indicated which is coincident with the longitudinal center-line of the wire 120. These figures also provide "windows" for close-up views of the inner workings of specific portions (shown by a dashed line and circle) of the device 200. Parts of the deployment device such as the inner proximal tube 213, the outer proximal tube 211, wire ferrule 250, the slide barrel 215, cut-off lever 218, squeeze lever handle 232, link 235 and button 233, right and left side lateral constant force springs 125 (comprising the roll spring portion 228 and the flat portion 227), lateral upper hook-shaped ends 237, upper and lower constant force springs 135 (comprising roll spring portions 229 and the flat portions 230), the outer distal C-tube 201, the inner distal C-Tube 202, the footplate 110' (monolithic footplate embodiment shown), the plug 111, sheer tube 224, and the nose portion 203 of the outer distal C-tube 201, are shown.

As described supra, FIGS. 33-43 show the relative movements of the individual parts of the distal portion 20 of the deployment device 200 and the closure device 100, with respect to the patient's anatomy and the architecture of the percutaneous passageway, i.e., skin puncture, subcutaneous tissue tract, arteriotomy, and blood vessel, according to an embodiment of the present invention.

Turning to FIGS. 21a-21d, a deployment device 200 is shown in its default position, prior to the squeeze lever handle 232 being squeezed by the user. The squeeze lever handle 232 is in the fully open (un-squeezed) position. The squeeze lever handle 232 is hingedly attached to the control housing 210 via cylindrical features 271 that extend from both sides of the control housing 210 and are coaxial with the through-holes 272 in the distal ears of the squeeze lever handle 232. A link 235 is hingedly attached to both the squeeze lever handle 232 and the slide barrel 215. This link 235 is a coupling element that transmits force from the squeeze lever handle 232 to the slide barrel 215. At this step, the inner proximal tube 213 and outer proximal tube 211 are in their fully distal positions. The lateral upper hook-shaped ends 237 of the squeeze lever handle 232 are engaged with the hooked features 255 of the proximal end 222 of the skin flange assembly 222. The inner distal C-tube 202 (not shown) and outer distal C-tube 201 are in their fully distal positions. The footplate 110' (not shown) is housed in the outer distal C-tube 201. The closed end of the footplate 101' is in frictional contact with the under-cut feature 208 at the distal end of the inner distal C-tube 202 (see FIG. 22e).

In accordance with an embodiment of the present invention, after the guide wire 299 is removed from the deployment device 200, the distal end 20 of the deployment device 200 (in which the footplate 110' resides) is within the lumen of the vessel (see FIG. 33) prior to the squeeze lever handle 232 being squeezed. The description of this forthcoming squeezing action is detailed in a series of successive steps for a better understanding of how the deployment device 200 operates, infra, as shown in FIGS. 22a-26g. However, in a preferred embodiment, this squeezing motion/action occurs all in one squeezing motion/action.

Figure 34:
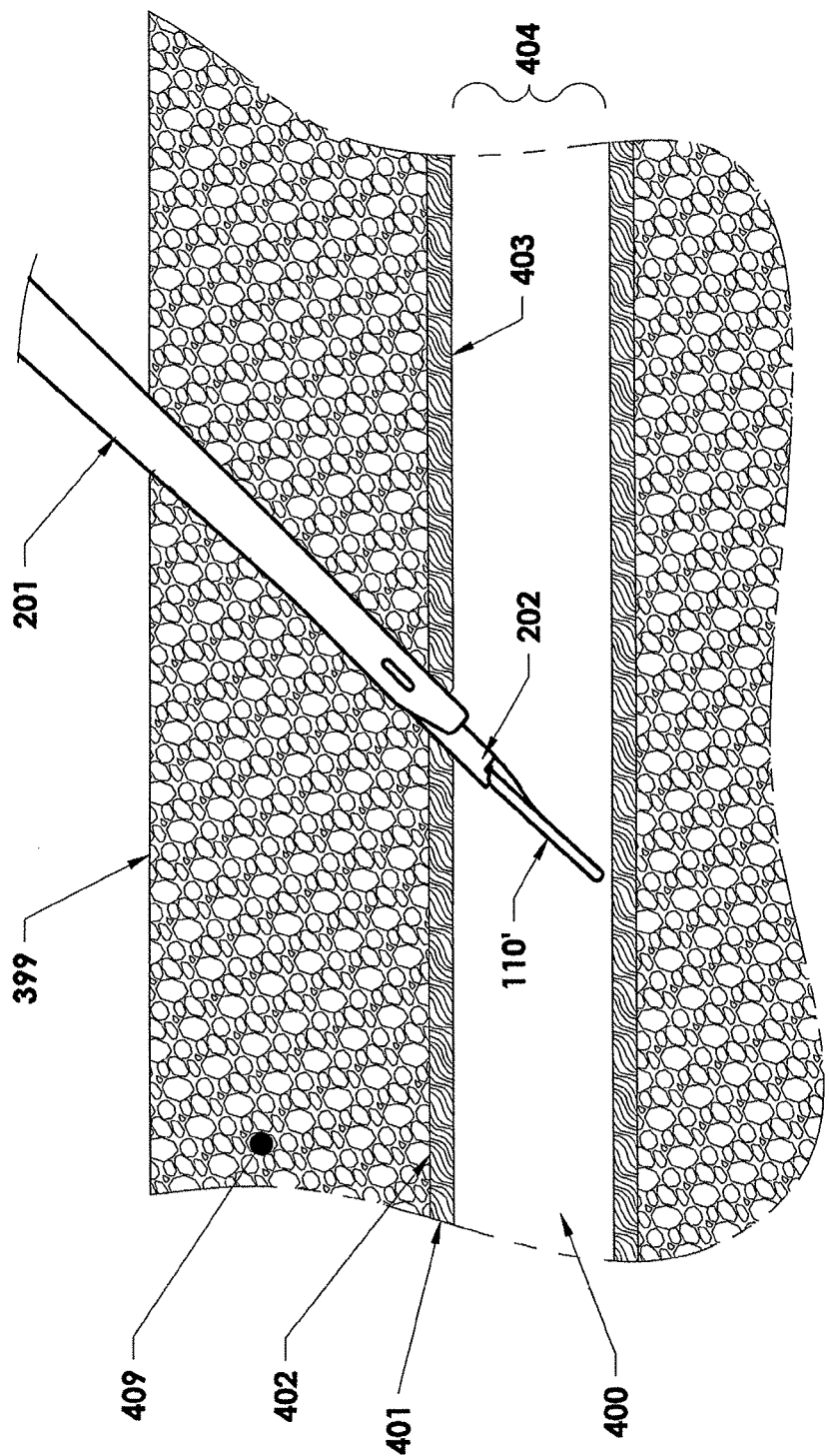
Figure 35:
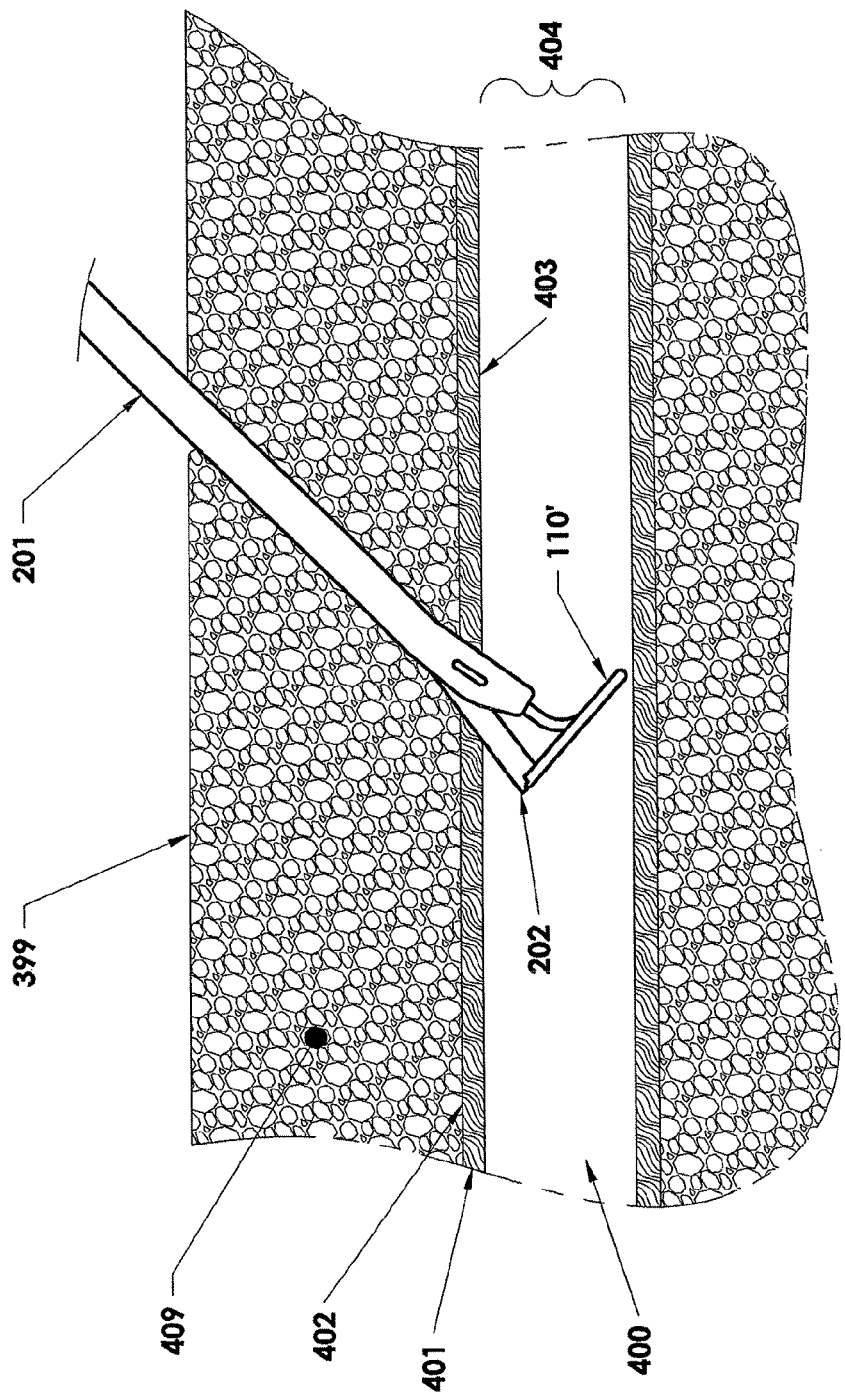
Figure 36:
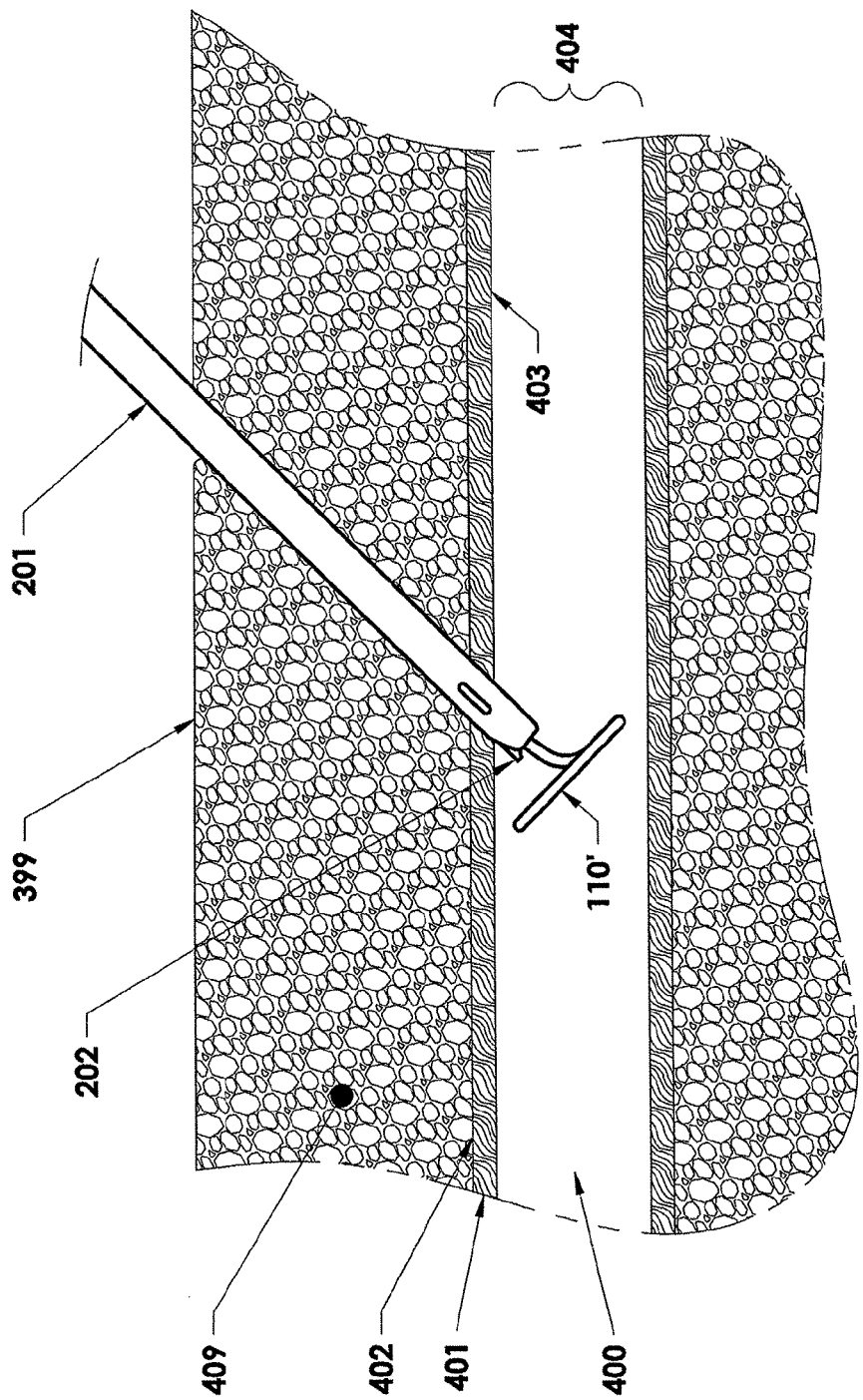
Figure 37:
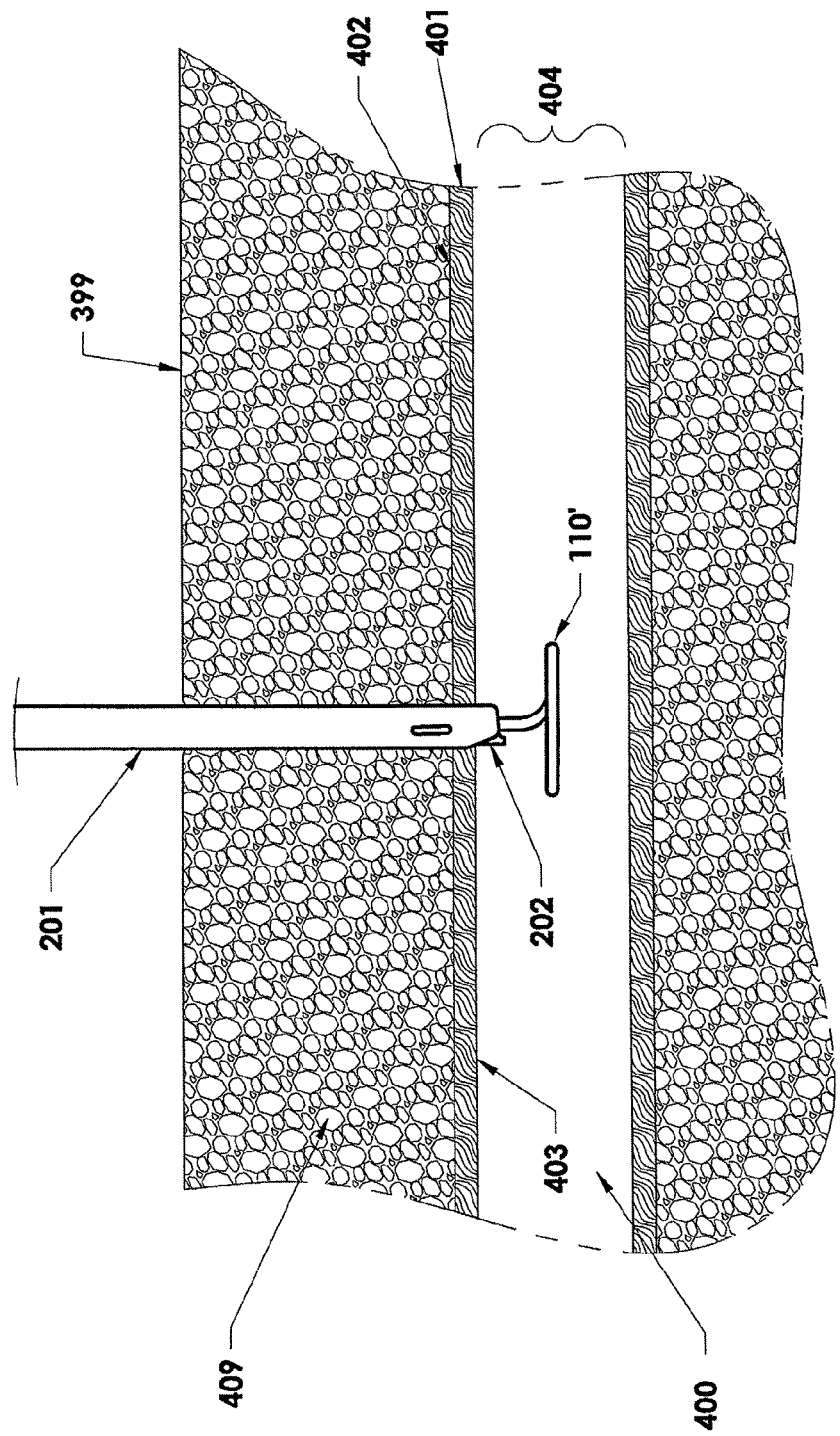
Figure 38:
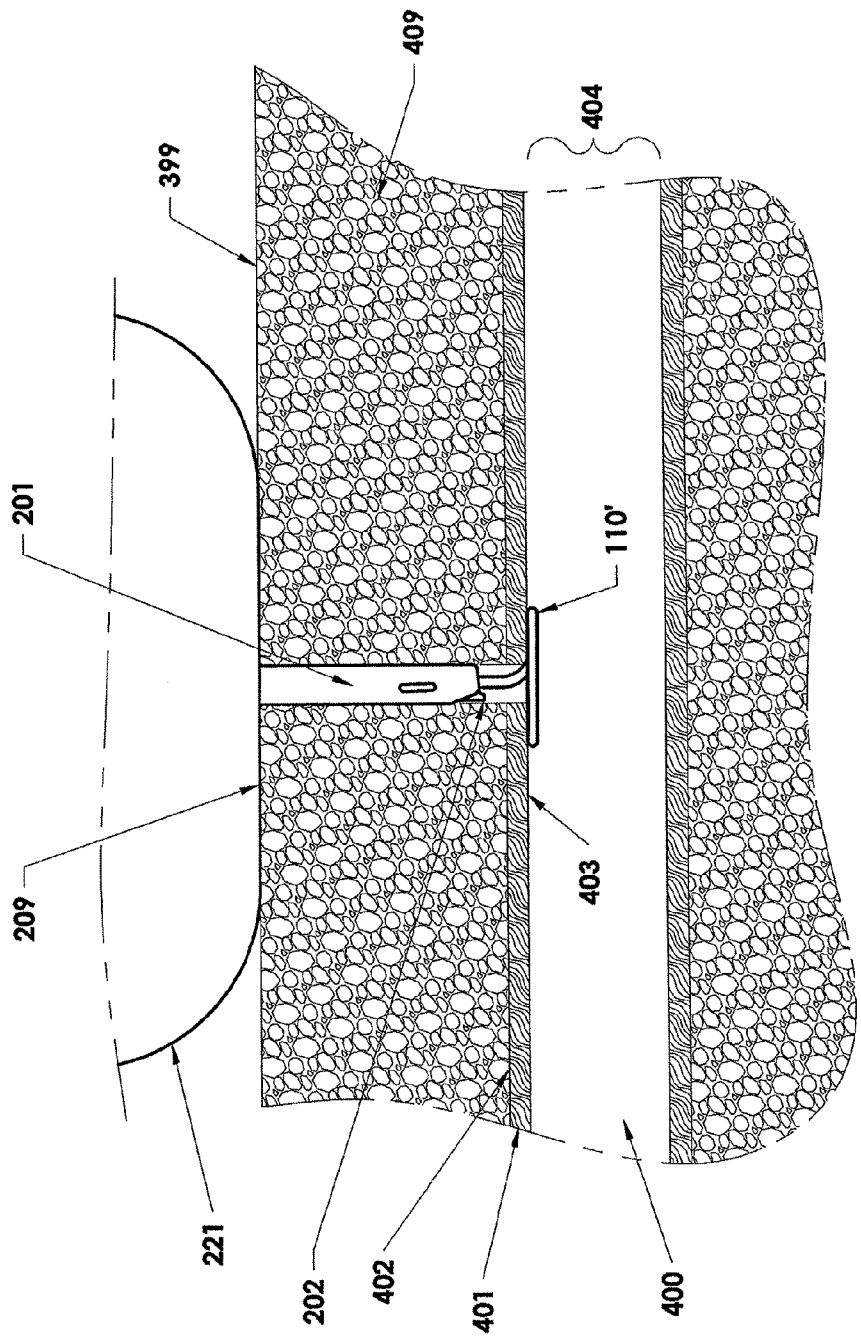

Turning to FIGS. 22a-22e, the squeeze lever handle 232 is squeezed such that the slide barrel 215 is moved proximally via the link 235 which is hingedly attached to both the squeeze lever handle 232 and the slide barrel 215. The slide barrel's 215 squeeze finger catch tabs 217 are in frictional contact with the outer proximal tube's 211 catch tabs 220 such that the outer proximal tube 211 is pulled proximally. The outer distal C-tube 201 is slid proximally with respect to the inner distal C-tube 202, thus exposing the footplate 110 on the inside of the lumen 404 of the vessel 400. (See also FIG. 34, showing the exposure of the footplate 110' within the lumen of the blood vessel.)

Turning to FIG. 23a-23e, the squeeze lever handle 232 is further squeezed such that the slide barrel 215 moves further proximally via the link 235 (which is hingedly attached to both the squeeze lever handle 232 and the slide barrel 215) (see FIG. 23a). Proximal movement of the slide barrel's 215 squeeze finger catch tabs 217 (engaged with the outer proximal tube's 211 catch tabs 220) (see FIG. 23d) results in further proximal movement of the outer proximal tube 211. This further proximal movement of the outer proximal tube 211 creates engagement of the outer proximal tube's push tabs 223 with the distal surface 253 of the wire ferrule 250 (see FIG. 23c). The proximal movement of the wire ferrule 250 translates into proximal movement and force (tensile load) applied to the wire 120. This force actuates the footplate 110' (which has a stable pivot/hinge point provided by the undercut feature 208 on the distal end of the inner distal C-tube 202) to a substantially perpendicular position relative to the longitudinal axis of the control housing 210 inside the vessel 400 (see FIGS. 23e & 35). The embodiments of the footplate that are related to the monolithic footplate and the footplate comprising more than one part that are permanently fixed to each other, and permanently deform (plastically deform) due to this applied tensile load. The embodiments of the footplate related to the hinge and ball-and-socket mechanisms, do not plastically deform, but rotate into the actuated position due to the applied tensile load. At the end of the proximal travel of the wire ferrule 250, the proximal snap finger 243 of the outer proximal tube 211 locks with the snap feature 260 of the control housing 210 (see FIG. 23c). Further, the wire ferrule's proximal snap finger 254 engages with the cap finger 242 such that the wire ferrule 250 is locked in its fully proximal position (see FIG. 23c).

Turning to FIGS. 24a-24f, the squeeze lever handle 232 is further squeezed such that the slide barrel 215 moves further proximally via the link 235 (which is hingedly attached to both the squeeze lever handle 232 and the slide barrel 215) (see FIG. 24a). As the slide barrel 215 moves proximally, the outside radiused portion 270 of the squeeze fingers 269 at the distal portion of the slide barrel 215 come into frictional contact with a reduced-width region 273 in the cut-out 261 in the top portion of the control housing 210 (see FIG. 24e). The two squeeze fingers 269 are squeezed together (elastically deformed, each in an inward direction) until there is complete disengagement of the squeeze finger catch tabs 217 from the catch tabs 220 of the outer proximal tube 211 (see FIG. 24f). This proximal movement of the slide barrel 215 creates contact of the proximal end of the slide barrel 244 with the release shaft 239 (see FIG. 24d). Consequently, the release shaft 239 is moved proximally such that the release shaft's proximal end 245 comes into frictional contact with the radiused feature 246 of the cap finger, right 241. The cap finger, right 241 is elastically deformed in an outward direction such that the distal end of the cap finger, right 241 becomes disengaged from the proximal end 262 of the inner proximal tube 213 (see FIG. 24c).

Turning to FIGS. 25a-25d, the squeeze lever handle 232 is further squeezed such that the slide barrel 215 is moved further proximally via the link 235 (which is hingedly attached to both the squeeze lever handle 232 and the slide barrel 215) (see FIG. 25a). At this point in the actuation process, the slide barrel is engaged with neither the inner nor the outer proximal tube. Rather, this step simply offsets the sequence timing of the relative movement of the inner proximal tube 213 and the outer proximal tube 211. At the end of this step, the proximal surfaces of the push features 248 on the proximal end 244 of the slide barrel 215 are in frictional contact with the distal surfaces of the catch tabs 263 of the inner proximal tube 213.

Turning to FIG. 26a-26g, the squeeze lever handle 232 is further squeezed such that the slide barrel 215 moves further proximally via the link 235 (which is hingedly attached to both the squeeze lever handle 232 and the slide barrel 215) (see FIG. 26a). At the end of this squeezing motion, the squeeze lever handle 232 is disallowed from being further squeezed owing to a box-shaped feature 265 protruding upwards from the slide button 233 (which is slidably attached to the squeeze lever handle 232) coming into frictional contact with the underside of the control housing 210 (see FIGS. 26d & 26g). During the squeezing motion, the proximal surfaces of the push features on the proximal end 248 of the slide barrel 215 push the inner proximal tube (via the distal surfaces of the catch tabs 263 of the inner proximal tube 213) in a proximal direction (see FIG. 26c) to the inner proximal tube's 213 full and final proximal position. At the end of this step, the snap fingers 264 of the inner proximal tube 213 are locked with the catch features 259 of the control housing 210 (see FIG. 26e). Also at the end of this step, the snap fingers 249 of the squeeze lever handle 232 have snapped into the primary undercut features 258 on the outside of the control housing 210 (see FIG. 26g). At this point, the inner distal C-tube 202 has been moved in the proximal direction (to its fully-most proximal position) such that it is completely detached from the footplate 110', leaving the footplate 110' completely exposed within the lumen 404 of the blood vessel 400 (see also FIG. 36). This squeezing action also disconnects the lateral upper hook-shaped ends 237 of the squeeze lever handle 232 (on both the left and right sides of the device) from the hook features 255 on the proximal end of the skin flange assembly 222, thereby releasing the skin flange assembly 222, which moves in the distal direction until the distal surface 209 of the distal portion 221 of the skin flange assembly 222 contacts the outside surface of the patient's skin 399 (see also, FIG. 38). The distal movement of the skin flange assembly 222 is due to a constant distal force created by the lateral constant force springs 125 (on the left and right sides of the control housing 210). As the skin flange assembly 222 is moving in a distal direction, but prior to the distal surface 209 of the distal portion 221 coming into contact with the outside surface of the patient's skin 399, the user may vertically orient the deployment device 200 to a substantially perpendicular position with respect to the plane of the surface of the patient's skin 399 (see FIG. 37). This vertical orientation of the deployment device 200 creates a planar relationship between the distal surface 209 of the distal portion 221, and the outside of the patient's skin 399 such that an approximately even contact pressure exists between the planar interface of the distal surface 209 of the distal portion 221 of the skin flange assembly 222, and the outside of the patient's skin 399 (see FIG. 38). A rotary damping system 225 (see FIG. 27), which comprises a rack and pinion configuration, may be provided to provide a force to the skin flange portion in opposition to the distal force exerted by the lateral constant force springs, which partially resists, but does not fully negate, the constant distal force. This rotary damping system 225 serves to maintain an appropriately low velocity of the skin flange which offers two benefits; (1) it allows the user time to vertically orient the deployment device 200 (as discussed supra) and, (2) it minimizes the impact force at the moment that the distal surface 209 comes into contact with the outside of the patient's skin 399. Once the distal surface 209 of the distal portion 221 of the skin flange assembly 222 is in contact with the skin 399 of a patient, it applies a constant distal force to the skin 399 which, in turn, creates a tensile proximal force in the wire 120, which seats the footplate 110' against the inside of the vessel wall 403. A datum is created at the point where the footplate is seated (see also, FIG. 38). At this point, the distal ends of both the outer distal C-tube 201 and the inner distal C-tube 202 have been moved in the proximal direction to a position proximal (outside) of the outside surface 402 of the blood vessel wall 401 of the blood vessel 400 (see FIG. 38).

Turning successively to FIGS. 28a-28b, the slide button 233 is slid in a distal direction, which allows the squeeze lever handle 232 to be free for further squeezing in the next step. When the slide button 233 has been actuated (slid distally), the box-shaped feature 265 is placed in a distal position such that it is free (from mechanical interference) to enter a rectangularly-shaped opening 273 in the bottom side of the control housing 210. The entrance of the box-shaped feature 265 into the rectangularly-shaped opening 273 does not occur until the next step during further squeezing of the squeeze lever handle 232.

Turning to FIG. 29a-29f, the squeeze lever handle 232 is further squeezed a final time, to its fully-most squeezable position. In accordance with the distal movement of the slide button 233 (as described supra), the box-shaped feature 265 (protruding upwardly from the slide button 233), is allowed to protrude into the rectangulary-shaped opening 273 in the bottom of the control housing 210, during the final squeeze, thus allowing the squeeze lever handle 232 (to which the slide button 233 is slidably attached) to come to its final, fully-most squeezed position (see FIGS. 29a & 29d). At the end of this step, the snap fingers 249 of the squeeze lever handle 232 snap into the secondary undercut features 275 on the outside of the control housing 210 (see FIG. 29c). This final squeeze releases the slide barrel 215 at the lower hinge pin 256 from the C-feature 266 on the proximal end of the link 235. The C-feature 266 is stripped from the lower hinge pin 256 via cam-action of the centrally located cam features 267 of the link 235 with the underside (outside surface) 257 of the control housing 210 (see FIG. 29e). Immediately upon disassociation of the link 235 from the slide barrel 215, the slide barrel 215 moves distally under the force of the upper and lower constant force springs 135 (see FIG. 29a). As the slide barrel 215 moves in a distal direction, so does the push tube 212, the push tube insert 112, and the plug 111. The plug 111 moves over the wire 120, while remaining concentric with the wire 120, and rotationally aligned with the wire 120 and the footplate 110'. When the distal end 104 of the plug 111 comes into proximity of the proximal margin 113 of the footplate 110', motion ceases (see FIG. 29f). In accordance with an embodiment with the present invention, the distal C-tubes locally expand and disassociate creating an irreversible un-nested condition that allows passage of the plug 111 into the post-vascular deployment configuration and position, wherein the plug 111 comprises a proximal diameter which is larger than an inner diameter of the main conduit area 205. The distal C-tubes remain disassociated (un-nested) from one another after the plug 111 has traveled (proximal-to-distal) through the longitudinal length of the distal C-tubes (see FIG. 9d). At the end of the distal movement of the slide barrel 215, the cut-off lever 218 flips up as a result if its distal, underside portion coming into contact with the ramp features 277 on the top side of the control housing 210 (see FIG. 29a).

Figure 39:
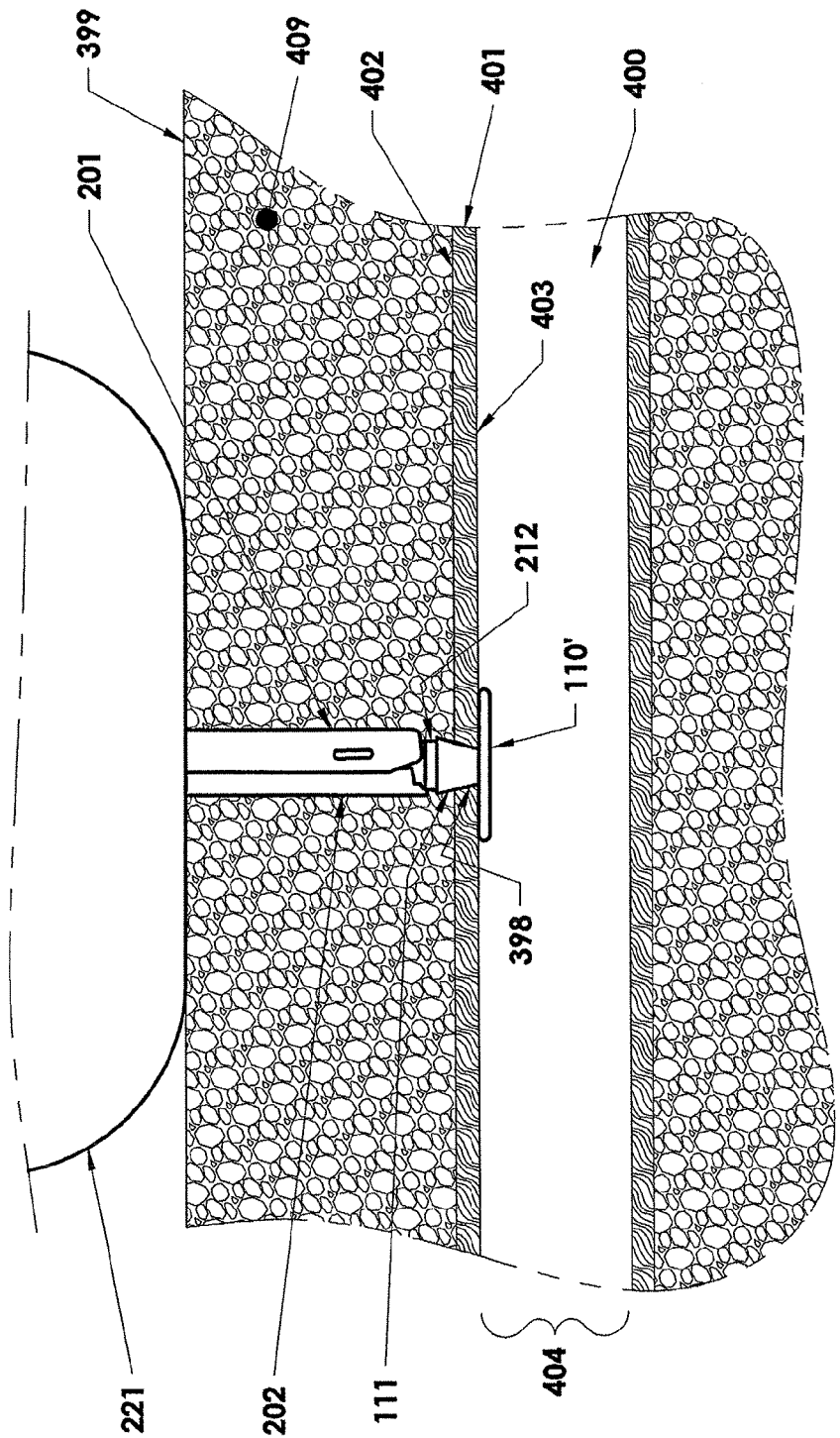

As shown in FIG. 39, at the end of this step, the plug 111 has entered the arteriotomy 405, and the plug 111 and the footplate 110' are in their final positions relative to one another, and the vessel wall 401 (a post-deployed closure device deployment configuration and position, as described infra). The post-deployed closure device deployment position (in the distal-proximal direction) is controlled by the datum that was created, as discussed supra.

Figure 40:
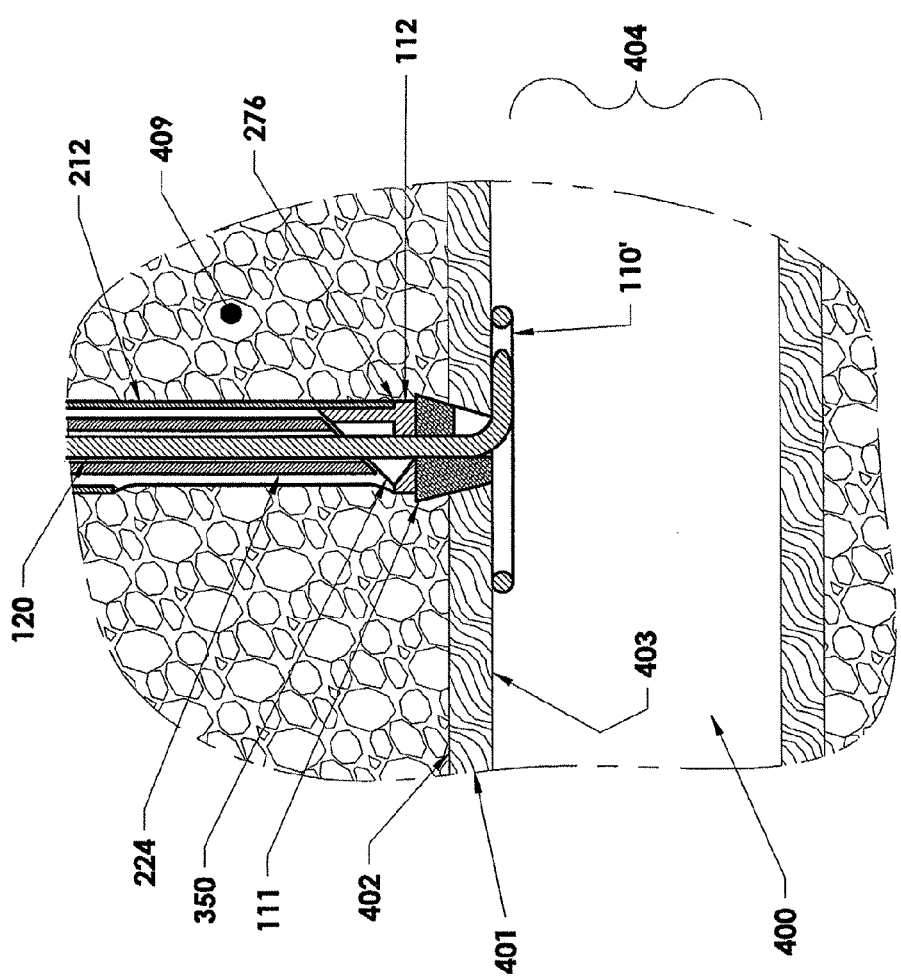
Figure 41:
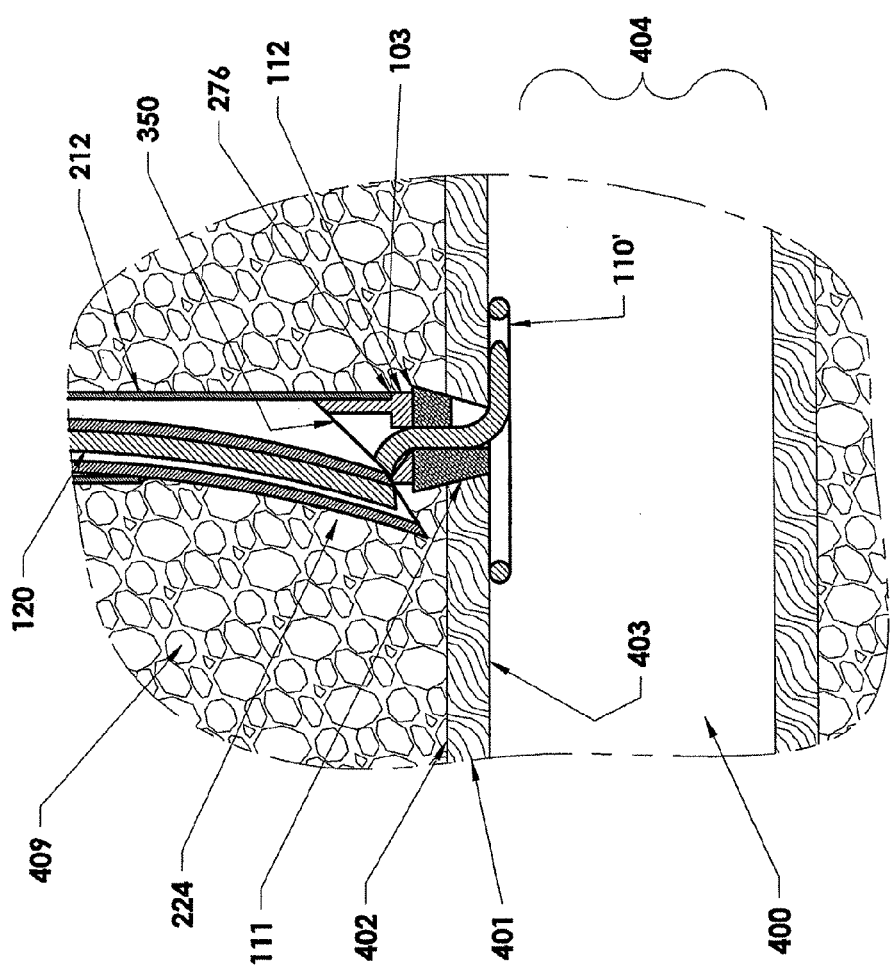

Turning to FIGS. 30a-30c, the distal portion of the cut-off lever 218 is pulled up in a direction perpendicularly away from the longitudinal axis of the wire, by the user. During the cut-off procedure, the cut-off lever 218 rotates about a hinge pin 238, co-located with a through-hole 274 at a proximal margin of a proximal extension on the slide barrel 215. The contact surface 310 at the underside of the cut-off lever 218 comes into frictional contact with the most proximal surface 315 of the cap 240 at the proximal end of the shear tube 224. The shear tube 224 is driven in a distal direction owing to the cam-action imparted by the contact surface 310 of the cut-off lever 218. As the shear tube 224 is displaced distally over the static (stationary) wire 120, the angled, distal end 312 of the shear tube 224 is placed in high contact force with the angled proximal surface 350 of the push tube insert 112 (which is resisting the distally directed force being applied to the shear tube 224). A scissor-type shearing force is applied to the wire 120 at a position just slightly proximal of the proximal end 103 of the plug 111, as the angled distal surface 312 of the shear tube 224 slides over (and past) the angled proximal surface 350 of the push tube insert 112. When the ultimate shear strength of the wire 120 has been exceeded, the wire material fails (disassociates). Simultaneously, the short remaining wire section that is left protruding proximally from the proximal end 103 of the plug 111, is bent in the direction of the movement of the shear tube 224 (see FIGS. 30c & 41). The bend that is created in the wire is sufficient to lock the relative positions of the plug 111 and the footplate 110' in order to provide a stable and secure final implant construct. Details of the cut off system are shown in FIG. 40 (the pre-cut/pre-bent configuration)—including the shear tube 224 and wire 120. The cutting and bending of the wire 120 by the shear tube 224 (the post-cut/post-bent configuration) is shown in FIGS. 30c and 41. The deployment device 200 may then be removed from the percutaneous puncture and disposed of in a proper medical waste container.

Figure 42:
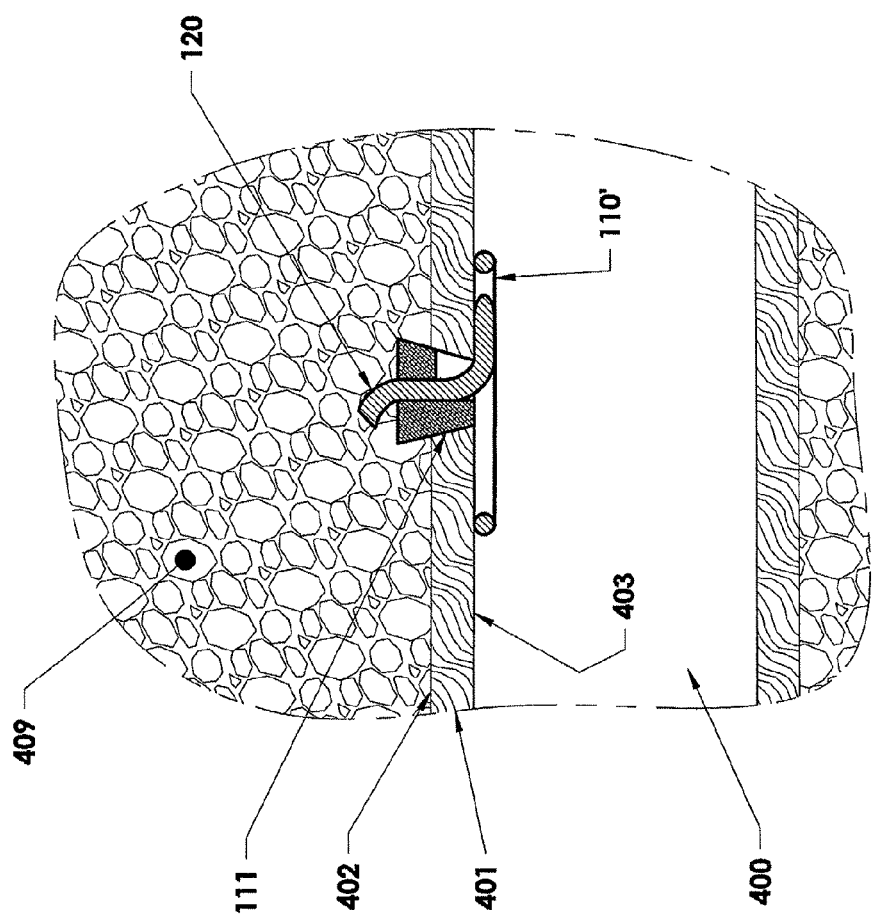
FIGS. 42-43 show a closure device in a sealing relationship with the opening formed through a blood vessel (i.e., post-closure device deployment configuration and position), according to an embodiment of the present invention.
Figure 43:
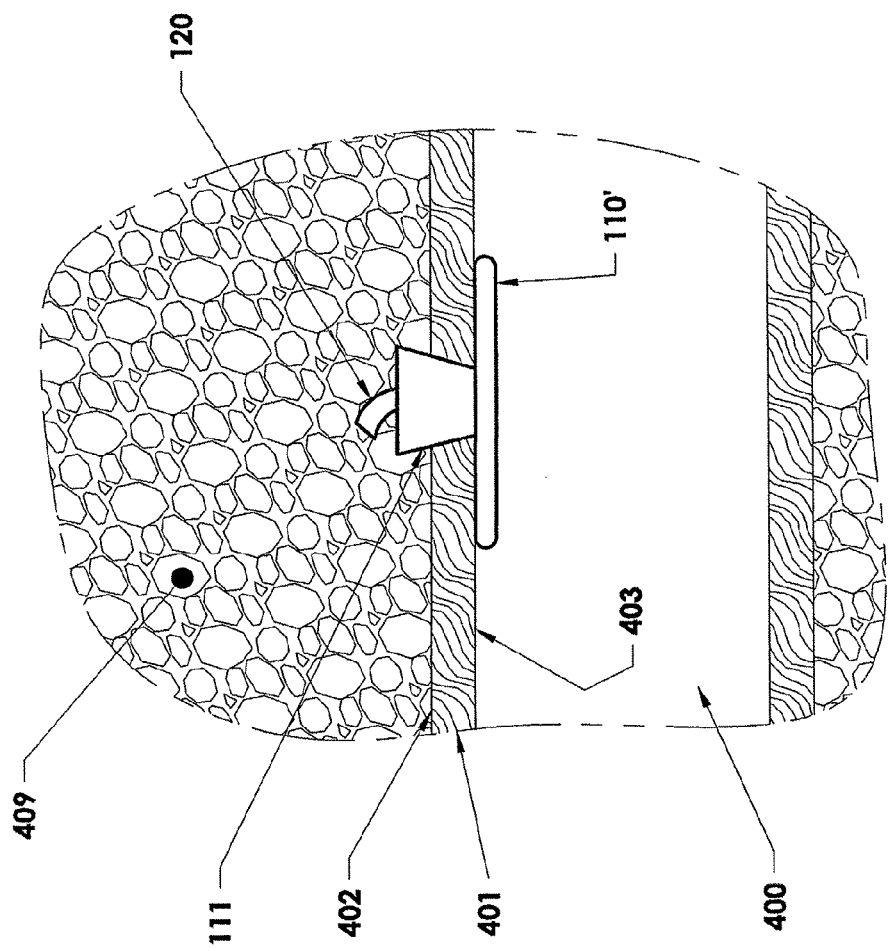

Turning to FIGS. 42 & 43, the closure device's 100 post-deployed closure device deployment configuration and position will now be described. This configuration and position can include any of the various embodiments of the footplate as described supra. The discussion of the closure device's 100 post-deployed closure device deployment configuration and position, however, will specifically refer to footplate 110' (with plug 111 and wire 120), as an example of this configuration and position with brief references to some of the other footplate embodiments.

In accordance with an embodiment of the present invention, during the method of deploying the closure device 100 of an embodiment of the present invention as described supra, the plug 111 is pushed through the main conduit area 205 and over the proximal portion of the wire 120 as the footplate 110' rests against the inner wall 403 of the vessel 400 in its post-deployed closure device deployment configuration and position. Additionally, the plug 111 is pushed percutaneously into the puncture, down through the tissue tract and into the arteriotomy. The plug's 111 distal portion 104 extends through the vessel wall over the distal portion of the wire 120 and into contact with the footplate 110' at the proximal leg 34', at about the common plane established by the elongated U-shaped loop 30' and the arcuately-curved connecting portion 33'. (In the closure device embodiment comprising footplate 110, for example, the distal portion 104 of the plug 111 pinches (traps) part of the artery wall at the margin of the arteriotomy 405 (drawing this part of the artery wall and holding it) as it nests itself within the U-shaped looped portion 30 of the footplate 110, where the distal end 104 of the plug 111 can reside slightly distal of the inside surface of the vessel wall 403 (within the lumen 404 of the blood vessel 400)). The portion of the footplate 110' that is seated against the inside wall 403 of the artery comprises the elongated U-shaped loop 30'. The wire 120 of the footplate 110' extends through the axial hole 105 in the plug 111 in a proximal direction, where the wire 120 is bent at an acute angle in a direction away from a longitudinal axis of the plug's axial hole 105 at the proximal end 103 of the plug 111. The proximal portion 103 of the plug 111 resides outside the wall 401 of the artery in the tissue tract. Alternatively, the entire plug may reside within the arterial wall. Generally, the diameter of the proximal portion 103 of the plug 111 is larger than the opening in the wall of the blood vessel (the arteriotomy 405) at the radial interface between the arteriotomy 405 and the proximal portion 103 of the plug 111. In this post-deployed closure device deployment configuration and position, the closure device's 100 seal is formed by the radial interface of the plug 111 and the arteriotomy 405. (In the closure device embodiment comprising footplate 110, for example, the vessel wall tissue that was drawn into the looped portion (and supported by the footplate 110) can also help form the seal of the closure device 100.) The mechanism of retention (locking) of the closure device 100 comprises the portion of the wire 120, which is proximal to the plug 111, that was cut and bent (by the action of the cut-off lever 218 of the deployment device 200, as described supra) to secure the plug 111 and footplate 110' together in conjunction with the footplate's 110' substantially parallel configuration with respect to the inside wall 403 of the blood vessel. This mechanism of retention allows the footplate 110' to resist passage back through the arteriotomy 405, in a proximal direction. Likewise, this mechanism of retention aids in preventing the plug 111 from migrating (passing) completely through the arteriotomy 405, in a distal direction. Hence the closure device 100 (the final implant construct) is stable, i.e. locked, as to resist dislodgement in vivo in either the distal or proximal direction.

The same basic post-deployed closure device deployment configuration and position can be established with any of the embodiments of the footplate, as described supra. For instance, the portion of the footplate that can be seated against the inside wall of the blood vessel (and is in contact with the distal portion 104 of the plug 111) comprises, for example; the elongated U-shaped loop 730 for footplate 710 (see FIG. 1f), where the plug's 111 distal portion 104 extends through the vessel wall over the distal portion of the wire 120 and into contact with the footplate 710 at the proximal leg 734, at about the common plane established by the elongated U-shaped loop 730 and the arcuately-curved connecting portion 33. In the embodiments where the footplate is represented by a longitudinally shaped bar (e.g., footplates 810, 910, 1010, 1110, and 1210) either the top or bottom surface of the footplate is seated against the inside wall of the blood vessel. For example, the bottom arcuately-shaped surfaces of footplates 810 and 1010 (see FIGS. 1g, 1h, 1i, and 1j) are seated against the inside wall of the blood vessel; or the substantially planar top surfaces (938 and 1138) of footplates 910 and 1110 respectively (see FIGS. 1k, 1l, 1m, and 1n) are seated against the inside wall of the blood vessel; or the bottom substantially planar surface 1243 of footplate 1210 (see FIGS. 1o and 1p) is seated against the inside wall of the blood vessel.

The following description relates to alternative embodiments of the closure device implant and the closure device delivery device (or deployment device) of the present invention, parts of which may be substituted with parts previously discussed. The alternative embodiments include alternate and sometimes additional components, however, some of the alternative embodiments function in a similar manner. Thus, much of the discussion set forth above with respect to previous embodiments with respect to functionality, and the discussion set forth above with respect to some of the basic parts of the implant and the deployment device, apply to the alternative embodiments discussed below.

Figure 44:
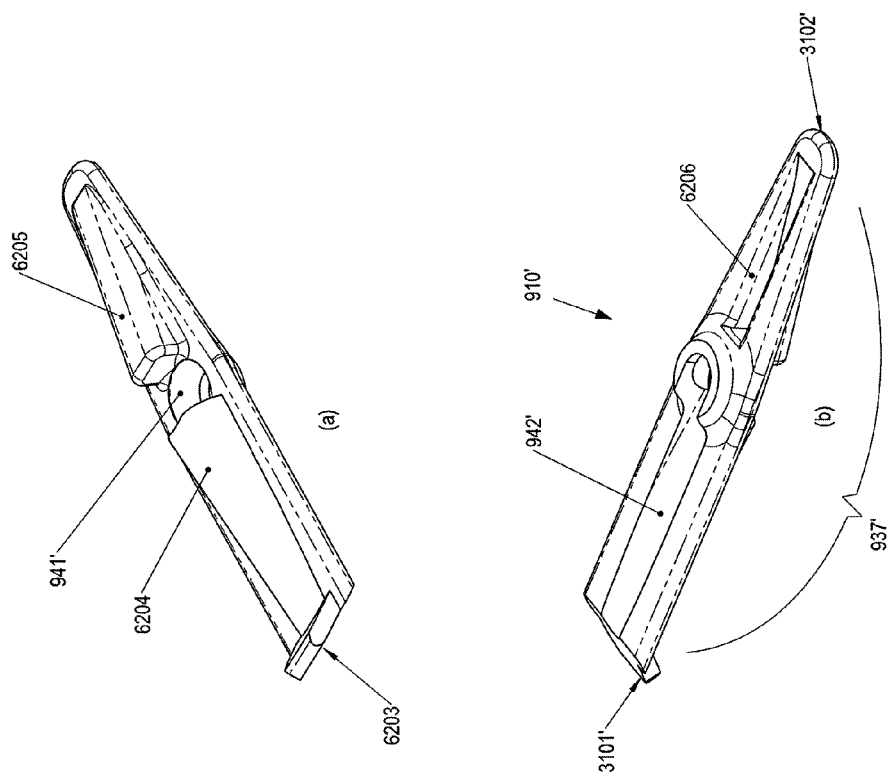
FIGS. 44 a-b show a bottom perspective view and top perspective view of a footplate, according to an alternative embodiment of the present invention.
Figure 61:
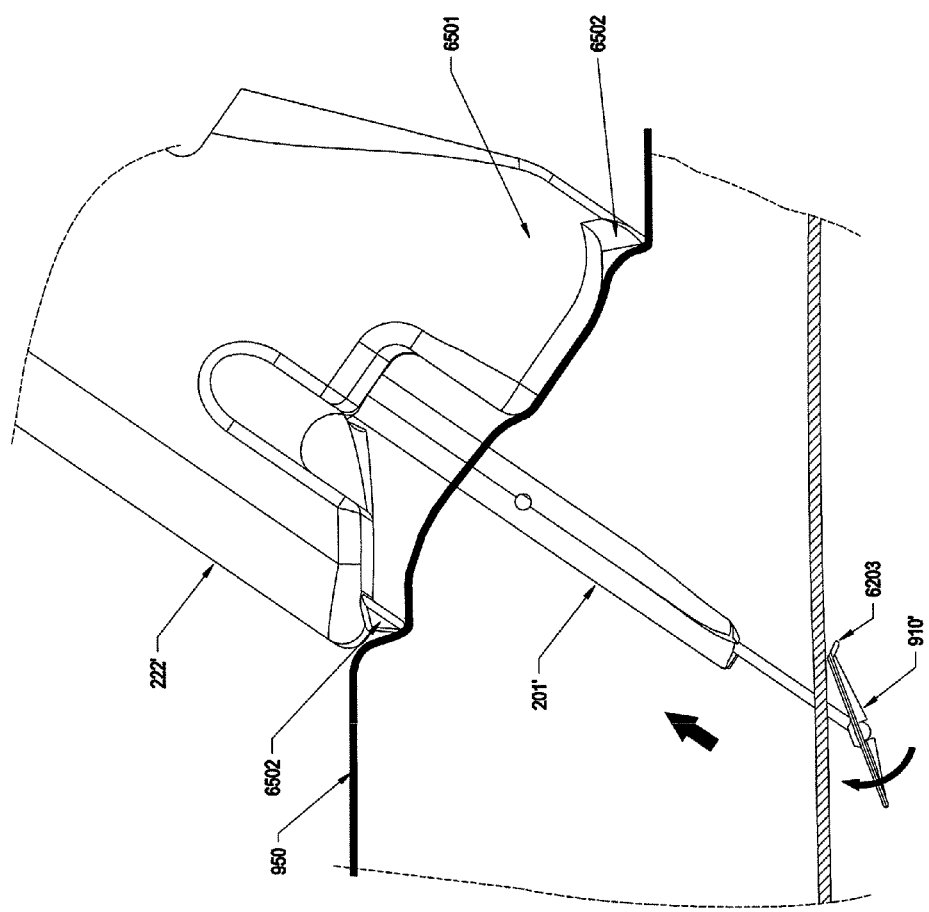
FIG. 61 shows the skin flange, and other distal portions of the deployment device, in use and in a nearly fully deployed position, according to an alternative embodiment of the present invention.

As previously discussed with respect to embodiments of the closure device implant, the closure device implant includes a footplate, a wire, and a plug. Turning to FIGS. 44a-b, a bottom perspective view and top perspective view of a footplate 910' are shown, respectively. FIGS. 44a-b show footplate 910' in a pre-deployed closure device deployment configuration and position, wherein the footplate 910' is within a distal end of a deployment device 200' (not shown). The footplate 910' comprises a longitudinally shaped block or bar 937'. The bar 937' comprises a proximal end 3101' and a distal end 3102'. A wire channel 942' and a wire ball socket 941' are also shown. Turning now to FIG. 61, the proximal end includes a transom 6203, a ramp-like feature which acts much like a ski-tip such that as the wire and footplate are retracted proximally during deployment, the transom feature contacts the inside surface of the artery wall causing the footplate to articulate to an approximate right angle to the wire. Turing back now to FIG. 44, the wire channel 942' is made up of a wire channel wall 6204, a semi-circular, pipe-like feature the diameter of which closely conforms to the wire. The wire channel 942' can be set on an axis that is six degrees from the primary axis of the footplate thereby precluding a footplate-to-wire orientation which may prevent the transom 6203 from reliably articulating the footplate relative to the wire during deployment as described supra. A ball lock 6205 feature precludes the wire ball-shaped end 936' from dislocating from the footplate's wire ball socket 941' (see also FIG. 45) while the footplate is in its default configuration, that is, parked inside the sheath. A ball lock core 6206 feature maintains an approximately consistent wall thickness (for effective corrosion and manufacturability).

Figure 45:
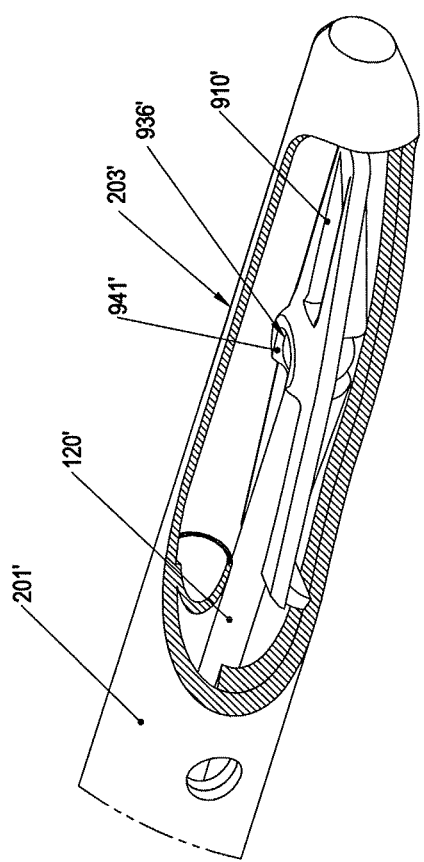
FIG. 45 shows a ball-shaped end on a distal tip of wire connected at a wire ball socket of a footplate, according to an alternative embodiment of the present invention.
Figure 46:
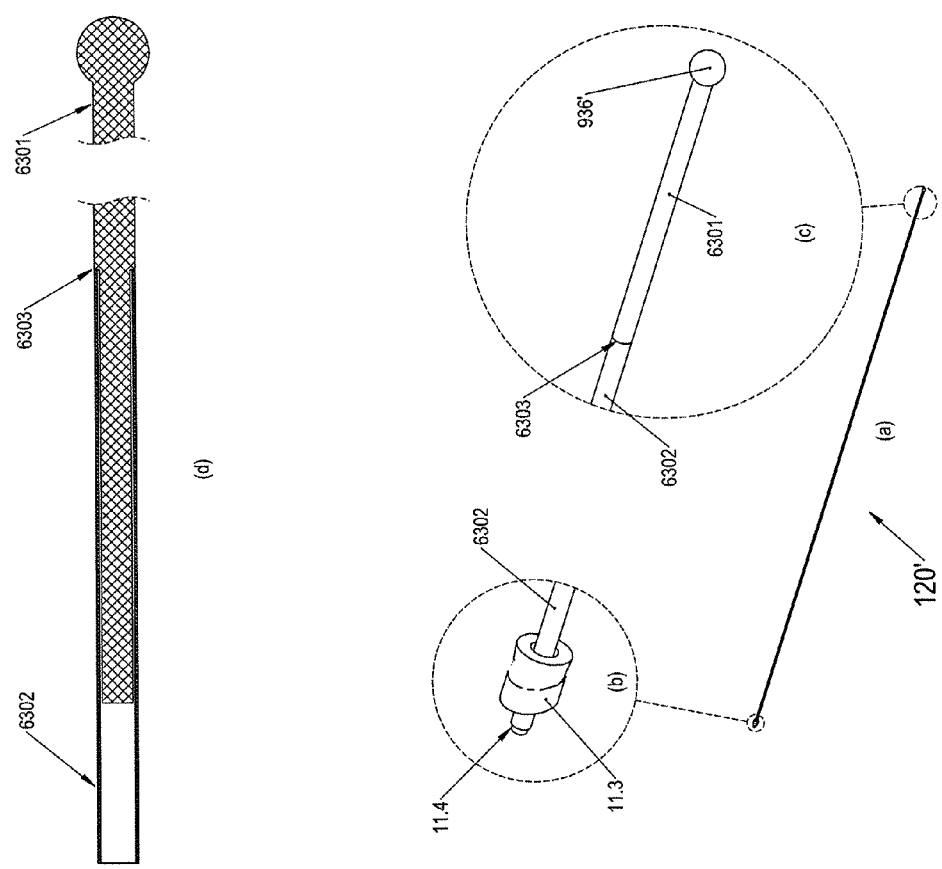
FIGS. 46 a-d show various views of a wire assembly, according to an alternative embodiment of the present invention.

As shown in FIG. 45, a ball-shaped end 936' on a distal tip of wire 120' is connected at the wire ball socket 941' of the footplate 910' (see also FIGS. 46*a-c*). The ball-shaped end 936' is actually positioned inside the footplate 910' at the wire ball socket 941'. In a pre-deployed closure device deployment configuration and position, wire 120' stretches proximally from the wire ball socket 941', through the wire channel 942' within a distal tip 203' of a sheath assembly, and through the sheath 201'. The wire 120' can be comprised of a magnesium alloy wire 6301 section and a stainless steel tube 6302 section the outside diameters of which are identical and consistent along their length. The two sections are connected via a joint 6303, as depicted in FIG. 46, consisting of a smaller diameter step in the wire 6301 section inserted into the tube 6302 section and joined via adhesive, swaging, crimping, welding or other technique. The very proximal end of the tube 6302 is terminated with a ferrule 11.3 which can be crimped in place via a crimping tool and is accurately and precisely located so as to properly locate the plug once deployed to the footplate. The crimp strength is improved via the use of a solid wire insert 11.4 to prevent crushing of the tube 6302 at the location of the ferrule 11.3.

Figure 47:
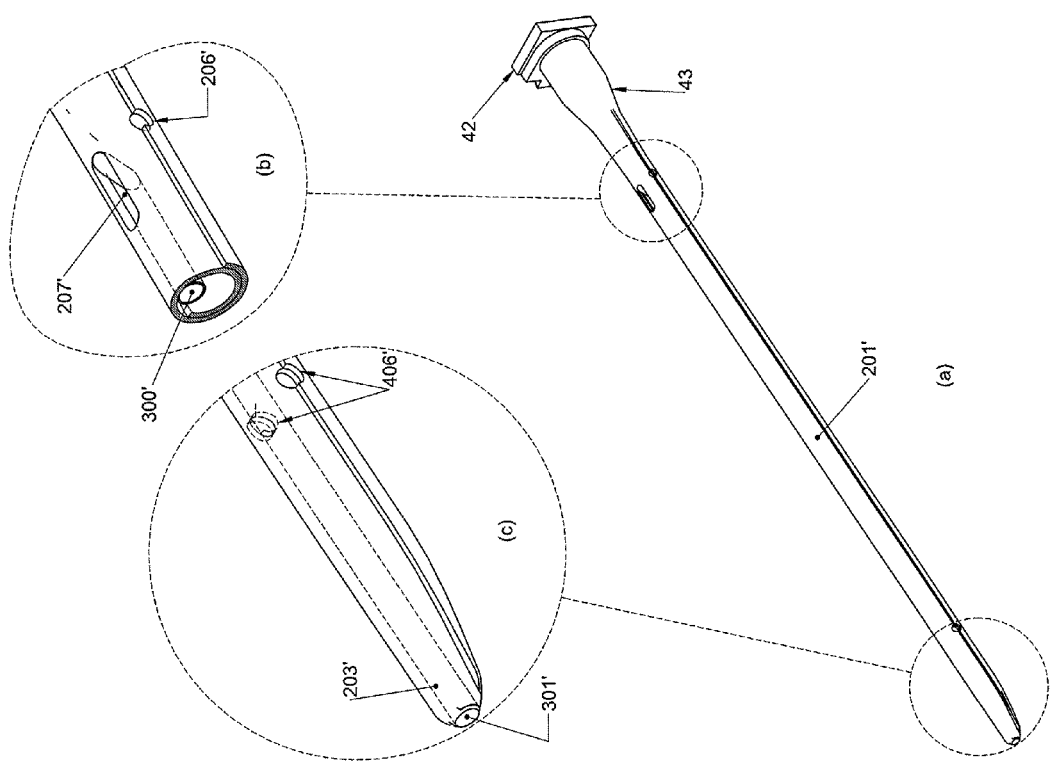
FIGS. 47 a-c show various views of a sheath assembly, according to an alternative embodiment of the present invention.

As shown in FIGS. 47*a-c*, various views of portions of the sheath assembly according to an alternative embodiment are shown. The sheath assembly includes one or more of the following: a sheath 201', sheath extension 42, sheath loft 43, distal tip 203', guide wire entrance 301', blood inlet holes 406', guide wire lumen 300', guide wire exit 207', and a blood exit hole 206'. As shown in FIG. 47*b*, the sheath is comprised of a dual lumen extrusion, the larger lumen of which is slit longitudinally and then heat-formed to fold over itself thereby minimizing its diameter. The smaller lumen is intended for the insertion of a guidewire and its outside diameter limits the minimum folded diameter of the larger lumen.

Figure 48:
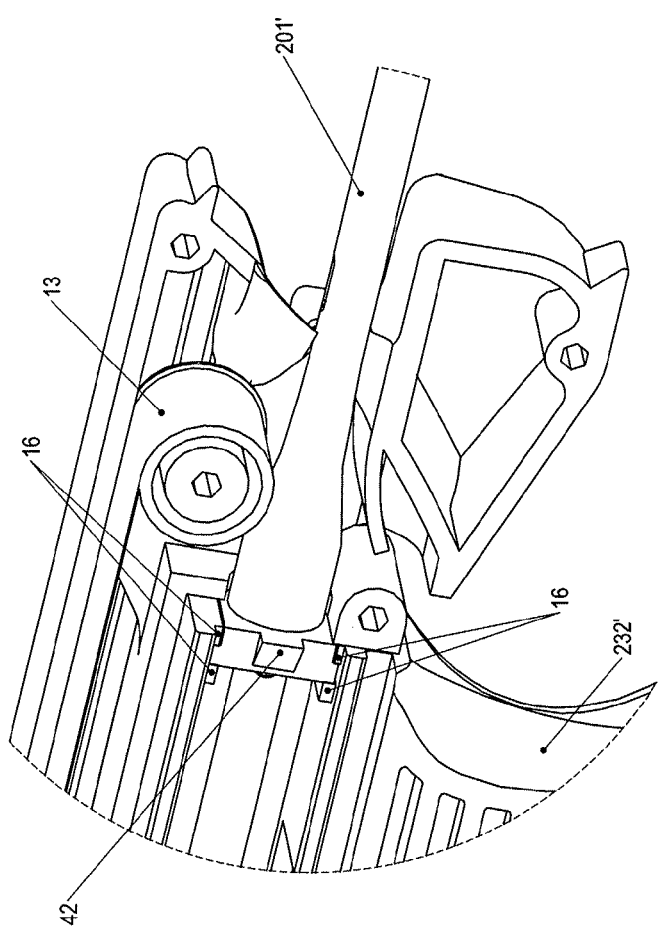
FIG. 48 shows the finger pull/sheath interface, according to an alternative embodiment of the present invention.
Figure 49:
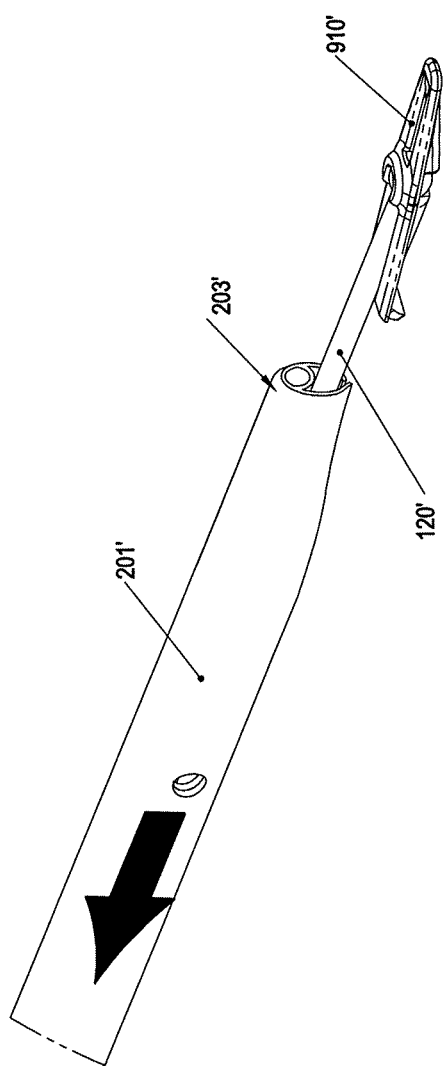
FIG. 49 shows the retracted sheath and exposed footplate, according to an alternative embodiment of the present invention.

As shown in FIG. 48, the sheath assembly 201' is connected at its proximal end to the finger pull 232' via the interface of the sheath extension 42 and the sheath assembly socket 16. During use of the deployment device 200' as further described infra, when the finger pull 232' travels proximally it moves the sheath assembly 201' with it. The finger pull 232' also retracts the distal tip 203' of sheath assembly 201' away from the footplate 910', thereby exposing the footplate 910' (see FIG. 49).

Figure 50:
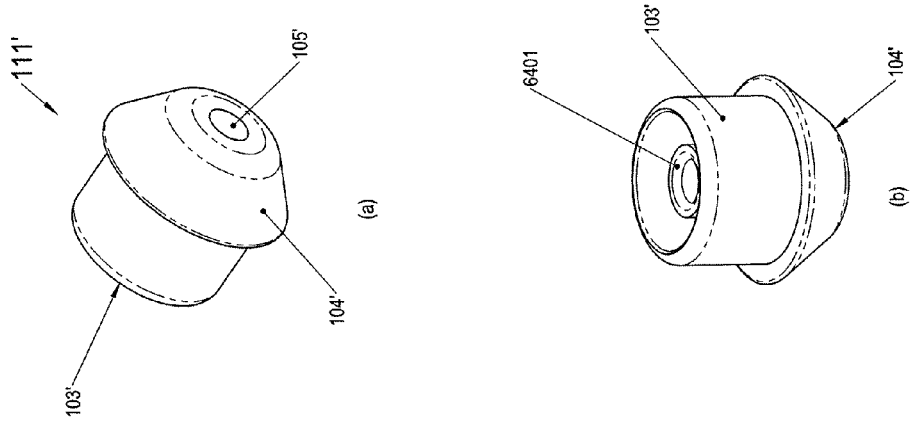
FIGS. 50 a-b show various views of the plug, according to an alternative embodiment of the present invention.

Turning to FIGS. 50*a-b*, a plug 111' according to an alternative embodiment of the present invention is shown. The plug 111' comprises a proximal plug barrel portion 103', a wire boss 6401, and a distal plug cone portion 104'. The plug 111' also comprises a wire channel 105'.

Figure 71:
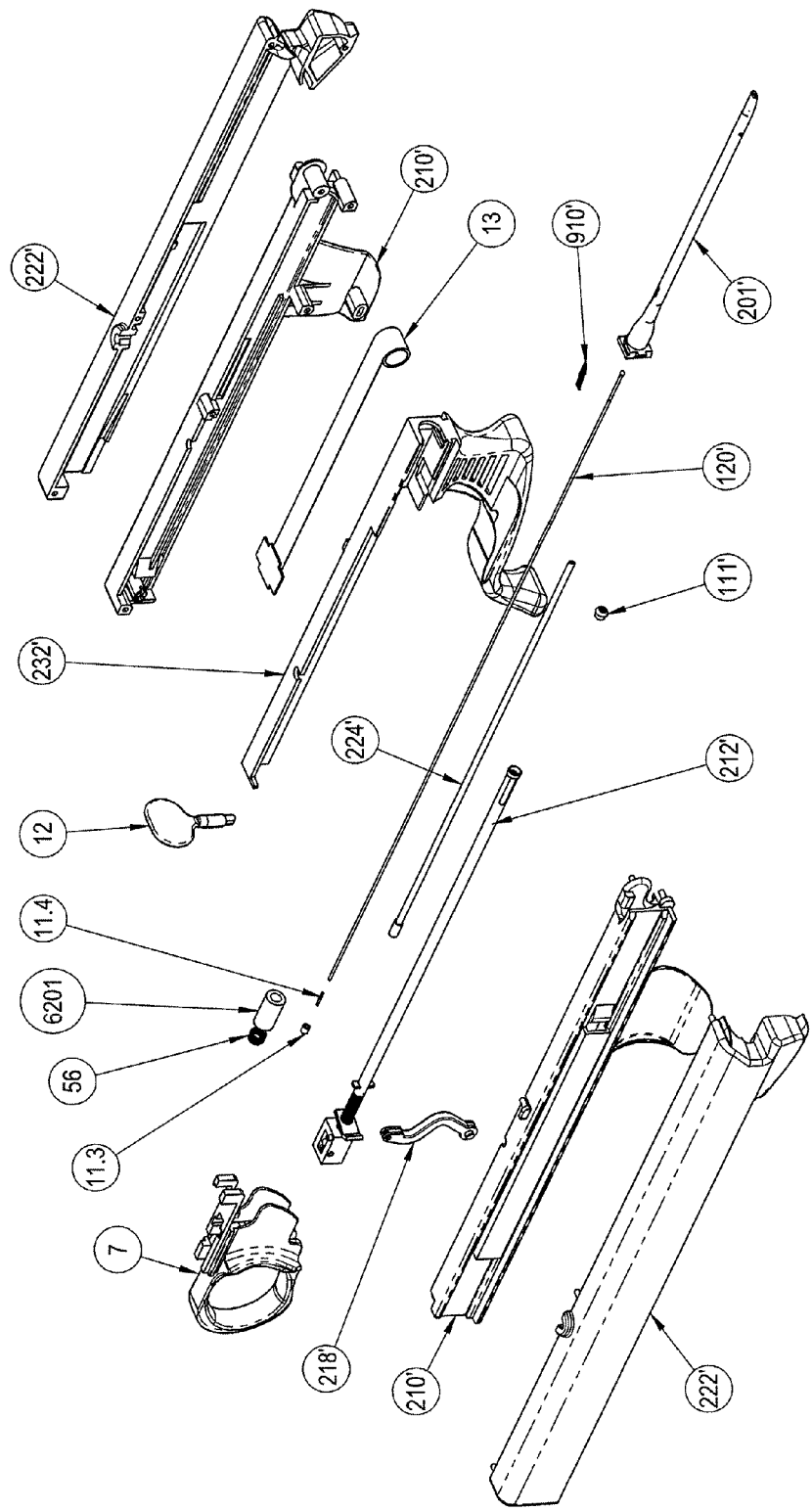
FIG. 71 shows an exploded view of the deployment device, according to an alternative embodiment of the present invention.

Additional parts of the deployment device (and implant) of an alternative embodiment of the present invention will now be discussed with reference to the functionality of the discussed parts. FIG. 71 shows an exploded view of the deployment device of an alternative embodiment of the present invention. The deployment device includes one or more of the following: left portion and right portion of the skin flange 222', left portion and right portion of the housing 210', thumb crutch 7, cutter lever assembly 218', push tube assembly 212', plug 111', wire 120', sheath 201', cutter tube 224', footplate 910', ferrule 11.3, wire insert 11.4, locking lever spring 56, elastomeric spring 6201, locking pin 12, finger pull 232', and skin flange spring 13.

Figure 51:
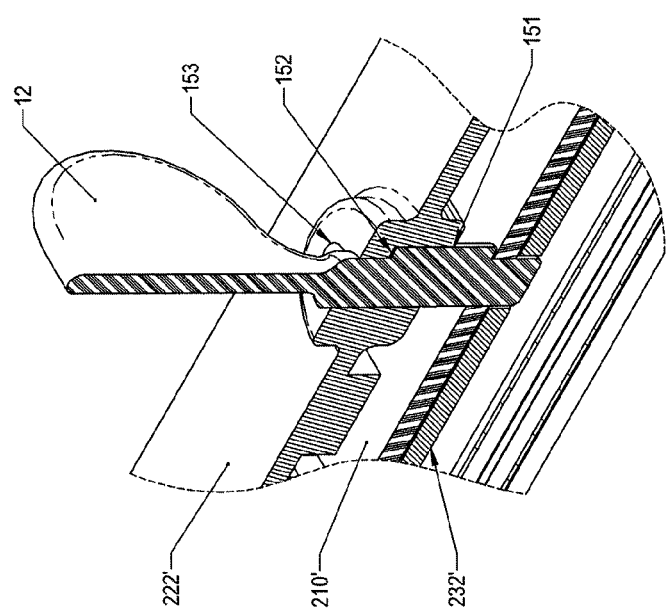
FIG. 51 shows a longitudinal section view through the locking pin, housing, finger pull, and skin flange, according to an alternative embodiment of the present invention.

In general, the deployment device is operated by a one-hand, non-handed, single squeezing motion to accomplish three chief functions: (i) sheath retraction and footplate exposure within the artery as described supra, (ii) plug deployment, and (iii) wire bend-over and cut-off. This single squeezing motion operates in sequence two levers: the finger pull 232' and the thumb crutch 7, the distance between the two in the default configuration can be designed to accommodate the 95 percentile adult female grip axis. Turning to FIG. 51, a longitudinal section view through the locking pin 12 is shown. One longitudinal half of the skin flange 222', and one longitudinal half of the housing 210', are also shown (both of which are made up of two longitudinal halves). The locking pin 12 is held in place by the pin retention feature 151, which abuts the locking pin retention undercut feature 152, and by the tension of the skin flange spring (13) (see also FIG. 48) pulling on the skin flange 222'.

Figure 52:
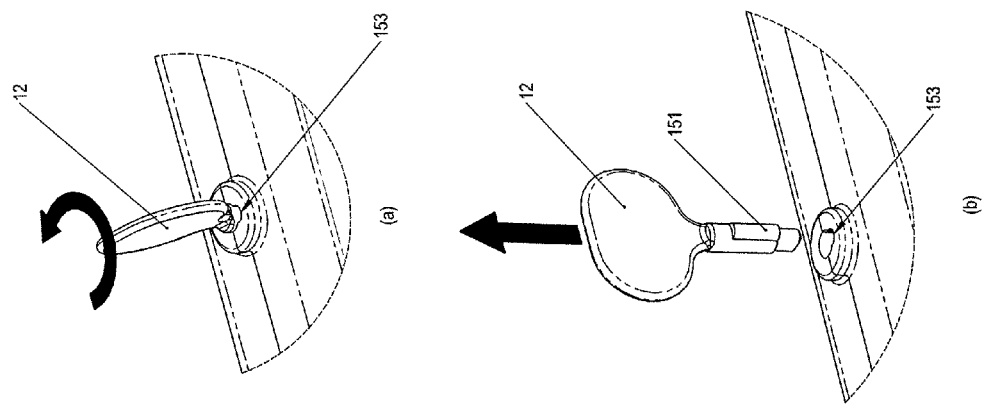
FIGS. 52 a-b show removal of the locking pin from the deployment device, according to an alternative embodiment of the present invention.

As shown in FIG. 52*a-b*, rotation of the locking pin 12 about 90 degrees by the user, causes the pin retention feature 151 to be oriented concentric with the locking pin retention feature relief 153 feature, enabling the locking pin 12 to be removed from the deployment device by pulling the locking pin 12 straight up (away) from the deployment device. Once the locking pin 12 is removed from the deployment device, the finger pull 232' is free to move in a proximal direction. Proximal movement of the finger pull 232' triggers three events: (1) skin flange 222' release; (2) thumb crutch 7 unlock, and (3) footplate exposure 910'.

Figure 53:
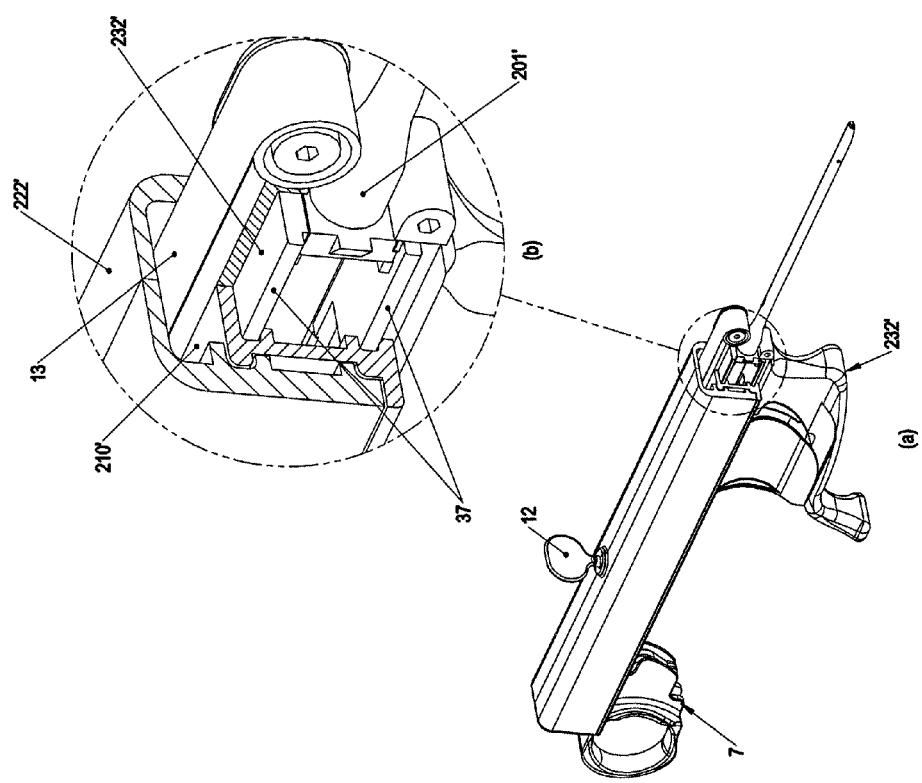
FIGS. 53 a-b show a right side perspective view of the deployment device and a magnified window portion view of the deployment device, according to an alternative embodiment of the present invention.
Figure 72:
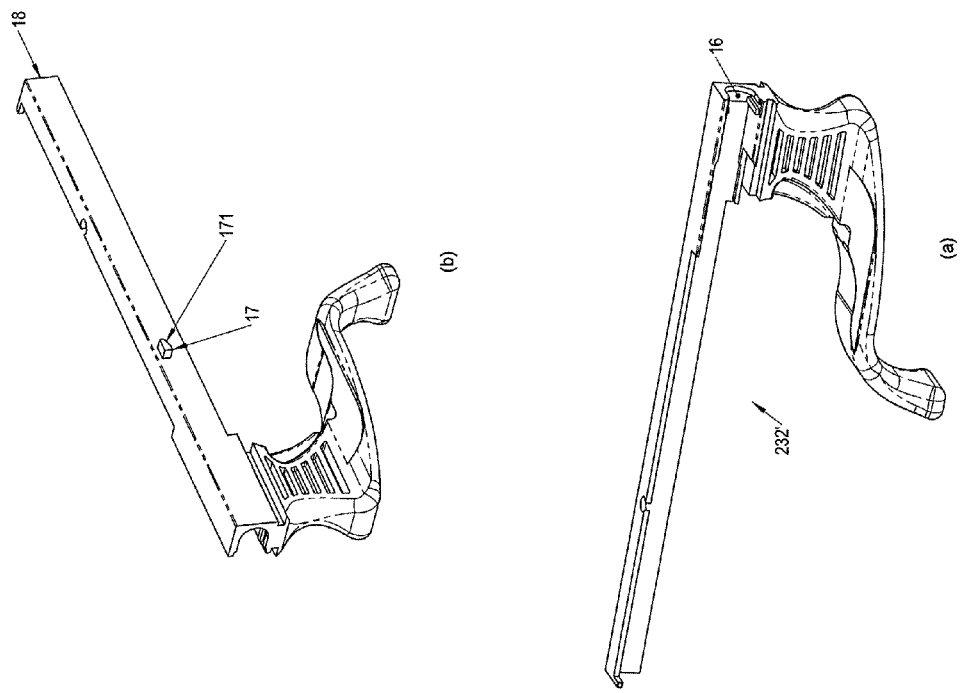
FIG. 72 shows a left side and right side view of the finger pull, according to an alternative embodiment of the present invention.

Turning to FIG. 53*a*, a right side perspective view of the deployment device 200' is shown, according to an alternative embodiment of the present invention. FIG. 53*b* shows a magnified window view of a portion of the deployment device of FIG. 53*a*, according to an embodiment of the present invention. As shown, a portion of the finger pull 232' is positioned inside the housing 210', and is guided by the finger pull guide rails 37. Once the locking pin 12 is removed as discussed above, the finger pull 232' is free to travel proximally by the user. Thus, at this point, a user may pull the finger pull 232' proximally until it is locked in place. This locking of the finger pull 232' is accomplished when the trigger feature 17 snaps into position in the skin flange/finger pull locking finger proximal surface 27 (see also FIGS. 54 and 55). FIG. 72 shows the left half and the right half of the finger pull 232'. The sheath assembly socket 16, trigger feature 17, proximal surface finger pull 18, and sloped proximal surface trigger feature 171 are also shown.

Figure 54:
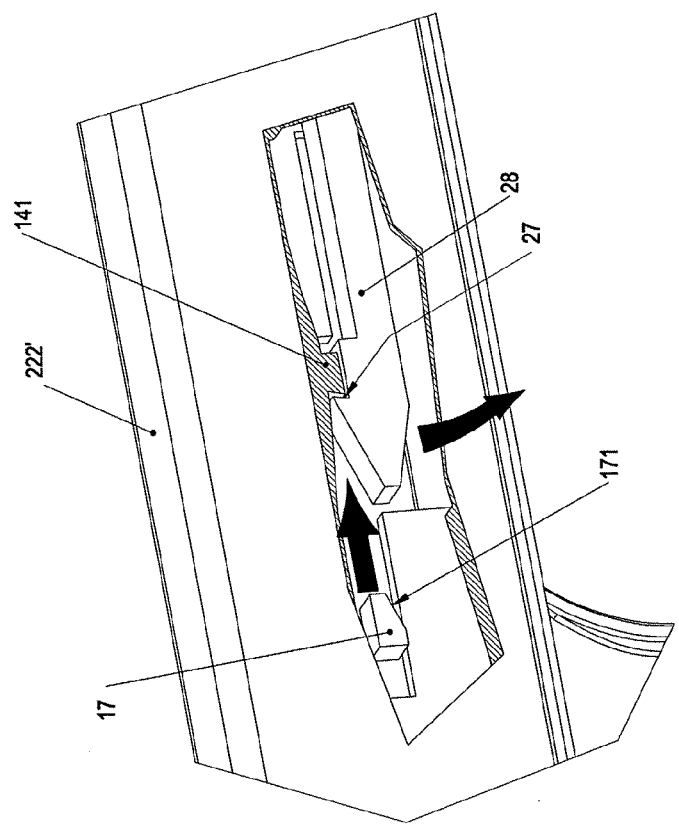
FIGS. 54 and 55 show magnified views of a portion of the inside of the skin flange and housing, according to an alternative embodiment of the present invention.
Figure 55:
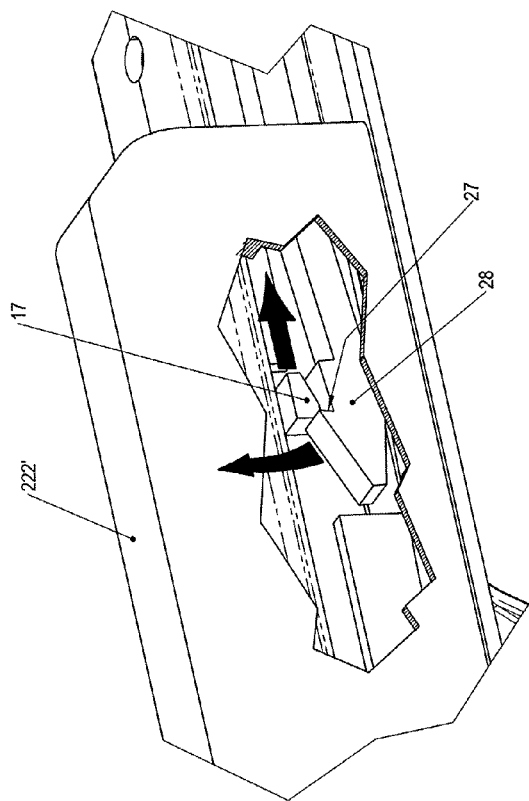
Figure 68:
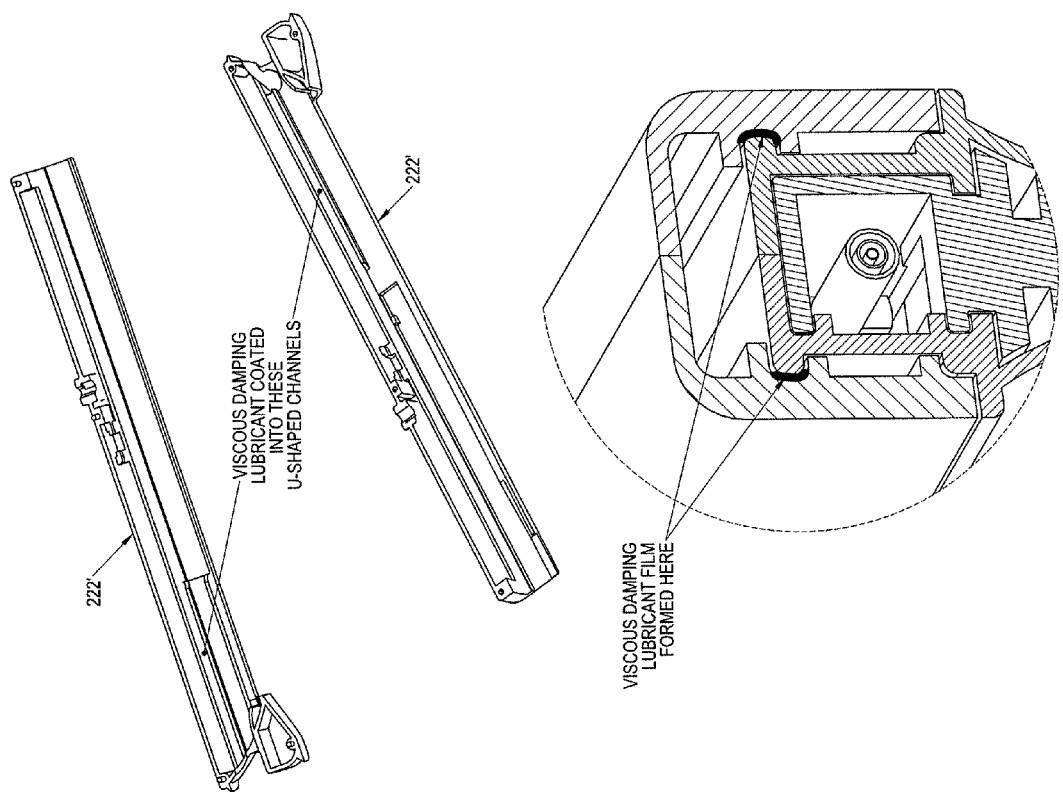
FIG. 68 shows portions of the skin flange and the housing damped via viscous shearing with a film of high viscosity biocompatible lubricant, according to an alternative embodiment of the present invention.
Figure 73:
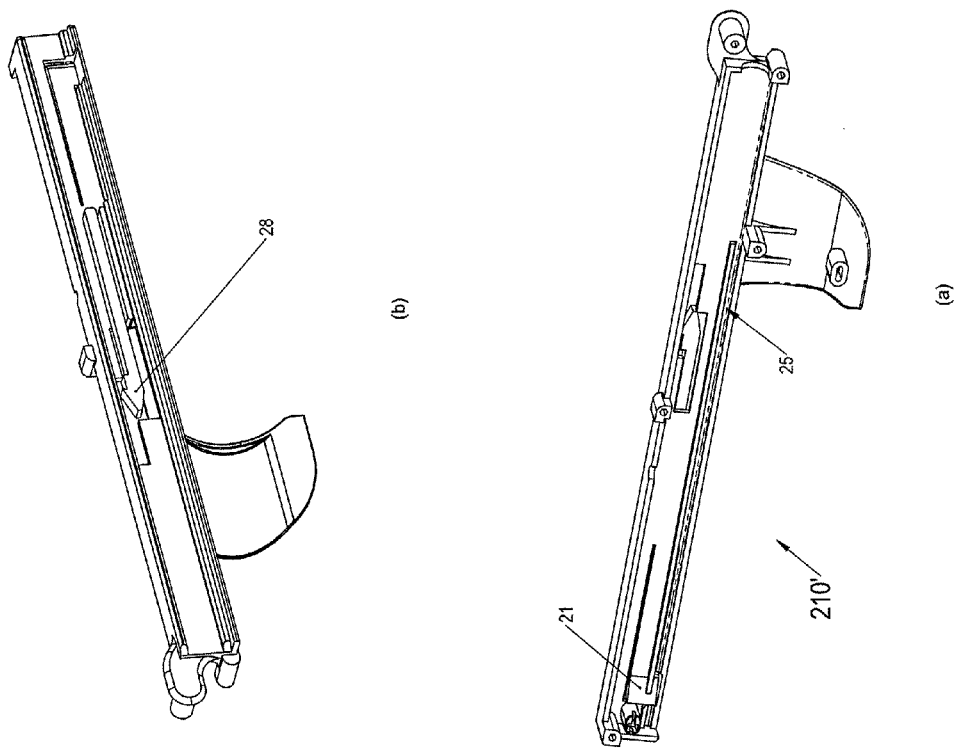
FIG. 73 shows a left side and right side view of the left half of the housing, according to an alternative embodiment of the present invention.

FIGS. 54 and 55 show magnified views of a portion of the inside of the skin flange and housing, according to an alternative embodiment of the present invention. The release of the skin flange 222' from a locked position will now be discussed. The skin flange 222' can be unlocked as a consequence of the sloped proximal surface 171 of the trigger feature 17 displacing the skin flange/finger pull locking finger 28, thereby eliminating the interference between the skin flange/finger pull locking finger 28 and the skin flange locking feature 141. After the interference is eliminated, the skin flange spring 13 is free to pull the skin flange 222' distally until stopped by the skin surface of the patient and the counter-directed force developed in the wire by the footplate contacting the inside surface of the artery. The skin flange spring 13 (see also FIG. 48) can be a constant force variety thus applying a consistent force through the skin flange 222' to patient's body causing the delivery device and thereby the footplate to retract in a proximal direction until the footplate is positioned along the inside surface of the artery with a pre-determined force (e.g. 2 lbf). Turning now to FIG. 68, the skin flange linear travel, by virtue of the skin flange spring 13, along its and the housing's guide rail features, can be damped via viscous shearing with a film of high viscosity biocompatible lubricant coated onto mating sliding surfaces on both the skin flange 222' and the housing 210'. FIG. 73 shows a left side and right side view of the left half of the housing 210'. The sloped surface, thumb crutch locking finger 21, thumb crutch guide rails 25, skin flange finger pull locking finger 28 are also shown.

Figure 70:
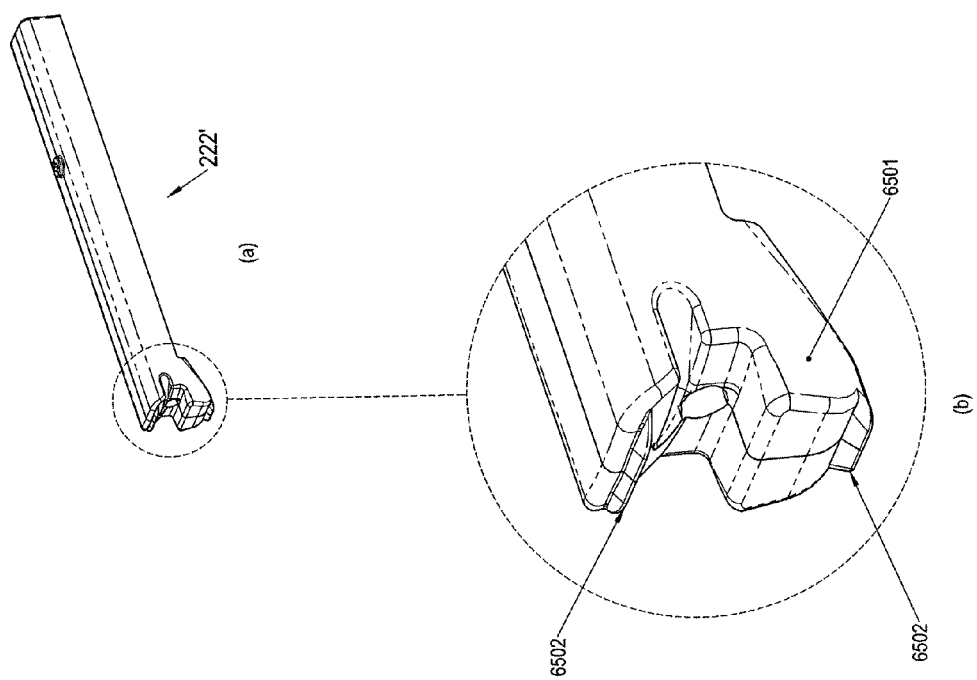
FIG. 70 shows a left side perspective view and magnified window view of the skin flange assembly, according to an alternative embodiment of the present invention.

FIG. 61 shows the skin flange 222' in a nearly fully deployed position. The chin feature 6501 on the distal end of the skin flange 222' displaces and reorients the plane of the patient's skin 950 such that it is substantially perpendicular to the sheath 201'. This reorientation of the plane of the patient's skin 950 is aided by the upper and lower saw-tooth-like gripping features 6502 (see also FIG. 70). These saw-tooth-like gripping features 6502 create engagement (i.e. friction) with the patients skin 950 and prevent tangential slippage of the skin flange 222' with the patient's skin 950 allowing reliable reorientation of the patient's skin 950 and prevention of side loads being applied to the sheath 201'.

Figure 56:
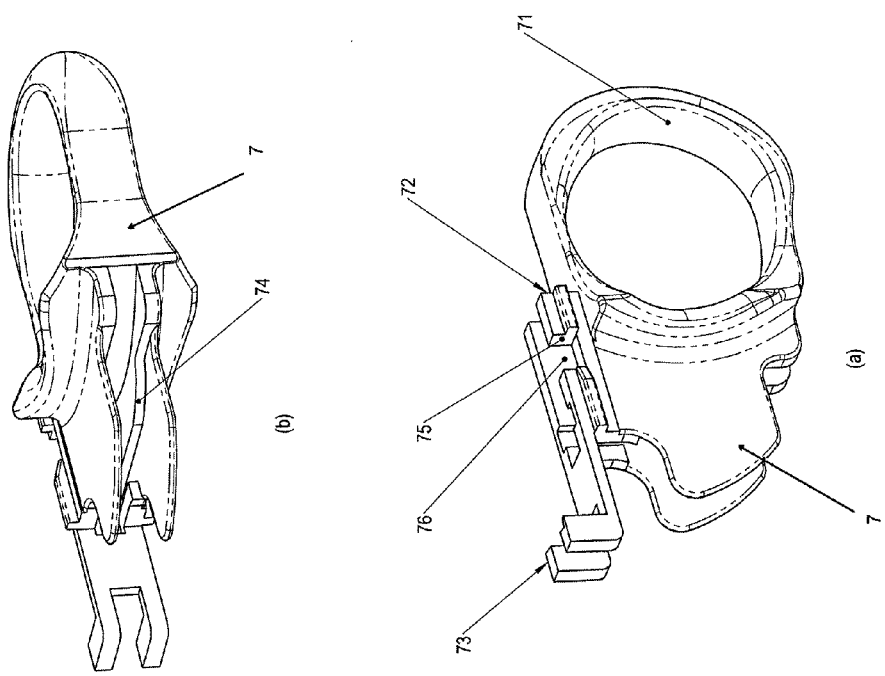
FIGS. 56a-b show various views of the thumb crutch, according to an alternative embodiment of the present invention.

FIGS. 56a-b show various views of the thumb crutch 7, according to an embodiment of the present invention. The thumb crutch 7 includes one or more of the following: a thumb ring 71, guide rails 72, spring yoke 73, cutter lever pin surface 74, locking slot proximal surface 75, and a locking slot 76.

Figure 57:
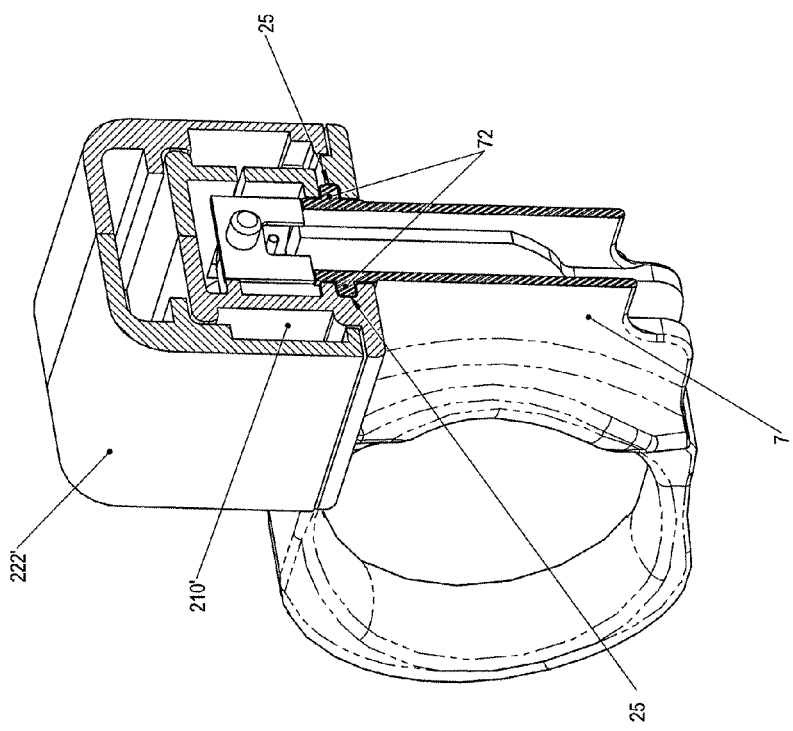
FIGS. 57 and 58 a-b show the thumb crutch and its interrelation to other components on the proximal end of the deployment device, according to an alternative embodiment of the present invention.
Figure 58:
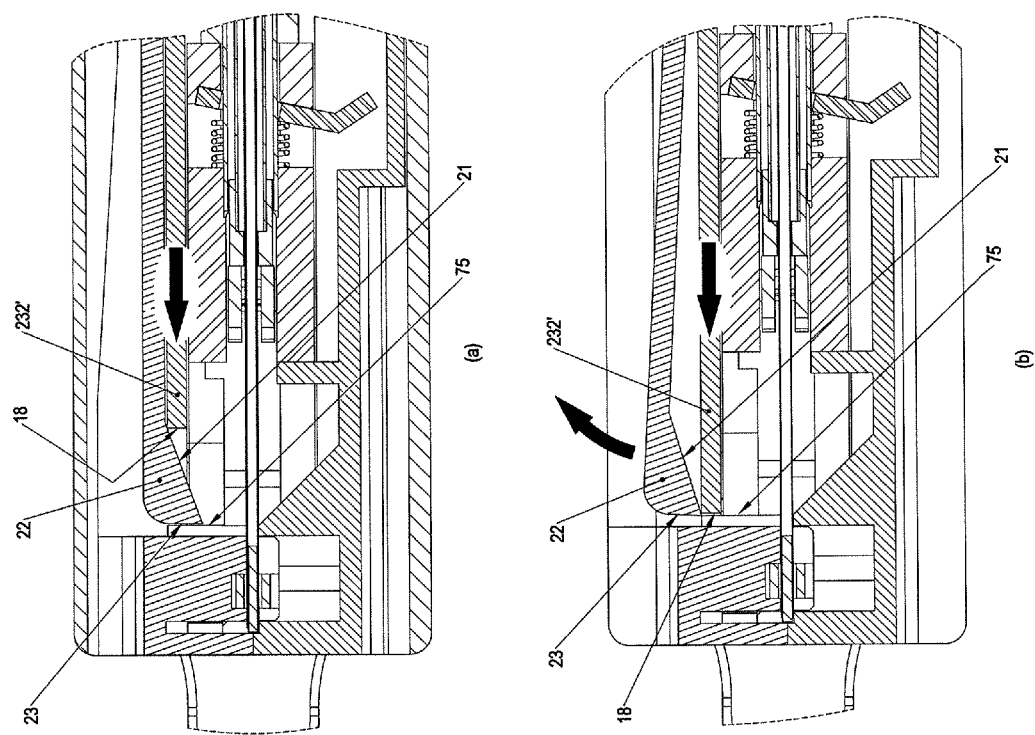

Turning to FIGS. 57 and 58 a-b, these figures show the thumb crutch 7 and its interrelation to other components on the proximal end of the deployment device 200', according to an alternative embodiment of the present invention. A portion of the thumb crutch 7 is assembled inside the housing 210', with the thumb crutch guide rails 72 positioned inside the thumb crutch guide slots 25. The thumb crutch 7 is locked in a starting position via the interference between the proximal surface of the thumb crutch locking slot 75 and the thumb crutch locking finger distal surface 23. As the finger pull 232' is retracted proximally, the proximal surface of the finger pull 18 comes into contact with the sloped surface of the thumb crutch locking finger 21, displacing the thumb crutch locking finger 22 laterally. This lateral displacement of the thumb crutch locking finger 22 eliminates the interference between the proximal surface of the thumb crutch locking slot 75 and thumb crutch locking finger distal surface 23, thereby unlocking the thumb crutch 7 for distal displacement by the user.

Figure 59:
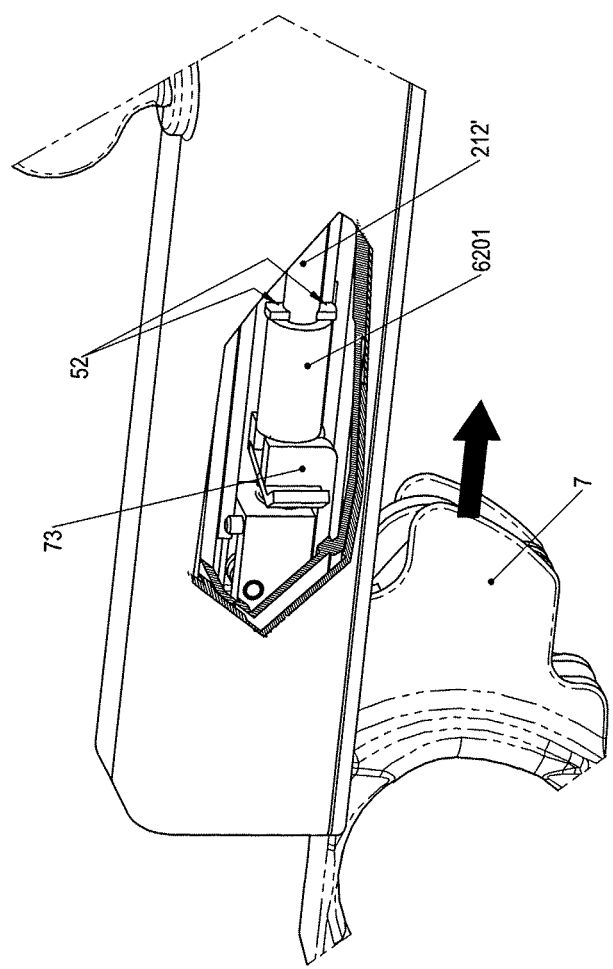
FIG. 59 shows the distal movement functionality of the thumb crutch with respect to portions of the deployment device, according to an alternative embodiment of the present invention.

Turning to FIG. 59, the distal movement functionality of the thumb crutch 7 is shown with respect to portions of the deployment device, according to an alternative embodiment of the present invention. The thumb crutch 7 is moved distally, driving the plug 111' and push tube assembly 5 distally via the compression force of the spring tube 6201 acting on the push tabs 52. In a preferred embodiment, the spring tube 6201 is an elastomeric spring, which acts as a force conduit. The spring tube 6201 preferably prevents the user from ever applying more than a certain amount of force (e.g., 4 lbs.). Due to this compliant nature of the spring tube 6201 as it extrudes over the push tabs 52, a constant force is applied to the push tabs 52 regardless of the amount of resistance acting against the push tube assembly 5 from friction, tissue tract, and/or any variations in arterial wall thickness.

Figure 9D:
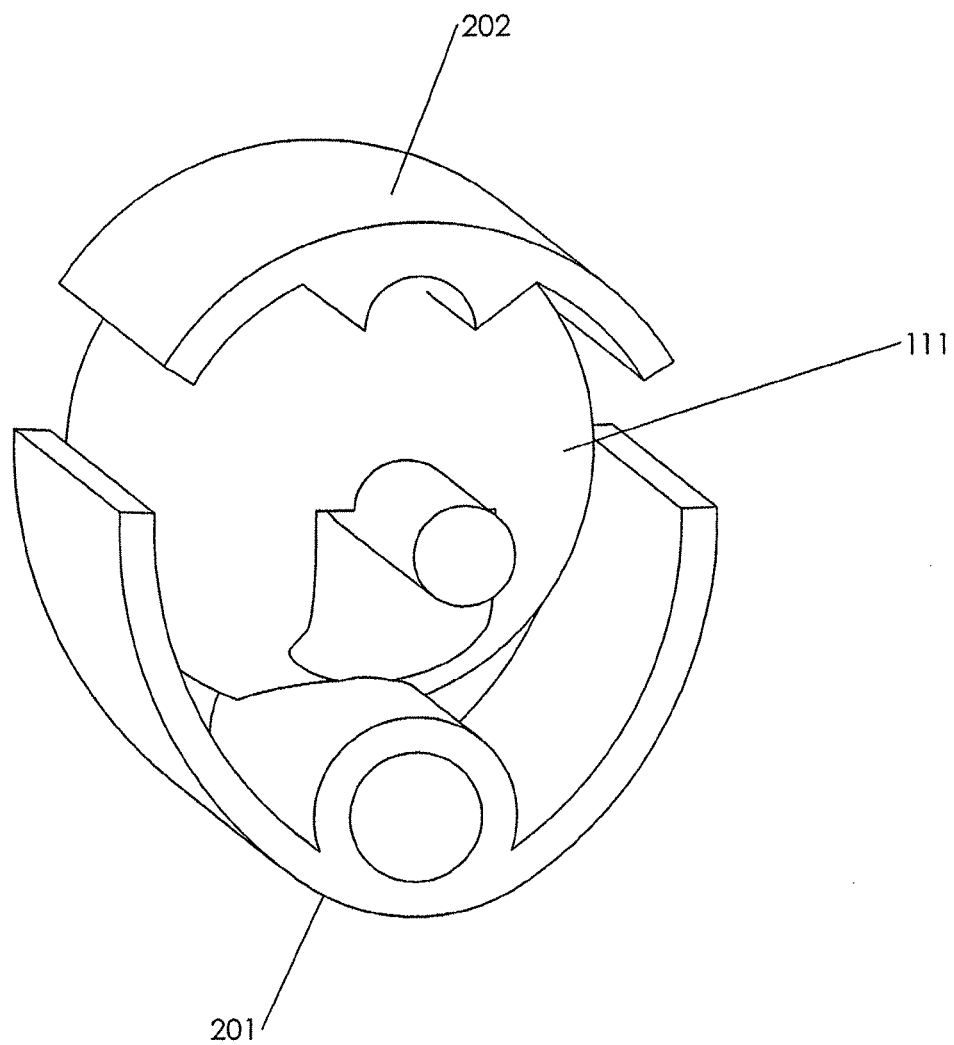
FIG. 9d is a perspective view showing the local expansion of a portion of the distal C-Tubes while allowing passage of the plug therethrough, according to an embodiment of the present invention.
Figure 62:
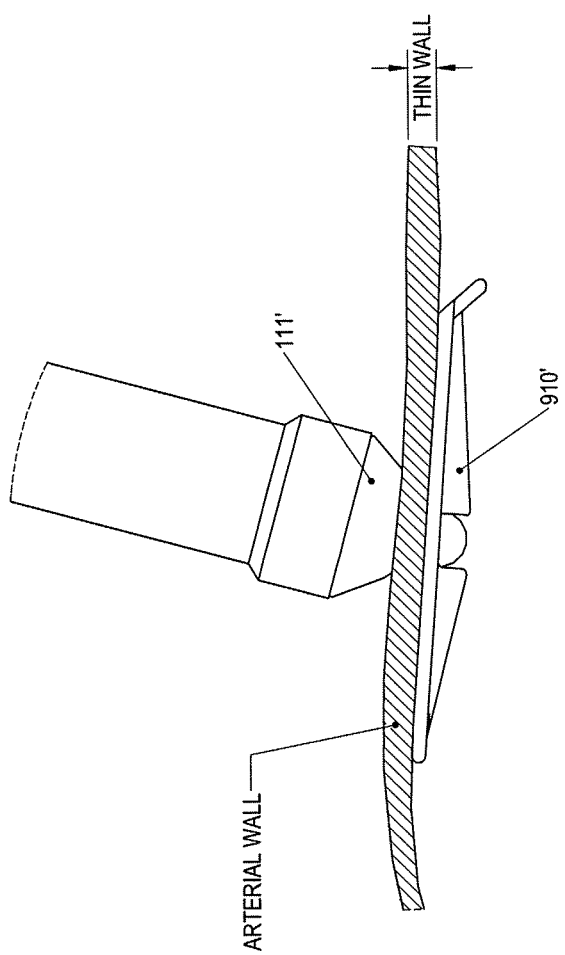
FIG. 62 shows the plug and footplate in a deployed position with respect to a relatively thin arterial wall (as compared with FIG. 63), according to an alternative embodiment of the present invention.
Figure 63:
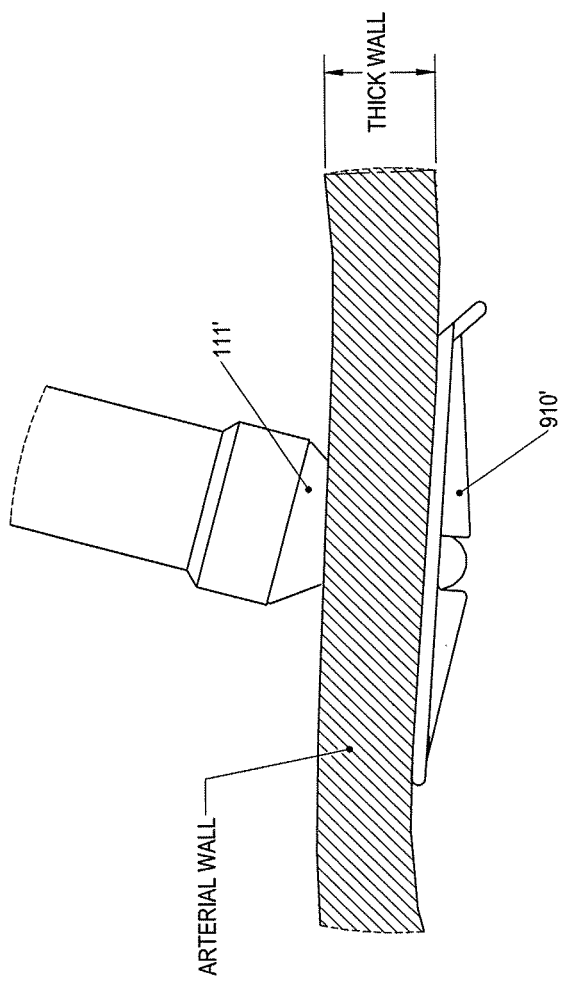
FIG. 63 shows the plug and footplate in a deployed position with respect to a relatively thick arterial wall (as compared with FIG. 62), according to an alternative embodiment of the present invention.

Thus, the system comprised of the spring tube 6201 and the push tube tabs 52 acts as an automatic clutch which (i) seats the plug to the footplate with a pre-determined force (e.g. 4 lbf) over a range of arterial wall thicknesses (e.g., 1 mm) to achieve an adequate blood seal, and (ii) precludes stressing the footplate socket-to-wire ball joint and the tube-to-wire joint beyond a pre-determined force (e.g. 4 lbf) to prevent joint failure. As the plug 111' is driven distally through the sheath 201', the sheath 201' is uncurled by the conical portion of the plug 104' (similarly to what is shown in FIG. 9d). The plug 111' travels along the wire extension 120' and passes through the distal tip 203' of the sheath 201'. The plug 111' continues to travel distally until it comes either into contact with the top surface of the footplate 910', meets sufficient resistance from a thin arterial wall (see FIG. 62), or it meets sufficient resistance from thickened hardened arterial wall (see FIG. 63). In either case, the plug 111' has met sufficient resistance to prevent further distal travel. However, the thumb crutch 7 is able to continue to move distally. This causes the tube spring 6201 to deform over the push tabs 52, which allows the thumb crutch continued distal movement.

Figure 64:
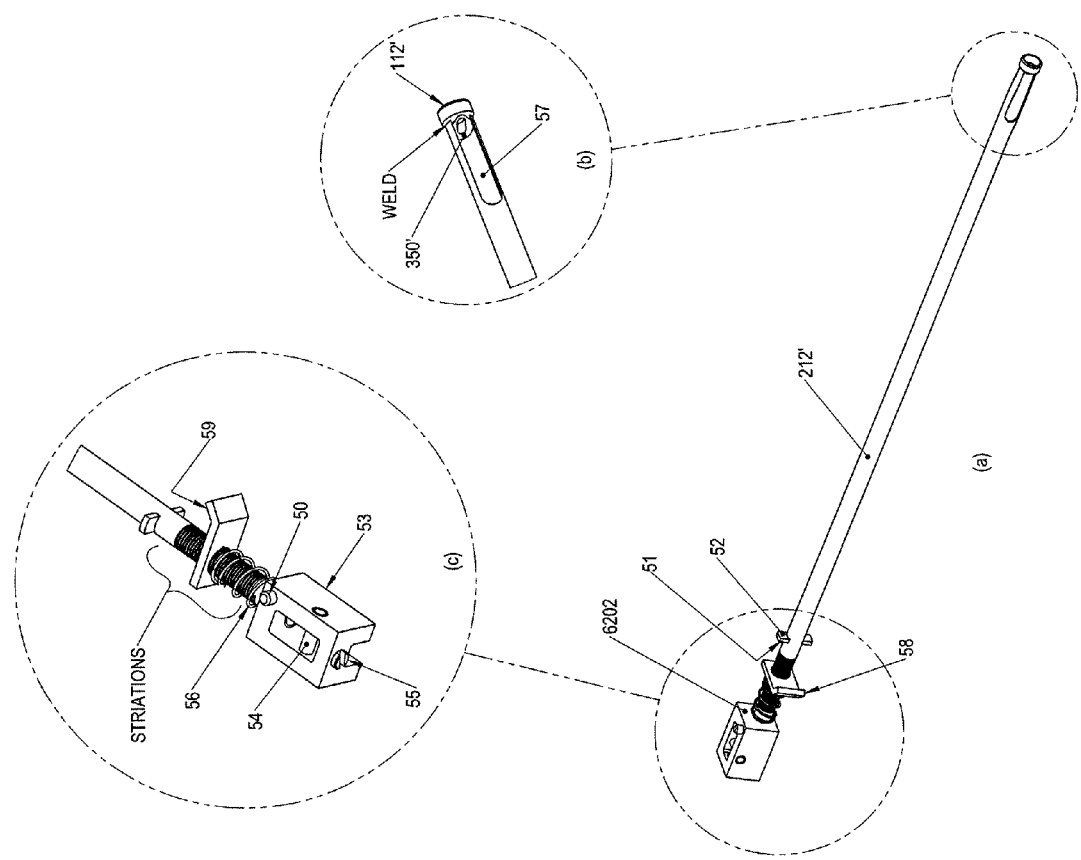
FIGS. 64 a-c show a push tube assembly, and various magnified sections of the assembly, according to an alternative embodiment of the present invention.

FIGS. 64 a-c show a push tube assembly, and various magnified sections of the assembly, according to an alternative embodiment of the present invention. Push tube assembly includes one or more of the following: a push tube 212', push tabs 52, push tab proximal surface 51, push tube locking lever 58, push tube lock lever lateral surface 59, pivot block 53, anti-rotation screw 55, lever axle 54, locking lever spring 56, stop pin 50, push tube insert 112', push tube insert sloped surface 350', and cutter tube exit 57. The preferred method of fastening the push tube insert 112' to the push tube is laser welding.

Figure 60:
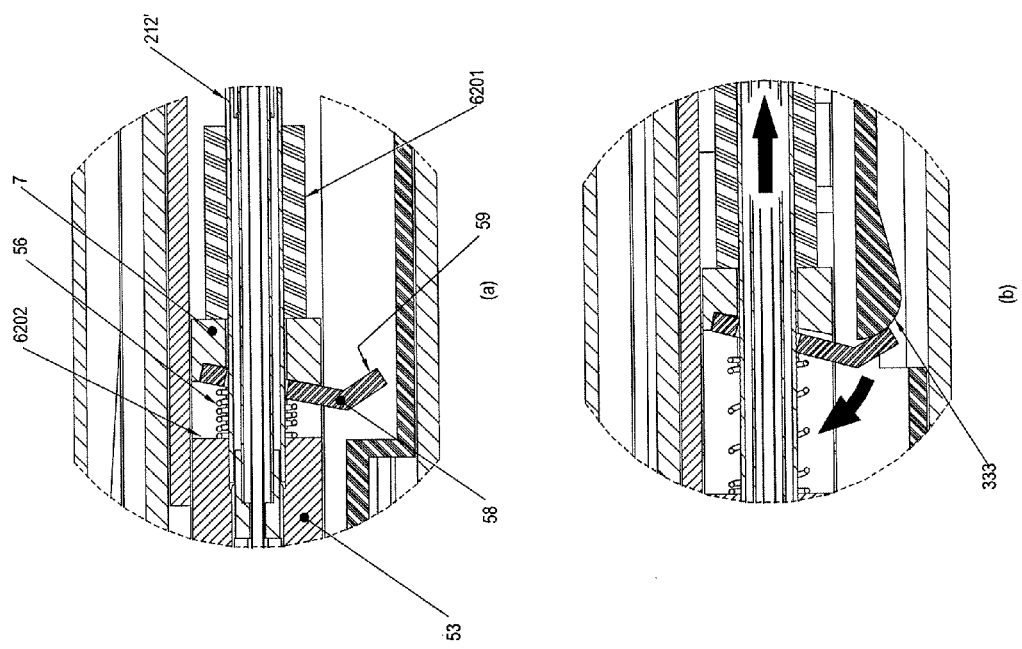
FIG. 60 shows detail of the push tube locking lever in a pre and post lock positions, according to an alternative embodiment of the present invention.
Figure 74:
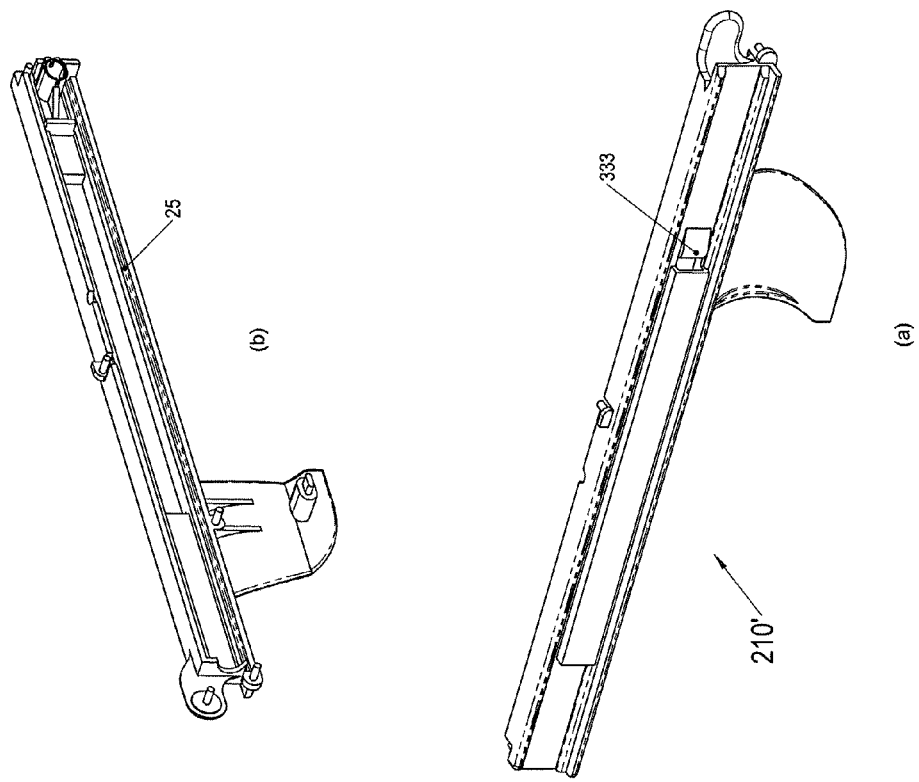
FIG. 74 shows a left side and right side view of the right half of the housing, according to an alternative embodiment of the present invention.

Push tube locking lever 58 is designed to lock the push tube 212' in position—as the thumb crutch 7 is driven distally, the push tube locking lever lateral surface 59 comes into contact with the locking lever boss 333. As shown in FIG. 60, the push tube locking lever 58 is maintained in the proper position relative to the thumb crutch 7 via a wound compression spring 56 wound over the push tube 212' acting between a vertical wall feature 6202 located on the pivot block 53 and the push tube locking lever 58. Continued distal movement of the push tube 212', combined with the interface between the locking lever boss 333 and the push tube locking lever lateral surface 59, results in the push tube locking lever 58 cocking proximally and effectively locking the push tube assembly into position relative to the housing (see FIG. 60). FIG. 74 shows a left side and right side view of the right half of the housing 210'. The thumb crutch guide rails 25 and locking lever boss 333 are also shown.

Figure 65:
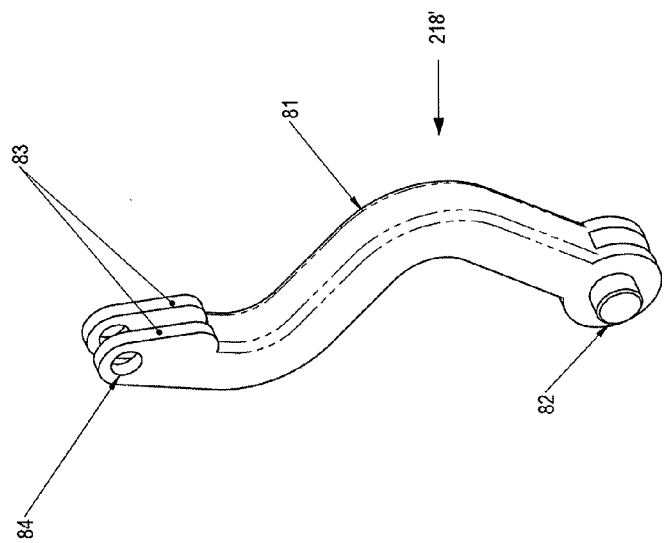
FIG. 65 shows a cutter lever assembly, according to an alternative embodiment of the present invention.

FIG. 65 shows a cutter lever assembly 218', according to an alternative embodiment of the present invention. Cutter lever assembly 218' includes one or more of the following: a cutter lever 81, a cutter lever pin 82, a cutter tube drive surface 83, and a pivot hole 84.

Figure 66:
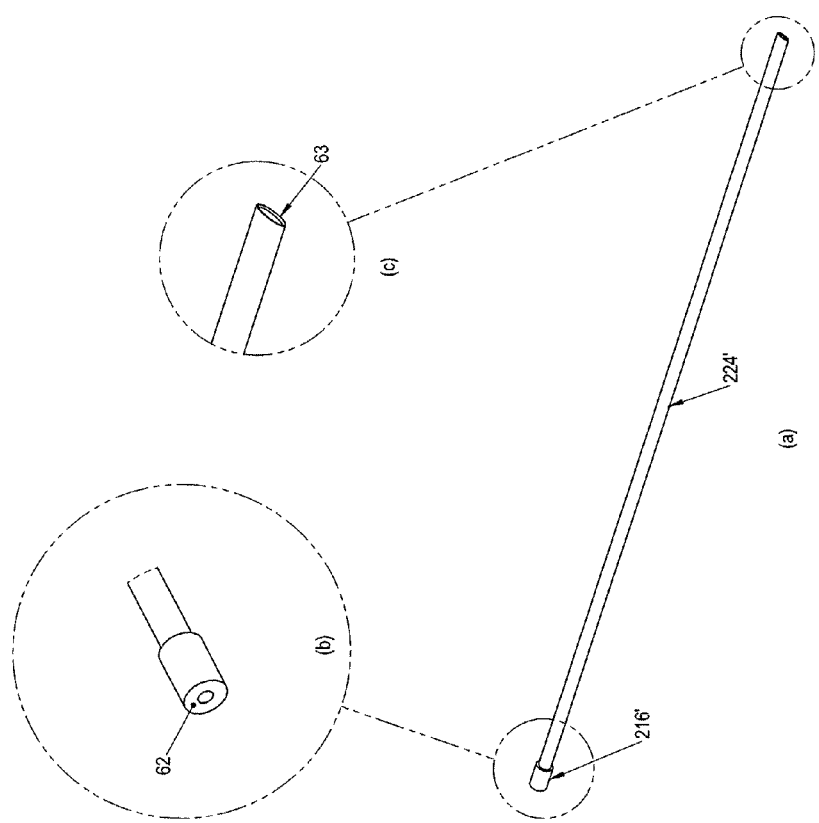
FIGS. 66a-c show a cutter tube assembly, and various magnified portion views of the assembly, according to an alternative embodiment of the present invention.

FIGS. 66a-c show a cutter tube assembly, and various magnified portion views of the assembly, according to an alternative embodiment of the present invention. Cutter tube assembly includes one or more of the following: a cutter tube 224', a cutter tube cap 216', a cutter tube cap proximal surface 62, and a cutter tube assembly distal surface 63.

Figure 69:
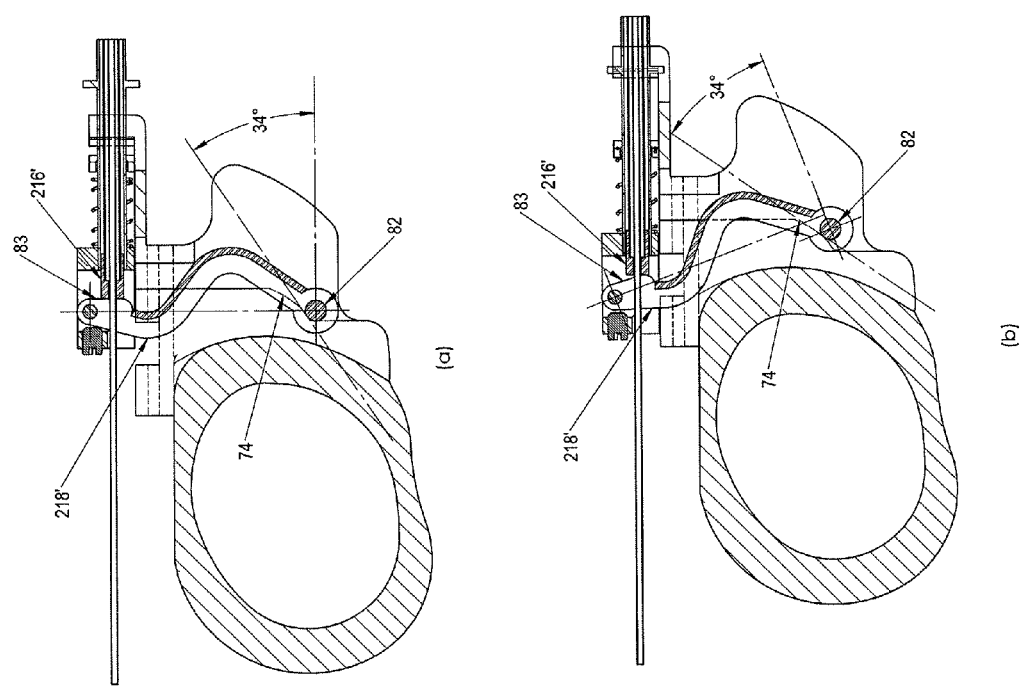
FIGS. 69 a-b shows the maintenance of a constant pressure angle throughout the rotation of the cutter lever assembly, according to an alternative embodiment of the present invention.

The thumb crutch 7 is designed to displace the cutter tube 224' forward distally. Continued distal movement of the thumb crutch 7, combined with the push tube 212' being locked into position, results in the cutter lever assembly 218' being rotated forward via the engagement of the cutter lever pin 82 and the cutter lever pin surface 74. As depicted in FIG. 69, due to the profile of the cutter lever pin cam profile surface 74, a constant pressure angle (e.g., approximately 34°) is maintained throughout the rotation of the cutter lever assembly 218', resulting in cutter lever displacement greater than the thumb crutch displacement, thus achieving the 90$^{th}$ percentile female grip axis as measured between the thumb crutch and the finger pull.

Figure 67:
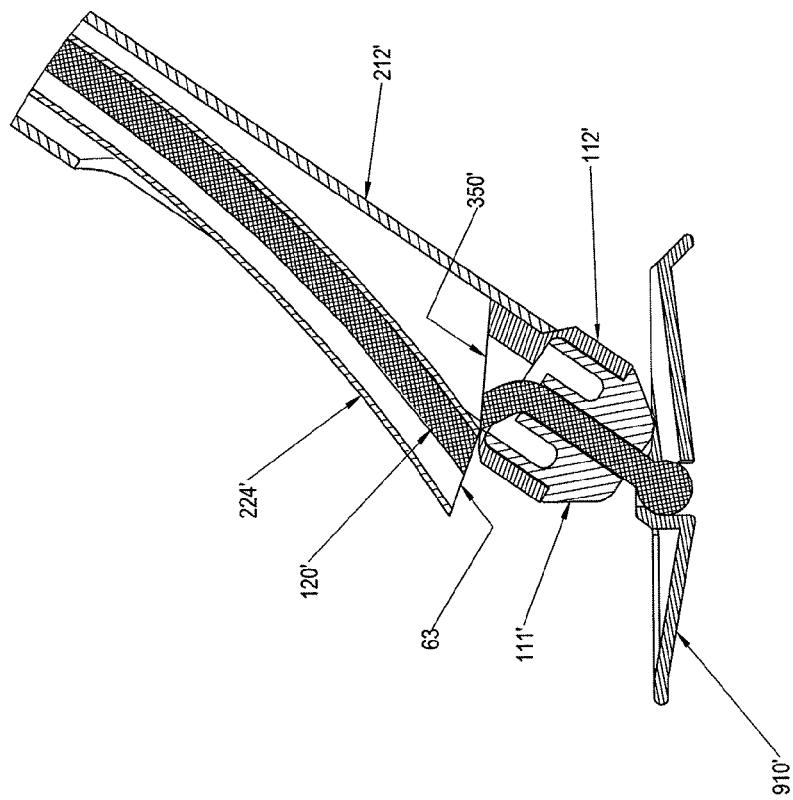
FIG. 67 shows the cutter tube assembly bending over the wire and shearing it apart, according to an alternative embodiment of the present invention.

The cutter lever assembly 218' drives the cutter tube 224' forward. Due to the interface of the cutter tube drive surface 83 and the cutter tube cap proximal surface 62, rotation of the cutter lever assembly 218' results in the cutter tube 224' being driven distally. At this point, the cutter tube assembly bends over wire 120' and then shears it apart (see FIG. 67). As the cutter tube assembly is driven distally, the cutter tube assembly distal surface 63 bends and then shears the wire 120' due to the interface between the push tube insert sloped surface 350' and the cutter tube assembly distal surface 63. The sloped surface angle is selected (e.g. 30 degrees) to minimize possible wire 120' lengthening during wire bend-over and wire cut-of, that is, between the time the wire is contacted by the cutter tube distal surface 63 and the wire is cut by the insert sloped surface 350'.

At this stage, the closure device implant has been inserted, seated and sheared from the deployment device 200'. The deployment device 200' is then automatically retracted from the patient by the action of the skin flange 222' now allowed to continue its linear travel via the action of the skin flange spring 13 until it reaches the end of its travel and the device is then discarded.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A closure device deployment device comprising:
   an elongated housing extending along a longitudinal axis;
   a sliding member comprising a first portion connected to the inside of the housing, and slidable within the housing between a first position and a second position in the proximal direction along the longitudinal axis upon the application of a first force in the proximal direction, and a second portion extending outside of the housing and along a plane that is perpendicular to the longitudinal axis;
   a sheath assembly extending along the longitudinal axis comprising a proximal end which is connected to a distal end of said first portion of said sliding member, wherein said sheath is moveable in the proximal direction along the longitudinal axis upon the application of the first force on said sliding member;
   a rigid wire extending along the longitudinal axis and connected at a proximal end to said housing;
   a footplate connected to the a distal end of said wire and extending along a plane that is parallel to the longitudinal axis, and structured to be within the distal end of said sheath assembly when the sliding member is in the first position, and outside of the sheath assembly when the sliding member is in the second position;
   a skin flange extending along the longitudinal axis, connected to the outside of the housing, and slidable in the distal direction along the housing between a first position and a second position; and
   a skin flange locking feature structured to lock said skin flange in the first position, wherein said sliding member is structured to release said skin flange from said skin flange locking feature per proximal movement of said sliding member allowing said skin flange to slide in the distal direction, wherein a distal end of the skin flange is structured to contact the surface of the skin in the second position, and while the skin flange is in the second position against a patient's skin surface and said footplate is within a patient's blood vessel during use of the closure device deployment device, a predetermined constant proximal force seats the footplate against an inside wall of the blood vessel.

2. The closure device deployment device of claim 1, wherein said sliding member further comprises guide rails within the housing to facilitate movement of said sliding member in the proximal direction.

3. The closure device deployment device of claim 2, wherein said elongated housing further comprises a housing locking feature which locks said sliding member in place with respect to said housing when said sliding member is in the second position.

4. The closure device deployment device of claim 3, further comprising a skin flange spring attached to said skin flange and structured to exert a force on the skin flange in the distal direction.

5. The closure device deployment device of claim 4, wherein said skin flange spring is structured to actuate the skin flange to slide in the distal direction to the second position upon the exertion the force on the skin flange in the distal direction after the skin flange is released from the skin flange locking feature.

6. The closure device deployment device of claim 5, wherein said skin flange spring is a constant force spring.

7. The closure device deployment device of claim 6, wherein the distal end of the skin flange further comprises a chin feature structured to displace and reorient a plane of a portion of the patient's skin during use of the closure device deployment device.

8. The closure device deployment device of claim 7, wherein said chin feature is structured to displace and reorient the plane of a portion of the patient's skin such that the plane of a portion of the patient's skin is substantially perpendicular to said sheath assembly.

9. The closure device deployment device of claim 7, wherein said chin feature comprises an upper gripping feature and a lower gripping feature.

10. The closure device deployment device of claim 1, wherein said skin flange is coated with a biocompatible lubricant comprising a viscosity which allows the skin flange's sliding action to be damped as it moves along the distal direction.

11. A closure device deployment device comprising:
    an elongated housing extending along a longitudinal axis;
    a first sliding member comprising a first portion connected to the inside of the housing, and slidable within the housing between a first position and a second position in the distal direction along the longitudinal axis upon the application of a first force in the distal direction, and a second portion extending outside of the housing and along a plane that is perpendicular to the longitudinal axis;
    a rigid wire extending along the longitudinal axis and connected at a proximal end to said housing;
    a push tube extending along the longitudinal axis over the wire and positioned distally to the first portion of the first sliding member that is within the housing, wherein said push tube is movable over the wire in the distal direction from a first position to a second position along the longitudinal axis upon the application of the first force on said first sliding member;
    a plug comprising a proximal end and a distal end and positioned distally to said push tube over said wire, wherein said plug is movable over the wire in the distal direction from a first position to a second position along the longitudinal axis upon the application of the first force through said push tube by said first sliding member; and
    a force conduit mechanism positioned over said wire between the first sliding member and said push tube within the housing, and structured to maintain the distal first force ultimately applied to the plug at or below a predetermined force; a second sliding member comprising a first portion connected to the inside of the housing, and slidable within the housing between a first position and a second position in the proximal direction along the longitudinal axis upon the application of a second force in the proximal direction, and a second portion extending outside of the housing and along a plane that is perpendicular to the longitudinal axis; a sheath assembly extending along the longitudinal axis comprising a proximal end which is connected to a distal end of said first portion of said sliding member, wherein said sheath is moveable in the proximal direction along the longitudinal axis upon the application of the second force on said second sliding member; a footplate connected to a distal end of said wire and extending along a plane that is parallel to the longitudinal axis, and structured to be within the distal end of said sheath assembly when the second sliding member is in the first position, and outside of the sheath assembly when the second sliding member is in the second position; a skin flange extending along the longitudinal axis: connected to the outside of the housing: and slidable in the distal direction along the housing between a first position and a second position; and a skin flange locking feature structured to lock said skin flange in the first position, wherein said second sliding member is structured to release said skin flange from said skin flange locking feature per proximal movement of said second sliding member allowing said skin flange to slide in the distal direction; wherein a distal end of the skin flange is structured to contact the surface of the skin in the second position, and while the skin flange is in the second position against a patient's skin surface and said footplate is within a patient's blood vessel during use of the closure device deployment device, a predetermined constant proximal force seats the footplate against an inside wall of the blood vessel.

12. The closure device deployment device of claim 11, further comprising a first sliding member locking feature structured to lock said first sliding member in the first position.

13. The closure device deployment device of claim 12, wherein said second sliding member is structured to release said first sliding member from said first sliding member locking feature per proximal movement of said second sliding member allowing said first sliding member to slide in the distal direction upon the application of the first force in the distal direction.

14. The closure device deployment device of claim 12, wherein said sheath assembly is cylindrically shaped and comprises a curled annular wall having inner and outer free ends.

15. The closure device deployment device of claim 14, wherein the curled annular wall is structured to uncurl due to the passage of the plug therethrough as the plug travels in the distal direction upon application of the first force in the distal direction.

16. The closured device deployment device of claim 11, wherein said first sliding member comprises guide rails within the housing to facilitate movement of said first sliding member in the distal direction.

17. The closured device deployment device of claim 11, wherein said force conduit mechanism is an elastomeric spring.

18. The closure device deployment device of claim 11, wherein said push tube further comprises push tube tabs on the proximal end thereof comprising one or more flanges extending outside of the push tube and along a plane that is substantially perpendicular to the longitudinal axis, wherein the force conduit mechanism is structured to deform over the push tube tabs upon application of the a distal first force in order to maintain the distal first force ultimately applied to the plug at or below the predetermined force.

19. The closure device deployment device of claim 11, wherein the second position of said plug is where the plug meets sufficient resistance to prevent further distal movement.

20. The closure device deployment device of claim 11, further comprising a push tube locking feature structured to lock said push tube in the push tube's second position.

21. The closure device deployment device of claim 11, further comprising a cutter tube extending along the longitudinal axis and moveable along the distal direction upon the application of a third force.

22. The closure device deployment device of claim 21, further comprising a cutter lever assembly structured to rotate and per the rotational movement is structured to apply the third force and drive the cutter tube in a distal direction.

23. The closure device deployment device of claim 22, wherein said cutter lever assembly is structured to maintain a constant pressure angle between a contact pin on the cutter lever assembly and a cam insert on said second sliding member throughout its rotational movement.

24. The closure device deployment device of claim 23, wherein upon the application of the third force through the cutter lever assembly, the distal surface the cutter tube is structured to bend and shear the wire at a location proximal to the plug and at a predetermined angle.

25. The closure device deployment device of claim 24, wherein said bending and shearing is sufficient to create an implant construct comprising:
a plastically deformed bend of the rigid wire that is positioned in secure engagement with the proximal end of said plug, and wherein the footplate remains attached to the wire portion that includes the bend and is positioned distally to the distal end of the plug.

* * * * *